United States Patent
Zebaze et al.

(10) Patent No.: US 9,378,566 B2
(45) Date of Patent: Jun. 28, 2016

(54) METHOD AND SYSTEM FOR IMAGE ANALYSIS

(71) Applicant: StraxCorp Pty Ltd, Coburg, Victoria (AU)

(72) Inventors: Roger Zebaze, Coburg (AU); Eleanor Jean Mackie, Fitzroy (AU); Anne Bohte, East Bentleigh (AU); Aloys Mbala, Epping (AU); Ali Ghasemzadeh, Greensborough (AU); Ego Seeman, Toorak (AU)

(73) Assignee: StraxCorp Pty Ltd, Coburg, Victoria (AU)

( * ) Notice: Subject to any disclaimer, the term of this patent is extended or adjusted under 35 U.S.C. 154(b) by 0 days.

(21) Appl. No.: 14/720,004

(22) Filed: May 22, 2015

(65) Prior Publication Data
US 2015/0262387 A1 Sep. 17, 2015

Related U.S. Application Data

(63) Continuation of application No. 13/395,379, filed as application No. PCT/AU2010/001181 on Sep. 10, 2010, now Pat. No. 9,064,320.

(30) Foreign Application Priority Data

Sep. 11, 2009 (AU) ................................ 2009904407

(51) Int. Cl.
*G06K 9/00* (2006.01)
*G06T 11/00* (2006.01)
(Continued)

(52) U.S. Cl.
CPC ............... *G06T 11/003* (2013.01); *A61B 6/032* (2013.01); *A61B 6/505* (2013.01); *A61B 6/5205* (2013.01);
(Continued)

(58) Field of Classification Search
None
See application file for complete search history.

(56) References Cited

U.S. PATENT DOCUMENTS

| 5,228,068 A | 7/1993 | Mazess |
| 5,480,439 A | 1/1996 | Bisek et al. |

(Continued)

FOREIGN PATENT DOCUMENTS

| EP | 1 653 410 A1 | 5/2006 |
| JP | 5-095940 A | 4/1993 |

(Continued)

OTHER PUBLICATIONS

International Search Report for corresponding International Patent Application No. PCT/AU2010/001181 mailed Dec. 6, 2010.
(Continued)

*Primary Examiner* — Atiba O Fitzpatrick
(74) *Attorney, Agent, or Firm* — Merchant & Gould P.C.

(57) ABSTRACT

A computer-implemented method for analyzing a sample comprising a first material and a second material of generally different densities and having a junction therebetween. The method comprises: defining automatically a plurality of regions of interest within an image of the sample, each of said regions of interest having a width of one or more voxels or pixels; determining respective density, intensity or attenuation profiles within the regions of interest; determining a location of said junction including defining a first reference point within one of said first and second materials and employing the first reference point as current reference point, and (i) determining a closest point to said current reference point that is on said respective profile and in the other of said first and second materials to that of the current reference point; (ii) locating a greatest difference in values of the respective profile between an adjacent peak and trough in a segment of the respective profile between said current reference point and said closest point; and (iii) locating a point of inflexion in said segment.

20 Claims, 29 Drawing Sheets

(51) Int. Cl.
   G06T 7/00    (2006.01)
   A61B 6/03   (2006.01)
   A61B 6/00   (2006.01)
(52) U.S. Cl.
   CPC ............... *G06T 7/004* (2013.01); *G06T 7/0012* (2013.01); *G06T 7/0083* (2013.01); *G06T 2200/24* (2013.01); *G06T 2207/10081* (2013.01); *G06T 2207/10088* (2013.01); *G06T 2207/20104* (2013.01); *G06T 2207/30008* (2013.01); *G06T 2207/30096* (2013.01)

(56) References Cited

U.S. PATENT DOCUMENTS

| | | | |
|---|---|---|---|
| 5,594,775 | A | 1/1997 | Hangartner |
| 5,673,303 | A | 9/1997 | Hangartner |
| 5,931,795 | A | 8/1999 | Manly et al. |
| 6,094,467 | A | 7/2000 | Gayer et al. |
| 6,411,729 | B1 | 6/2002 | Grunkin |
| 6,560,474 | B2 | 5/2003 | Lee et al. |
| 6,625,303 | B1 | 9/2003 | Young et al. |
| 6,744,911 | B1 | 6/2004 | Avila et al. |
| 7,046,834 | B2 | 5/2006 | Lee et al. |
| 2003/0229299 | A1 | 12/2003 | Shimura et al. |
| 2004/0077088 | A1 | 4/2004 | Charles Jr et al. |
| 2004/0151355 | A1 | 8/2004 | Yokota et al. |
| 2007/0167716 | A1 | 7/2007 | Kinahan et al. |
| 2009/0080608 | A1 | 3/2009 | Vizard et al. |

FOREIGN PATENT DOCUMENTS

| | | |
|---|---|---|
| JP | 6-511184 A | 12/1994 |
| JP | 7-289542 A | 11/1995 |

OTHER PUBLICATIONS

Siris, E. et al. "Identification and Fracture Outcomes of Undiagnosed Low Bone Mineral Density in Postmenopausal Women: Results from the National Osteoporosis Risk Assessment", JAMA, vol. 286, No. 22, Dec. 12, 2001, pp. 2815-2822.

Delmas, P. et al. "Changes in bone mineral density explain little of the reduction in vertebral or nonvertebral fracture risk with anti-restorative therapy", Bone, vol. 34, 2004, pp. 599-604.

Zebaze, R. et al. "Measuring Femoral Neck Strength: Lost in Translation?", IBMS BoneKey, vol. 5, No. 9, Sep. 2008, pp. 336-339.

Davis, K. et al. "The Effects of Geometric and Threshold Definitions on Cortical Bone Metric Assessed by In Vivo High-Resolution Peripheral Quantitative Computed Tomography", Calcif Tissue Int, vo. 81, 2007, pp. 364-371.

Ott. S. "When Bone Mass Fails to Predict Bone Failure", Calcif Tissue Int, vol. 53, Suppl 1, 1993, pp. S7-S13.

Siris, E. et al. "Bone Mineral Density Thresholds for Pharmacological Intervention to Prevent Fractures", Arch Intern Med, vol. 164, May 24, 2004, pp. 1108-1112.

Figure 26

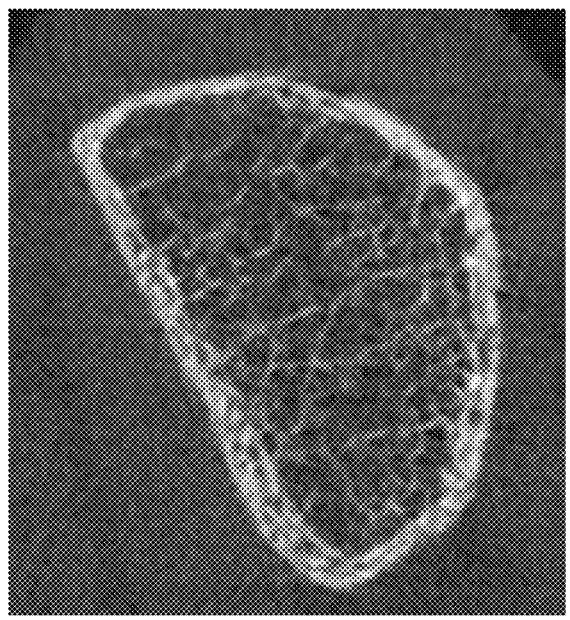
Figure 38A
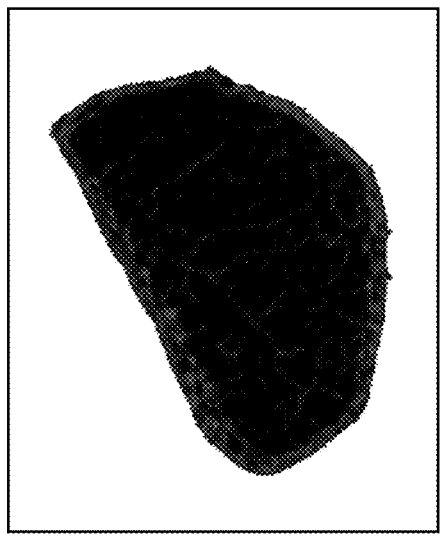 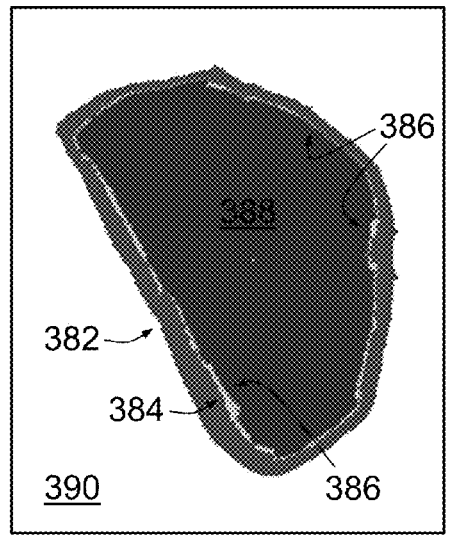
Figure 38B                Figure 38C

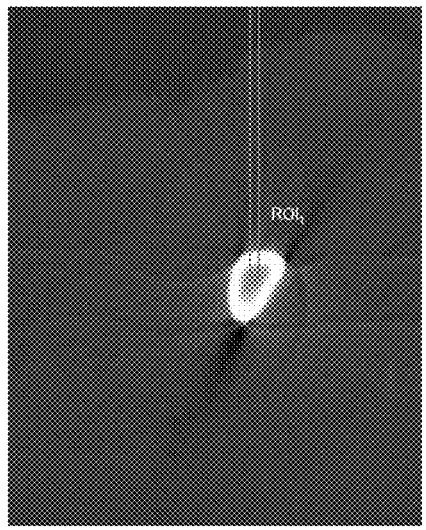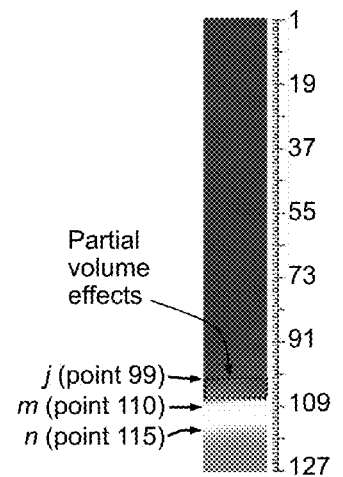
Figure 39A
Figure 39B
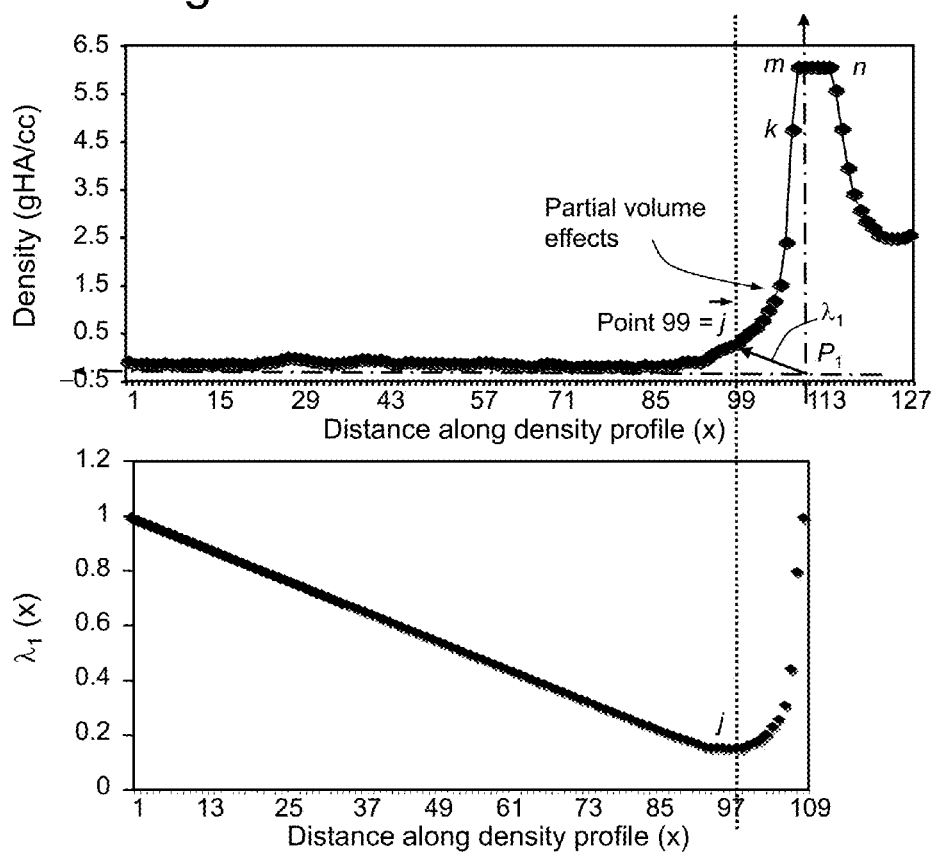
Figure 40

METHOD AND SYSTEM FOR IMAGE ANALYSIS

RELATED APPLICATION

This application is a Continuation of U.S. Ser. No. 13/395,379, filed 24 May 2012, which is a U.S. National Stage of PCT/AU2010/001181, filed 10 Sep. 2010, which claims benefit of Serial No. 2009904407, filed 11 Sep. 2009 in Australia and which applications are incorporated herein by reference. To the extent appropriate, a claim of priority is made to each of the above disclosed applications.

FIELD OF THE INVENTION

The present invention relates to an image analysis method and system for identifying (including automatically if desired) an object or structure from its surrounding environment, separating or distinguishing an object or structure from its surrounding environment, and analysing the object or structure, using—for example—an image of the object or structure, and is of particular but by no means exclusive application in the analysis of biological tissue including the analysis of bone (in vivo or otherwise) and diagnosis of disease such as bone disease, and the analysis or characterization of materials and geological samples. In a particular embodiment, the invention relates to the identification and distinguishing of bone from surrounding tissue (such as muscle and fat), the analysis of its structure and the detection of decayed or abnormal bone (and hence in some case fracture-vulnerable bone). In another particular embodiment, the invention relates to the location or identification of a foreign body embedded within biological tissue (such as muscle).

BACKGROUND OF THE INVENTION

Currently, bone density is the commonly used tool to predict fracture risk and evaluate the effects of treatment on bone but it lacks sensitivity and specificity. More than half of all hip fractures occur in women determined to be without osteoporosis with dual energy X-ray absorptiometry (DXA) with a T-score$\leq$2.5. Furthermore, most women with osteoporosis as defined by DEXA BMD do not sustain fractures (Delmas P. D., Seeman E. *Changes in bone mineral density explain little of the reduction in vertebral or nonvertebral fracture risk with anti-resorptive therapy*, Bone 34(4) (2004) p. 599-604). During drug therapy, only a small proportion of the fracture risk reduction is explained by the increase in bone density (Ott S. M., *When bone mass fails to predict bone failure*, Calcif. Tissue Int. 53(Suppl1) pp. S7-S13). This lack of sensitivity and specificity partly is partly due to the fact that fracture risk is not only determined by bone density but also bone structure (Zebaze R. M. and Seeman S., *Measuring Femoral Neck Strength: Lost in Translation?*, IBMS BoneKEy 5 (2008) pp. 336-339).

Consequently, techniques such as quantitative computed tomography (CT) and magnetic resonance imaging (MRI) are being used to produce images that are then analysed to predict fracture risk, quantify the effects of drugs and determine the effectiveness of various strategies (such as exercise or diet) for the prevention of bone loss. However, parameters derived from these imaging modalities have not proved to be significantly better than bone density measurement, and cannot presently be used as a substitute for bone density measurement.

The problem with these approaches lies not only in image acquisition but also, and more significantly, in image processing. One of the most important problems with existing techniques for assessing bone structure from such images is their reliance on fixed arbitrary thresholds to identify bone within a region of interest (ROI) and to segment (i.e. separate) bone into its various compartments (usually cortical and trabecular bone). Bone architecture differs from person to person and, for this reason, the use of fix thresholds has different and unpredictable consequences on bones from different individuals. Hence, the use of a fixed threshold can create apparent differences where none exist, or obscure differences when they exist.

Furthermore, current methods employ a simplistic model of bone structure. In particular, these methods treat bone as a structure made of two distinct compartments (cortical and trabecular bone). In fact, the so-called 'compact' bone and trabecular ('spongy') bone are extremes of a continuum of variation in porosity from the periosteum to the inner marrow cavity.

In addition, current methods employ so-called 'phantom calibration' to determine the density associated with each pixel within an image. This density is then used to identify bone and assess its structure (hence the term quantitative computed tomography (QCT)). Existing calibration procedures are specific to each scanner manufacturer, so bone structure analysis—performed by software embedded in the scanner—is manufacturer specific.

SUMMARY OF THE INVENTION

According to a first broad aspect of the invention, there is provided a computer-implemented method for analysing a sample comprising a first material and a second material of generally different densities and having a junction therebetween, the method comprising:

defining automatically a plurality of regions of interest within an image of the sample, each of said regions of interest having a width of one or more voxels or pixels;

determining respective density, intensity or attenuation profiles within the regions of interest;

determining a location of said junction including defining a first reference point within one of said first and second materials and employing the first reference point as current reference point, and (i) determining a closest point to said current reference point that is on said respective profile and in the other of said first and second materials to that of the current reference point;

(ii) locating a greatest difference in values of the respective profile between an adjacent peak and trough in a segment of the respective profile between said current reference point and said closest point; and (iii) locating a point of inflexion in said segment.

In an embodiment, the method comprises identifying a necrotic mass from surrounding healthy soft tissue from a difference in attenuation between the necrotic mass and the surrounding healthy soft tissue.

In one embodiment, the method comprises identifying a tissue mass with high attenuation from surrounding healthy soft tissue with lower attenuation from a difference in attenuation between the high attenuation mass and the surrounding healthy soft tissue. The tissue mass may comprise a tumour or calcified tissue.

In another embodiment the first material is bone, and the method comprises:

analyzing the sample including rotating, translating or both rotating and translating one or more of said regions of interest;

defining a plurality of compartments within the sample, the compartments comprising any one or more of:
  i) a compartment bounded by a periosteal boundary and a beginning of the cortex;
  ii) a compartment bounded by a beginning of the cortex and a beginning of the compact cortex;
  iii) a compact (or hard) cortex compartment;
  iv) a trabecularized cortex compartment;
  v) a cortico-trabecular junction compartment; and
  vi) a trabecular compartment; and
determining the local thickness, areas, density or porosity in each of the areas in one or more of said regions of interest.

In one embodiment, the method comprises determining an amount of material in the first material relative to the second material using a first referent and a second referent, the first referent comprising a representative attenuation or density of the first material, the second referent comprising a representative attenuation or density of the second material.

For example, the first referent may be either a maximum or a 95th percentile value of the representative attenuation or density of the first material. The second referent may be either a maximum or a 95th percentile value of the representative attenuation or density of the second material.

In another example, the first material is bone and the second material is muscle tissue at least partially surrounding said bone, and the method includes estimating an amount of mineralized bone matrix in the one or more voxels or pixels. In this example, the method may comprise determining one or more mineralization indices by analysing voxels or pixels which only contain mineralized bone matrix.

The method may comprise determining a porosity of the first material relative to a porosity of the second material. For example, the first material may be bone and the second material muscle tissue at least partially surrounding the bone. The first material may be rock or a plastics material.

The second material may be gas, air or a partial vacuum (which, as will be appreciated by the skilled person, may be referred to as a 'vacuum' if sufficiently hard).

The method may include selecting a range of porosity to be quantified based on a difference between the representative attenuation or density of the first material and the representative attenuation or density of the second material.

In one embodiment, the first material is bone and the second material is muscle tissue at least partially surrounding said bone, and the method further comprises determining one or more fat indices within said bone by comparing attenuation of voxels inside the bone to a representative attenuation of the muscle tissue.

According to this aspect of the invention, there is also provided a system for analysing a sample comprising a first material and a second material of generally different densities and having a junction therebetween, the system comprising:
  a region of interest selector for selecting at least one region of interest in an image of at least a portion of the sample that includes a portion of the first material and a portion of the second material;
  a density profile analyzer for determining a density, intensity or attenuation profile of the sample within the region of interest, and for determining a location of said junction; and
  an output for outputting a result of said analysis;
  wherein said density profile analyzer is configured to define a first reference point within one of said first and second materials and employing the first reference point as current reference point, and (i) determine a closest point to said current reference point that is on said respective profile and in the other of said first and second materials to that of the current reference point;
  (ii) locate a greatest difference in values of the respective profile between an adjacent peak and trough in a segment of the respective profile between said current reference point and said closest point; and
  (iii) locate a point of inflexion in said segment.

In an embodiment, the system is further configured to:
  i) identify a necrotic mass from surrounding healthy soft tissue from a difference in attenuation between the necrotic mass and the surrounding healthy soft tissue, and/or
  ii) identify a tissue mass with high attenuation from surrounding healthy soft tissue with lower attenuation from a difference in attenuation between the high attenuation mass and the surrounding healthy soft tissue In one embodiment, the first material is bone, and the system is further configured to:
  analyze the sample including rotating, translating or both rotating and translating one or more of said regions of interest;
  define a plurality of compartments within the sample, the compartments comprising any one or more of:
    i) a compartment bounded by a periosteal boundary and a beginning of the cortex;
    ii) a compartment bounded by a beginning of the cortex and a beginning of the compact cortex;
    iii) a compact (or hard) cortex compartment;
    iv) a trabecularized cortex compartment;
    v) a cortico-trabecular junction compartment; and
    vi) a trabecular compartment; and
  determine the local thickness, areas, density or porosity in each of the areas in one or more of said regions of interest.

In another embodiment, the system is further configured to determine an amount of material in the first material relative to the second material using a first referent and a second referent, the first referent comprising a representative attenuation or density of the first material, the second referent comprising a representative attenuation or density of the second material.

In this embodiment, the system may be further configured to determine a porosity of the first material relative to a porosity of the second material.

According to a second broad aspect of the invention, there is provided a method for analysing a sample comprising a first material and a second material of generally different densities and having a junction (abrupt or otherwise) therebetween, the method comprising:
  defining a region of interest in a cross sectional image of at least a portion of the sample that includes said junction;
  determining a density profile of the sample within the region of interest and crossing the junction;
  determining a representative density of said second material (such as from the density profile); and
  analysing said sample using said junction used to distinguish said first and second materials.

The characteristics of the invention allow the method to operate automatically (and the system described below to be automated).

The method may include locating the junction (using, for example, a distance function relative to a suitably selected point) in the density profile between the first material and the second material.

Thus, the first and second materials could be two biological tissues of different densities (such as bone or a tumour and surrounding soft tissue respectively), but could be any two materials that allow a cross sectional image to be made and have generally different densities. For example, the method and system could be used to identify and provide an analysis or characterization of a sample comprising a bullet (or other metallic object) embedded in muscle or other biological tissue.

This is achieved, it will be noted, without requiring the use of thresholds in the image analysis, such as to distinguish bone from surrounding soft tissues or into various compartments.

It should also be noted that "material" is used in its broadest sense. A material may be an object (or part thereof), a structure within an object, a volume of gas, or a largely evacuated volume.

In one embodiment, the method further comprises determining an architecture of the first material (such as a bone architecture).

In another embodiment, the method comprises detecting decay or abnormality in the first material (such as decay or abnormality in the structure of bone). For example, the method may include identifying fracture-vulnerable bone.

Locating the junction in the density profile may comprise locating a point in the density profile that is closest to a reference point having the same position as the representative density of the first material and a density similar or lower than that of second material.

In this embodiment, locating the junction may involve finding a minimum in the expression $\sqrt{x_i^2+y_i^2}$ in a reference frame within the density profile centred on $(x_i, y_i)=(0,0)$.

In this embodiment, locating the junction may involve finding a maximum in the expression $\sqrt{x_i^2+y_i^2}$ in a reference frame within the density profile centred on $(x_i, y_i)=(0,0)$.

In another embodiment, locating the junction involves locating a point of greatest rate of change in the density profile in a portion of said region of interest that is bounded by said point of maximum density difference and that includes said second material.

In still another embodiment, locating the junction involves locating a point of smallest rate of change in the density profile in a portion of said region of interest that is bounded by said point of maximum density difference and that includes said second material.

In a certain embodiment, locating the junction includes locating a point of inflexion in the density profile.

In still another embodiment, locating the junction includes forming a second order derivative of the density profile (that is, of one or more portions of the density profile, for example, in the highest 'hills' as described below), such as to locate a point of inflexion in a first order derivative in one or more segments of the density profile curve (corresponding, for example, to respective compartments within the sample).

In some embodiments, the region of interest includes at least one further junction that is between said first material and a further portion of said sample that comprises either said second material, a third material or a vacancy, and the method further comprises:

determining a representative density of said further portion; and locating a further junction in said density profile in a portion of said region of interest that is bounded by said point of maximum density and that includes said further portion.

In this embodiment, the method may include further analysing the first material by using only portions of said sample between the junction in said density profile and the further junction in said density profile.

Locating the further junction in the density profile may comprise locating a point in the density profile that is closest to a further reference point having the same position as point of maximum density difference and the same density as the representative density of the further portion.

The method may further comprise optimizing the position of the selected region of interest for use by the density profile analyzer in determining the density profile by adjusting the position of the region of interest.

The method may further comprise merging a plurality of regions of interest.

The method may further comprise identifying one or more points of inflexion in the density profile, particularly within the first material.

The method may further comprise identifying one or more points of inflexion in the density profile (such as within the first material), to define a plurality of compartments within the sample.

For example, bone may be characterized as a plurality of compartments according to this embodiment, hence without using thresholds.

In one embodiment, the first material is bone, and the compartments comprise any one or more of:
  a compartment bounded by a periosteal boundary and a beginning of the cortex;
  a compartment bounded by a beginning of the cortex and a beginning of the compact cortex;
  a compact (or hard) cortex compartment;
  a trabecularized cortex compartment;
  a cortico-trabecular junction compartment; and
  a trabecular compartment.

The importance of distinguishing the periosteal boundary, the beginning of the cortex and the beginning of the hard cortex arises because: (i) the periosteal boundary is the edge marking the beginning of the bone (though some voxels may comprise different proportion of tissue and bone, so may be tainted by artefacts such as partial volume effects (PVE), (ii) the beginning of the cortex marks the point where most of the attenuation within voxels are due to bone tissue, and hence the point where the bone is considered to start, and (iii) the beginning of the compact cortex corresponds to the first strip with attenuation almost exclusively due to bone tissue with almost no artifact due PVE.

Hence, voxels or pixels located between the periosteal boundary and the beginning of the hard cortex are tainted by partial volume effects (PVE), that is, their attenuation is partly due to surrounding soft tissues or other artefacts.

In this embodiment, it should be noted, these compartments can be defined in different terms but to essentially the same effect. Thus, in a this embodiment, the first material is bone, and the compartments comprise any one or more of:
  a compartment bounded by a periosteal boundary and a beginning of the compact cortex;
  a compartment bounded by a beginning of the compact cortex and the beginning of the an outer transition zone;
  an outer transition zone;
  an inner transition zone and;
  a trabecular compartment.

The ability to identify this transition between the periosteal boundary (viz. purely soft tissue) and the beginning of the compact cortex (purely bone) is unique to the method of this aspect, and may have many important advantageous applications. According to this aspect, the influence of artefacts such as PVE on the assessment of the structure may be allowed for, the dimensions of the bone may be determined, and the structure of the bone may be assessed with minimal artefact from PVE.

Hence, in one embodiment, the method includes minimizing PVEs when analysing bone structure, while in another embodiment the method includes determining the dimensions of a structure within an image (such as a tumour, an abscess or a haemorrhage) while minimizing PVEs.

In one embodiment, the method includes determining a proportion of the cortex that has a trabecular-like appearance.

In one embodiment, the method includes determining an average of the cortical thicknesses of the compact cortex.

In one embodiment, the method includes determining an average of the cortical thicknesses of the cortical mass.

In one embodiment, the method includes determining an average of the cortical thicknesses of the trabecularized cortex.

In one embodiment, the portion includes a trabecular portion of said bone sample and a cortical portion of said bone sample.

The method may include imaging the internal region of the bone sample.

The imaging may comprise computed tomography imaging.

In certain embodiments, the imaging is conducted in vivo.

In one embodiment, the portion of the sample comprises a radial strip.

In an embodiment, the method comprises imaging a plurality of portions of the sample and determining respective density profiles (such as radial bone density profiles) of each of said portions.

The method may include automatically identifying bone within a sample.

The method may include determining any one or more indices from the group consisting of:
  the thickness of the cortex, of the trabecularized cortex or of the transition zone;
  the cortical area or of the trabecularized cortex;
  the porosity of cortex, of the trabecularized cortex, or of the transition zone;
  whether the cortex or the trabecularized cortex is normal regardless of its absolute thickness or area;
  whether the cortex or the trabecularized cortex has been subject to resorption (and, hence, has lost bone); and
  trabecular architecture and porosity from the analysis of the profile;

The method may include determining the loss of differentiation between the cortical and the trabecular compartments.

The method may include identifying non-bone tissue (i.e. pores and fat tissues) within the periosteal envelope.

The method may comprise determining a radius, perimeter length or cross sectional area of the first material (such as one or more radii of a bone sample point by point around the perimeter of the bone sample).

The method may comprise determining the second moment area (or moment of inertia) of the first material (such as bone point by point around the perimeter of the bone sample).

The method may comprise determining a mass adjusted second moment area of a cross section of bone point-by-point around its perimeter The method may comprise determining the section moduli (and mass adjusted section moduli) of a cross section of bone.

The method may comprise determining a buckling ratio (or a mass adjusted buckling ratio) of a cross section of bone.

The method may comprise determining the area of a cross section of bone.

The method may comprise determining the perimeter of a cross section of bone.

The method may comprise determining the section moduli (and mass adjusted section moduli) of a cross section of bone using specific functions described below to separate bone from soft tissues.

The method may comprise determining the polar moment of inertia moduli (and mass adjusted polar moment of inertia) of a cross section of bone using specific functions described below.

The method may comprise determining the radii of the cross section of bone point-by-point around its perimeter, such as by using specific functions described below.

The method may comprise identifying trabecular bone within the sample and determining one or more trabecular indices, such as trabecular size or trabecular separation.

The method may comprise determining the degree of mineralization of bone using the surrounding muscular tissue as referent.

The method may comprise determining the absolute density (such as in g/cc or mgHA/cc equivalent) of a constituent (or element) within the region of interest ROI using the attenuation of the second material (such as muscle tissue) as referent.

The method may comprise determining the relative density (such as in percent) of an object (or structure) within the region of interest using the attenuation of the second material (such as muscle tissue) as referent.

In this embodiment, the method may comprise identifying abnormality within the bone sample from any one or more of the indices.

In one embodiment, the method includes determining whether the bone sample is abnormal based on having an abnormal cortex, an abnormal trabecular compartment, or both an abnormal cortex and an abnormal trabecular compartment.

The system and method may be embodied in a computer-readable medium that can be installed in personal computers, CT machines or MRI machines allowing a flexible and robust analysis of images for automated radiological diagnosis of diseases and, in particular, allowing automated analysis of bone structure to diagnosis osteoporosis, assess fracture risk and the effects of disease and treatments in bone using CT, QCT and MRI source files (DICOM, JPEG, TIFF or other imaging files) in vivo and in vitro. The invention is expected to be useful in the diagnosis of osteoporosis, of certain metabolic bone diseases (e.g. osteomalacia or paget disease) and infiltrative bone diseases such as bone metastasis.

It should also be noted the present invention allows the assessment of sample (such as bone) structure and diagnosis of bone diseases such as osteoporosis using, for example, a personal computer (operated by, for example, a physician or scientist).

In one embodiment, the method comprises identifying and analyzing a necrotic mass from surrounding healthy soft tissue from the difference in attenuation between the necrotic mass and the surrounding healthy tissue. This has applications for the diagnosis and the monitoring for example of internal (or deep) abscesses.

In one embodiment, the method comprises identifying and analyzing an ectopic calcification from surrounding soft tissue. This has potential applications for the diagnosis and monitoring of cardiovascular diseases.

In one embodiment, the method comprises identifying and analyzing kidney stones. Kidney stones have a majority (80%) of calcium content and hence can be treated as bone tissue in an ectopic position. This will a mean for an automated diagnosis of the majority (perhaps 80%) of kidney stones.

Thus, the lifetime prevalence of kidney stones is 10% or roughly around 2 million patients per year in the USA, so an automated diagnosis of this condition will be of great help for health care professionals and, in particular, for radiologists.

In one embodiment, the method comprises identifying and analyzing a calcified other tumour.

In one embodiment, the method comprises identifying and analyzing an object within an image in a non-medical discipline.

In a particularly advantageous embodiment, analyzing the sample comprises analyzing the image using a rotatory arm width.

According to this broad aspect, the invention also provides a method for analysing a sample comprising a first material and a second material of generally different densities and having a junction therebetween, the method comprising:
 defining a region of interest in a cross sectional image of at least a portion of the sample that includes said junction;
 determining an arm width over which said portion of said sample is locally linear; and
 analyzing said image including rotating said arm width, translating said arm width, or both by rotating and translating said arm width.

According to this aspect, the invention also provides a system for analysing a sample comprising a first material and a second material of generally different densities and having a junction therebetween, the system comprising:
 a region of interest selector for selecting a region of interest in a cross sectional image of at least a portion of the sample that includes said junction;
 a density profile analyzer for determining a density profile of the sample within the region of interest and crossing the junction, for determining a representative density of said second material, and for performing an analysis of said sample using said junction to distinguish said first and second materials; and
 an output for outputting a result of said analysis.

The system may include a region of interest position adjuster, adapted to optimize the position of the selected region of interest for use by the density profile analyzer in determining the density profile.

The system may include a region of interest merger, adapted to merge a plurality of regions of interest.

Thus, the analysis of the sample may involve using the region of interest selector plural times, producing a plurality of regions of interest; the region of interest merger is adapted to merge the plurality of regions of interest (generally after each has been successfully tested for suitability), including correctly handling overlapping portions of the plurality of regions of interest, to construct an image, such as a cross sectional image, of the sample.

The density profile analyzer may also be adapted for locating the junction (using, for example, a distance function) in the density profile between the first material and the second material.

The system (and in particular the density profile analyzer) may have one or more modules adapted to perform respective optional steps of the method of the first aspect.

The system may include an evacuatable sample chamber or alternatively a sample may comprise a second material of known characteristics (such as water) placed around the first material to serve as a referent for the analysis of the first material (just as, with bone in vivo, the sample comprises bone surrounded by muscle, which can be essentially treated as water).

This allows a sample to be created wherein one of the first and second materials comprises an evacuated volume (such as adjacent to or surrounding the other of the materials).

According to a further broad aspect, the invention provides executable instructions or software (such as embodied in a computer readable medium, for example with the executable instructions or software imbedded or permanently stored therein), that, when executed by a computer or processor of a computer, cause the computer or processor of the computer to perform the method for analysing a sample described above.

The result of the analysing step would generally be outputted, either for review or further analysis, but may be outputted to a memory or memory medium, such as for later review or further analysis.

According to another broad aspect, the invention provides a computing device provided with executable instructions or software that, when executed by the computing device or by a processor of the computing device, cause the computing device or processor of the computing device to perform the method for analysing a sample described above.

It should be noted that any of the various features of each of the above aspects of the invention can be combined as suitable and desired. It should also be noted that embodiments that refer to the analysis of bone may also be applied, suitably modified where necessary, to other samples.

BRIEF DESCRIPTION OF THE DRAWING

In order that the invention may be more clearly ascertained, embodiments will now be described, by way of example, with reference to the accompanying drawing, in which:

FIG. 22A is an exemplary image of a bone sample, FIG. 22B illustrates the identification of pores within the cortical mass in one column, and FIG. 22C is a binarized plot of bone versus non-bone pixels along the line analysed;

FIG. 26 is a view of a control screen of the image processor of the system of FIG. 1;

FIG. 38A is a greyscale image of a distal radius reconstructed from high-resolution peripheral quantitative computed tomography (HRpQCT) data;

FIG. 38B is an image of the sample depicted in FIG. 38A, reconstructed by the system of FIG. 1 after extraction of the periosteal surface;

FIG. 38C is another view of the sample of FIG. 38A, showing the segmentation of the same image by the system of FIG. 1 into four bone compartments;

FIG. 39A is an image generated by the system of FIG. 1 of a sample comprising the head of a safety pin embedded in muscle;

FIG. 39B is an enlargement of the initial region of interest of the image of FIG. 39A;

FIG. 40 includes a plot of the density profile curve (upper register) associated with $ROI_1$ of the image of FIG. 39A and a plot of the function (lower register) associated with the density profile curve, both generated by the system of FIG. 1;

DETAILED DESCRIPTION OF THE EMBODIMENTS

Figure 1:
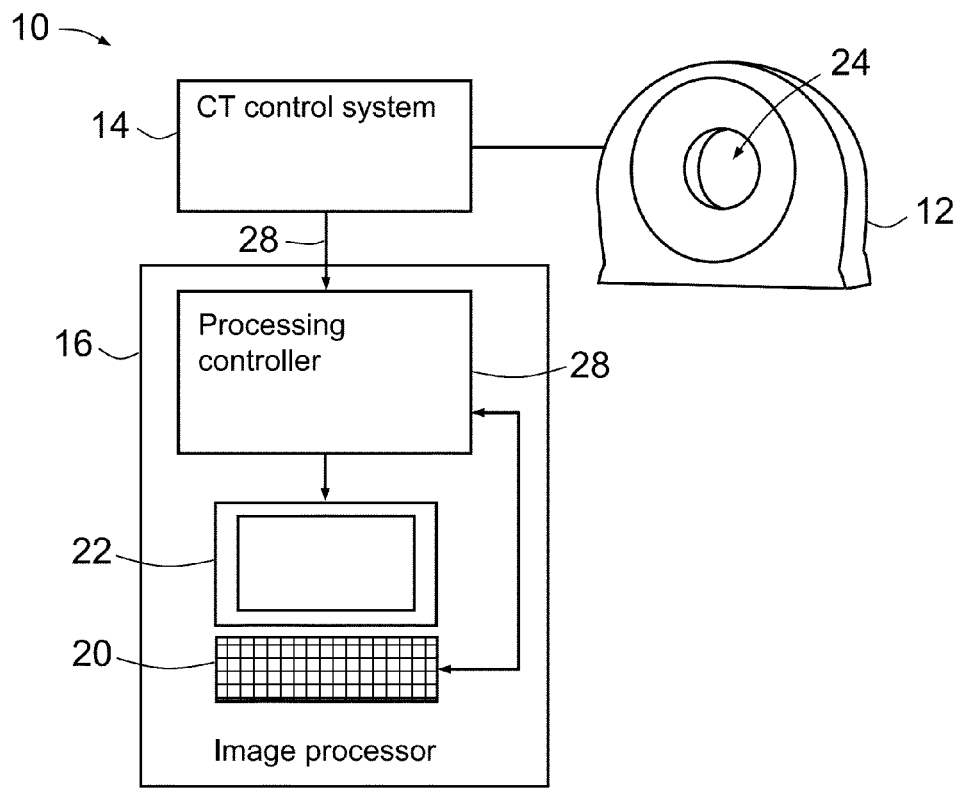
FIG. 1 is a schematic view of a system for detecting fracture-vulnerable bone according to an embodiment of the present invention.

According to an embodiment of the present invention, there is provided a system for detecting fracture-vulnerable bone, shown schematically at 10 in FIG. 1.

System 10 comprises a CT scanner 12, CT control system 14 and an image analyser in the form of image processor 16. Image processor 16 includes a user interface 18 comprising an input device and an output device. The input device is in the form of a keyboard 20 for controlling image processor 16, and the output device is in the form of a display 22 for displaying images from the CT scanner 12 before and after processing by image processor 16. CT scanner 12 is configured to perform CT scans of a sample located within central scanning volume 24 of CT scanner 12 and to output digitized scan data to CT control system 14; CT control system 14 is configured to generate image data from the data received from CT scanner 12, and to output these image data to image processor 16.

In this embodiment, the image data comprises a set of individual image slices or strips through the sample but, in other embodiments, other sections may be used (such as coronal, transverse or oblique sections).

It will be appreciated that system 10 may operate in online and off-line modes. In the online mode, image processor 16 receives data directly from CT control system 14 (during or soon after scanning of the sample). Such an arrangement may be used in a clinical setting, especially if the detection of any fracture-vulnerable bone is urgent. In this online mode, the data is transmitted to image processor 16 via a data link (connected to respective USBs of the CT control system 14 and image processor 16) or a communications network (to which CT control system 14 and image processor 16 are both connected, such as in the form of the internet); this link or network is shown schematically in FIG. 1 at 26.

In the off-line mode, image processor 16 receives data collected earlier by CT scanner 12 and CT control system 14; the data may be transmitted to image processor 16 via communications link or network 26, or by any other suitable means (including on portable computer readable medium, such as CD-ROM, flash card or the like).

Image processor 16 includes a processing controller 28 that is in data communication with input 20 and output 22 and configured to process image processing instructions in accordance with a processing procedure (discussed below) and to output processing outcomes (which may comprise images and/or detection results) to display 22.

Figure 2:
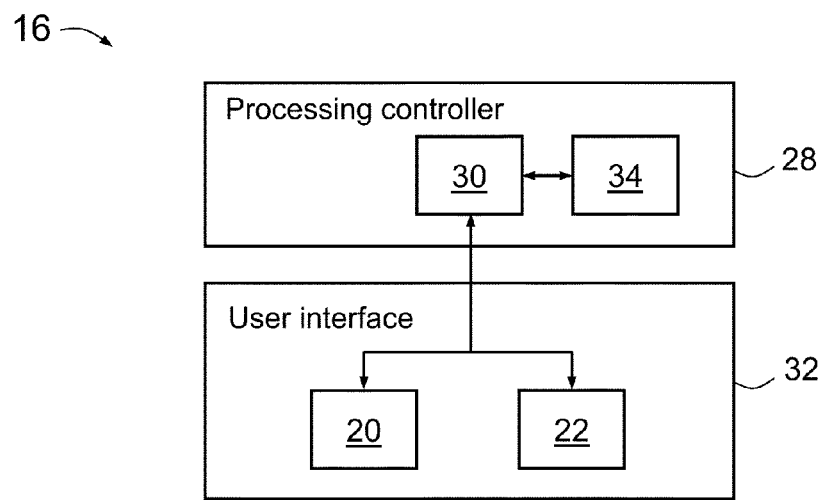
FIG. 2 is a schematic view of the image processor of the system of FIG. 1.

Referring to FIG. 2, processing controller 28 comprises a digital processor 30 that processes the processing instructions in accordance with the processing procedure and—and described above—outputs processing outcomes to display 22. Keyboard 20 and display 22 together constitute a user interface 32. Typically, the processing instructions are stored as program code in a memory 34 of processing controller 28 but can also be hardwired. Herein the term "processor" is used to refer generically to any device that can process processing instructions in accordance with the processing procedure and may comprise: a microprocessor, microcontroller, programmable logic device or other computational device, a general purpose computer (e.g. a PC) or a server.

Figure 3:
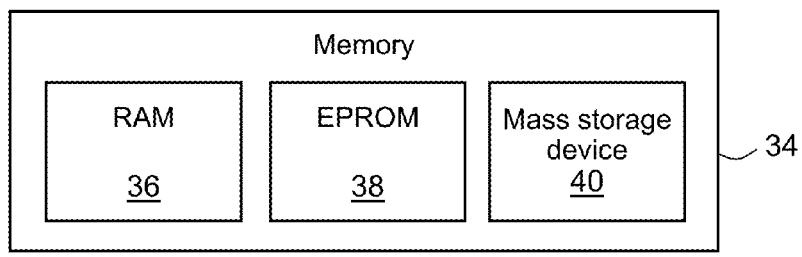
FIG. 3 is a schematic view of the memory of the processing controller of the image processor of the system of FIG. 1.

FIG. 3 shows a block diagram of the main components of memory 34. Memory 34 includes RAM 36, EPROM 38 and a mass storage device 40. RAM 36 typically temporarily holds program files for execution by the processor 30 and related data. EPROM 38 may be a boot ROM device and/or may contain some system or processing related code. Mass storage device 40 is typically used for processing programs.

Figure 4:
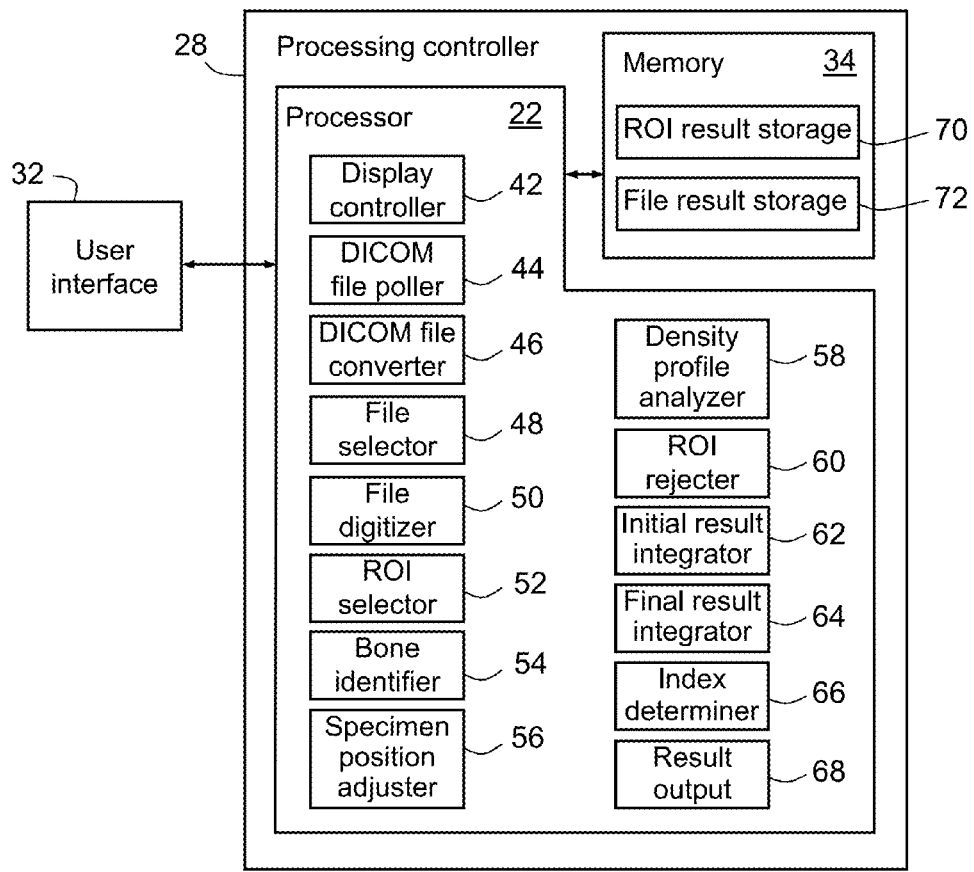
FIG. 4 is another, more detailed schematic view of the image processor of the system of FIG. 1.

FIG. 4 is another schematic view of user interface 32 and processing controller 28 of system 10 of FIG. 1, with more detail shown in processing controller 28. Specifically, processor 30 of processing controller 28 includes a display controller 42 for controlling display 22, a DICOM file poller 44 for polling DICOM (Digital Imaging and Communications in Medicine') files from a staging area (typically CT control system 14), a DICOM file converter 46 for converting DICOM files into images for display, a file selector 48 controllable to select the files to be processed by image processor 16, a file digitizer 50 for digitizing the selected files, a ROI selector 52 for selecting regions of interest, a bone identifier 54 for identifying bone within a region of interest, a specimen position adjuster 56, a density profile analyzer 58 for analyzing the density profile of a sample of bone, a ROI rejecter 60, an initial result integrator 62, a final result integrator 64, an index determiner 66, and a result output 68. Index determiner 66 is adapted to determine various indices characterizing the bone sample, such that image processor 16 can transforms image data indicative of the appearance of a bone sample into indices indicative of various physical properties of the sample.

Memory 34 of processing controller 28 includes a ROI result storage 70 and a file result storage 72.

Figure 5:
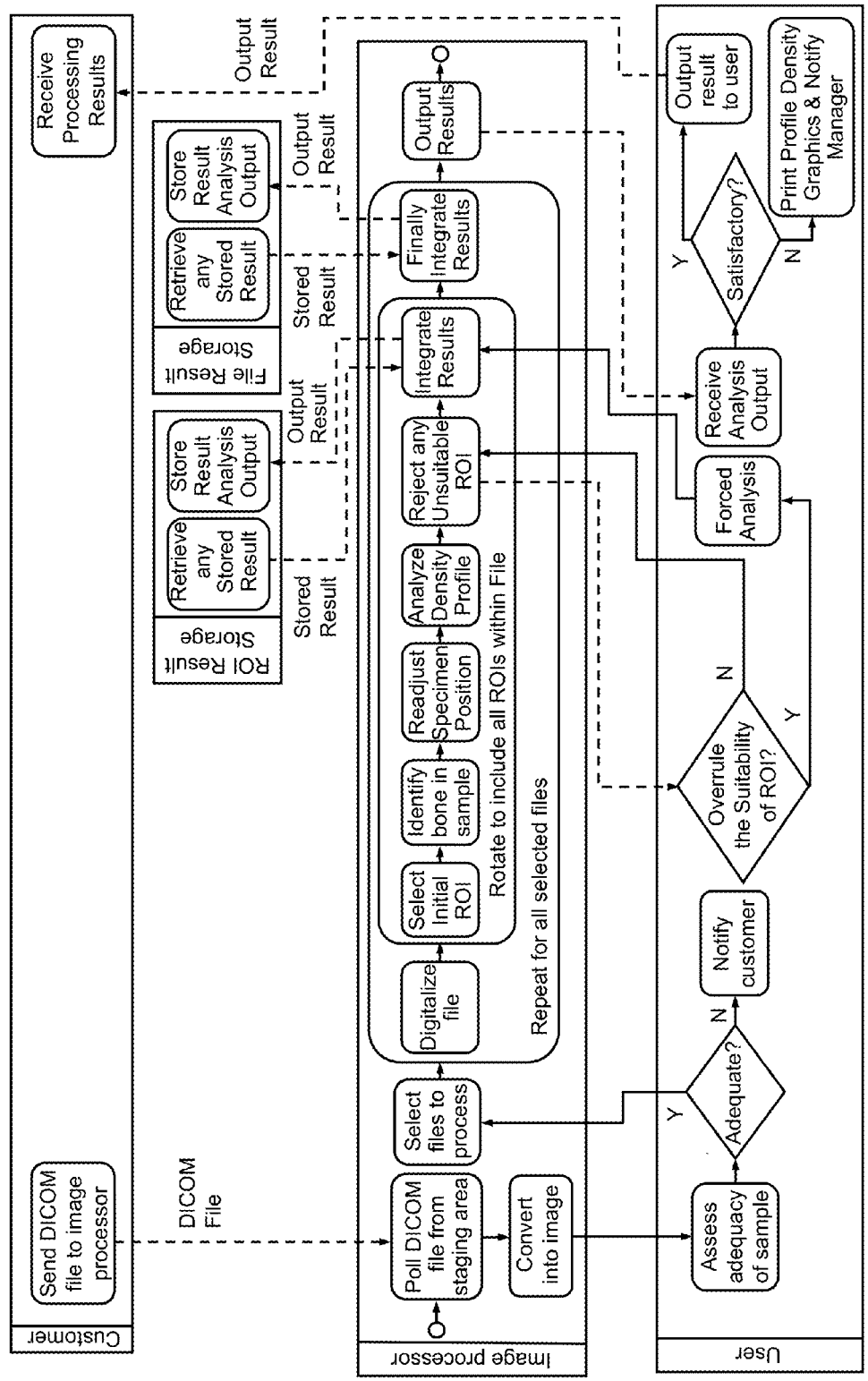
FIG. 5 is a system flow diagram of the system of FIG. 1 (including interaction with a user and customer)
Figure 6:
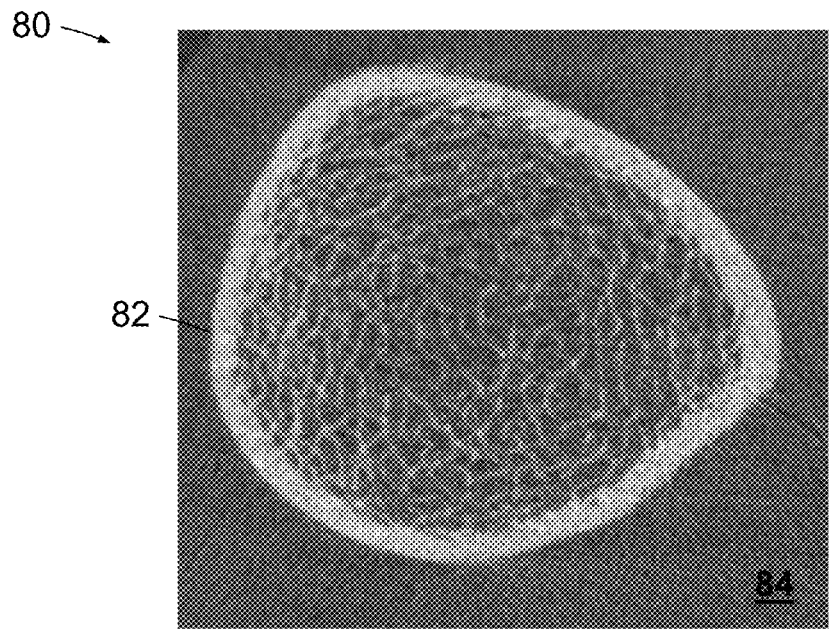
FIG. 6 is an exemplary image of bone as output by the image processor of the system of FIG. 1.

The processing instructions that embody the processing procedure are in the form, as described above, of program code stored in memory 34, and are adapted to control processing controller 26 to perform the processing procedure, as shown schematically in FIG. 5. Referring to FIG. 5, image processor 16 receives (in either online or off-line mode) a DICOM file (collected—possibly in vivo—of a sample of bone) by polling CT control system 14, and stores the file in memory 34. The received file, in this embodiment, is a DICOM file but in other embodiments may be in a different image format, such as JPEG or TIFF. Image processor 16 converts the file into an image and outputs the image to display 22 so that the user can view the image to be processed. FIG. 6 is an example of such an image 80 of a sample of bone 82 surrounded by soft tissue 84. This allows the user to assess the adequacy of the sample by verifying that the appropriate file (e.g. correct bone site) has been uploaded and that the image is of sufficient quality for the processing to proceed. If these conditions are satisfied, the user controls image processor 16 to select the individual files from within the DICOM file (that is, corresponding to specific image slices through a region of interest (ROI) that he or she wishes to analyze) for processing. If the user does not specify the individual files to be processed, image processor 16 continues with a default selection of the number of slices. The user then controls image processor 16 to commence the processing procedure.

The user may also control system 10 to skip the step of viewing the image if sufficiently confident that the image is of high enough quality such that no additional verification is needed. In these circumstances, system 10 automatically uploads and analyses the sample without further user intervention, and image processor 16 initiates analysis without instructions from the user.

Initially, image processor 16 digitizes the files using conventional techniques. Any other desired, conventional pre-processing may also be performed at this point.

The first step performed by image processor 16 is to identify the material of interest (in this example, bone). This initial identification of the material of interest is done by localizing a point with a density representative of the density of the material. In the case of a CT scan image sample containing bone tissue, a point (B) with the representative density is the pixel with the highest attenuation (or density). (In other embodiments, the point with the density representative of density of the material to be analysed may be the point with the lowest attenuation value, which may be—for example—for the initial identification of an abscess, as abscesses have low attenuation values.)

From point B (cf. FIG. 7A), image processor 16 uses radii $r_1$, $r_2$, $r_3$ and $r_4$ of the bone at 0°, 90, 180° and 270° respectively to determine a geometric centre (C) of coordinates (x,y), in this embodiment according to:

$$(x, y) = \left( \frac{(r_1 + r_3)}{2}, \frac{(r_2 + r_4)}{2} \right). \quad (1)$$

Image processor 16 also determines the centroid (i.e. centre of mass) G ($x_G$, $y_G$) from the initial centre (I) as:

$$\begin{cases} x_G = \dfrac{\sum_{i=1}^{n} A_i * x_i}{A_i * x_i} \\ Y_G = \dfrac{\sum_{i=1}^{n} A_i * Y_i}{A_i * Y_i} \end{cases},$$

Figure 7A:
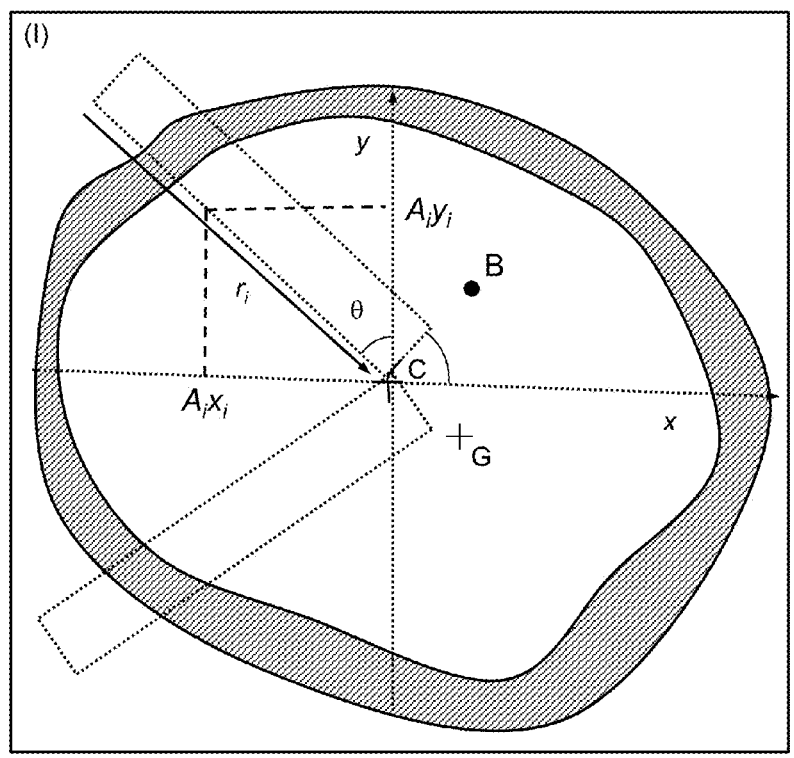
FIG. 7A is a schematic depiction of the determination of the centre of mass of a bone sample by the image processor of the system of FIG. 1.

$A_i$ is the of attenuation (or density) of pixel i and $x_i$ and $y_i$ its coordinates in the referential of centre (C). This process is illustrated in FIG. 7A for the example of FIG. 6.

Depending on the indices to be computed, image processor 16 uses either C or G.

Image processor 16 next determines the appropriate arm width (AW) for the analysis. Image processor 16 does not analyse the entire cross section (or file content) at the same time. Each file is subdivided into regions of interest (ROI) of specific length ($L_{ROI}$) and width. A ROI may be referred to as an 'arm', so the width of the ROI is called 'arm width' or AW. The AW used by image processor 16 depends on the indices to be determined and, as is described below, the size of the material to be analysed. Image processor 16 employs an appropriate AW in the form of:

$$AW \leq r_i * \tan(\arccos(\Delta)), \quad (2)$$

where $\Delta$ is the estimated curvature of the bone from the chosen centre (C or G) and $r_i$ is the smallest of the four radii (viz. $r_1$, $r_2$, $r_3$ and $r_4$) calculated above.

For most indices, image processor 16 commences from centre C, and $\Delta$ is set to a value of 0.98; this AW is designated as $AW_1$. For a $\Delta$ of 0.98, there is a negligible effect (0.02) from the curvature of the bone on the analysis. That is, the bone appears—in effect—essentially locally 'flat', which is why the arccosine value of 0.98 is chosen. For example, the smallest radius at the distal radius is ~8 mm giving image processor 16 an AW of ~1.62 mm at the distal radius. The smallest radius at the tibia is 12 mm, for which image processor 16 employs an AW of ~2.42 mm. The AW is chosen to be wide enough to allow pores and resorption cavities to be detected in the density profile curve (as seen above). Pores and resorption cavities can be up to 600 microns in diameter in humans, so the AW used by image processor 16 should be greater than or equal to 1 mm when the porosity of human bone is being assessed. Notably, as no two bones have exactly the same dimensions, images of no two bones are processed in the same fashion by image processor 16, and the processing of bone structure according to this embodiment is specific to each bone.

For other indices, such as strength parameters or external dimensions, image processor 16 commences from G and uses another arm width (represented by $AW_2$). $AW_2$ is determined by image processor 16 with a much smaller curvature $\Delta$ (0.999) according to:

$$AW_2 = r_i * \tan(\arccos(0.999)). \quad (3)$$

$AW_2$ is smaller than $AW_1$ because the desire here is to have the periosteal and endocortical surfaces small enough to be representative of small arcs, as the immediate aim is to perform an accurate calculation of the internal and external geometry of the cross section (rather than detect porosity). At the distal radius and tibia respectively, $AW_2$ is between ~360 microns and 590 microns.

Image processor 16 can employ a greater default curvature, but a value of $\Delta$ of 0.999 is employed in this embodiment. A $\Delta$ value of 0.999 is used in this example to determine the precision and the accuracy of the analysis provided by image processor 16. It should also be noted that $\Delta$ is a user controllable setting in image processor 16. This and other such settings allow the user to minimize the effect on the analysis of irregularities of the periosteal rim (i.e. deviation from a portion of circle). As such it is controllable by the user to minimize any potential error produced by periosteal rims of ROIs deviating from portions of circles. The default value of $\Delta = 0.999$ is used by image processor 16 because, with this value, and in view of the ranges of human bone diameters in vivo (typically less than 5 cm), $AW_2$ is 1 mm or less. That is, the periosteal boundary of a bone is regular at a local level (within, say, a length of 1 mm).

As image processor 16 employs a calibration, image processor 16 can readily identify muscle tissue and uses muscle density as a referent. The ratio of muscle to non-muscle tissue is then used as a form of calibration. This is why, for many calculations, identifying the muscle and retrieving its density is employed in the processing performed by image processor 16 (for which reason image processor 16 employs a different arm width, $AW_3$, as described below). Two of the advantages resulting from this are (i) cumbersome and resource consuming daily calibration for the purpose measuring a referent density is not needed when scans are to be analysed using image processor 16, and (ii) image processor 16 can operate and analyse image files from essentially any CT, not only quantitative computed tomography. This may obviate the need of having a QCT. Furthermore, with this approach, image processor 16 can provide existing CT (or MRI) with a bone structure analysis function. (Existing CT machines, though widely available, lack a bone analysis function so cannot be used for the diagnosis of osteoporosis).

Many indices such as trabecular parameters or indices of strength or porosity require an a priori detection of the muscle density, so image processor 16—in these instances—employs a larger arm width, $AW_3$:

$$AW_3 = r_x * \tan(\arccos(0.965)), \quad (4)$$

where $r_x$ is the radius selected as the specific angles outside the bone, with these angles preset based on local anatomy. Soft tissue outside the bone at these specific angles is predominantly muscle. Image processor 16 employs, for example, 90° for the radius and ~65° for the tibia. $AW_3$ is chosen to be wide enough to include sufficient muscle tissue so that its density can be adequately determined, including for use as a calibration referent.

After determining the centres and the appropriate arm width, image processor 16 determines the appropriate angle of rotation 8. Image processor 16 has a default angle of rotation $\theta_1$ of 5°, which is appropriate for most bones owing to the expected range of radii. However, this angle may not be appropriate in some circumstances, so the appropriateness of the rotation angle is tested before proceeding to the analysis of other ROIs (as described below). A $\theta_1$ of 5° gives 72 ROIs per slice analysed.

For indices using $AW_2$ as a rotatory arm width, image processor 16 has a preset angle of rotation $\theta_2$ of 1.5°. This is small enough for the bone edges (viz. periosteal surface) to appear locally linear (or at least able to be approximated by an arc of a circle). This gives a total of 240 ROIs. Image processor 16 is operable to employ a preset angle of rotation 8 of 1° (or less) if desired by the user.

In order to test the appropriateness of the angle of rotation 8, image processor 16 verifies whether the following condition is satisfied:

$$\sin \theta * r_i < AW, \quad (5)$$

where $r_i$ is the smallest of the four radii defined above.

If this condition is not satisfied, for analysis using $AW_1$, the angle of rotation $\theta_1$ is deemed unsuitable and image processor 16 selects the next smaller angle below 5° (such as 4°, but in any event suitable for use as a rotation angle) according to equation 5. This condition ensures that no fragment of the cross section is left unanalysed. Image processor 16 informs the user if an angle less than 5° has been used.

The same procedure is performed if $AW_2$ and $\theta_2$ (1.5°) are used and angles smaller than 1.5° are selected above by image processor 16 as above using equation 5.

It should be noted that the angle of rotation (θ) and the AW (as determined by Δ) are parameters set or selected by the user to control the analysis by image processor 16. Although they have preset values, they are not fix. The preset values are chosen for an optimal analysis of bone structure in humans. The user can thus adjust θ and Δ by controlling the settings controls of image processor 16 for an optimal analysis of bones, in particular non-humans bones.

For example, bone diameter can reach up to 10 cm in some animals, such as horses. To ensure that the length of periosteal rim remains within a millimeter in length (to minimize the effect of any potentially curvature irregularity), Δ is set to 0.9999 and $\theta_2$ readjusted to 0.5°; the larger cross section of such a bone is subdivided in 480 ROIs of ~700 micron length each, allowing an accurate measurement of the perimeter and surface.

Image processor 16 then selects an initial region of interest (ROI) which, in this embodiment, is vertical. This initial ROI is a transection of the width of image processor 16 $AW_1$ (or $AW_2$) starting at C (or G) and of the length going from the centre and length L, being half of the maximal diagonal of the entire selection from the centre (C or G), that is, $L=\sqrt{a^2+b^2}$ (where a and b are defined below). It should be noted that, in this embodiment, the material (or, strictly speaking, the image of the material) may be regarded as within a parallelogram with sides of length a and b.

When the ROI has been selected, image processor 16 properly positions the bone within the ROI before proceeding. The process of positioning involves rotating the bone sample anticlockwise or clockwise from respectively the first or the last column so that the beginning of the cortex starts at the same line in the first and last columns. This ensures that the bone sample is horizontally positioned. (No rotation is performed by image processor 16 if the sample is already horizontal.) The suitable positioning of the bone sample is performed to avoid an angular position of the sample that would affects the density profile.

Before actually performing the rotation, image processor 16 identifies the apparent cortical mass of the bone sample. This is the cortical mass uncorrected for the angular (i.e. non-horizontal) position of the sample. Within that apparent cortical mass, image processor 16 determines the beginning of the bone at the first and at the last columns. This allows the algorithm to recognize if the sample is perfectly horizontal. As mentioned above, if the sample is perfectly horizontal no rotation is performed; otherwise, the appropriate rotation is performed.

Figure 7B:
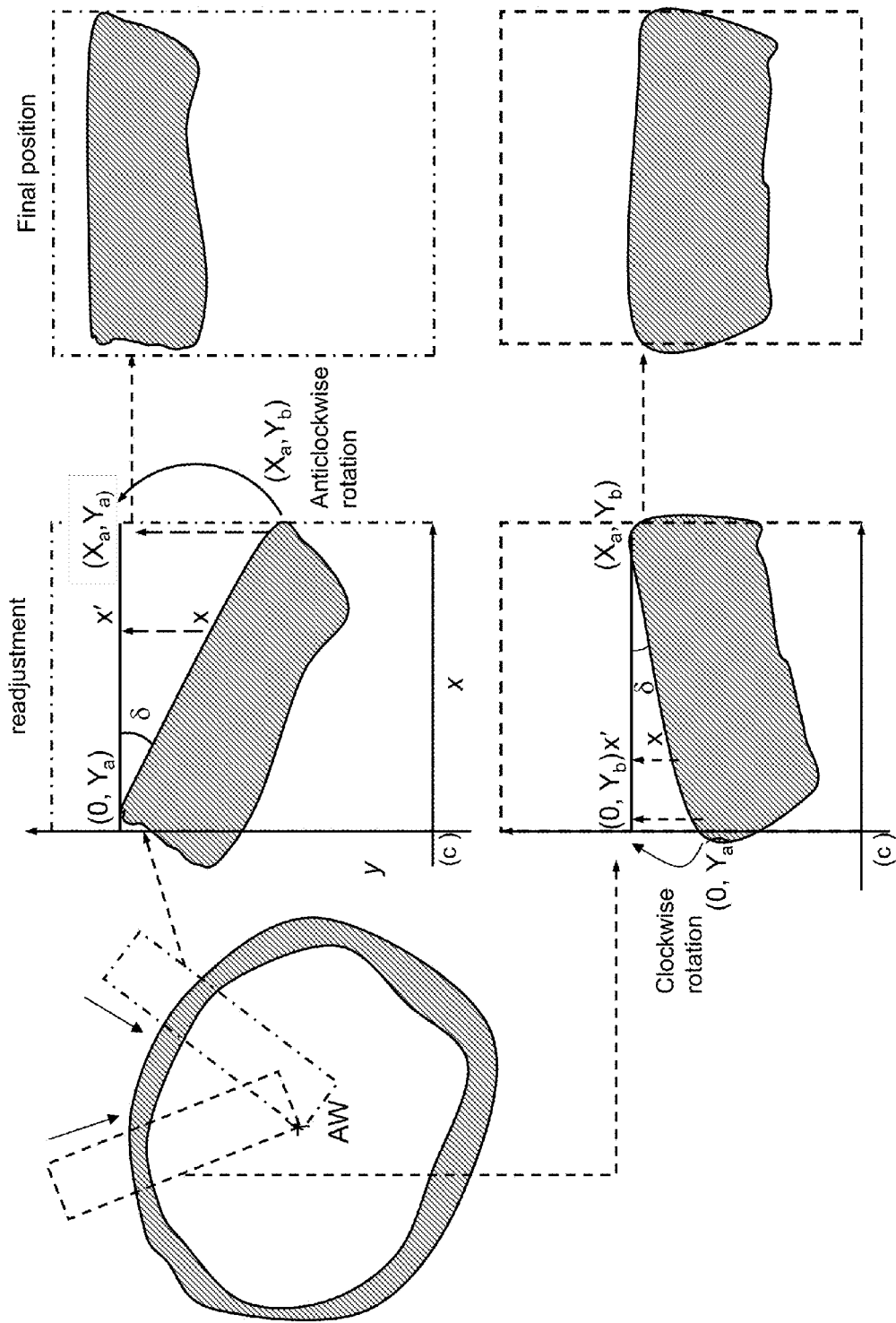
FIG. 7B is a schematic depiction of the rotation of an image of a bone sample by the image processor of the system of FIG. 1, both clockwise and anticlockwise.

Referring to FIG. 7B (top register), if an anticlockwise rotation is to be performed, the beginning of the bone at the first column (i.e. x=0) starts after the beginning of the bone at the last column ($X_a$). Image processor 16 detects the beginning of the cortex at the first column $(0, Y_a)$ and the beginning of the cortex at the last column $(X_a, Y_b)$ and determines that $Y_a > Y_b$; image processor 16 then determines the angle δ, between the sample and the horizontal, as:

$$\delta = a\tan((Y_a - Y_b)/X_a).$$

It should be noted that $X_a = AW$.

Next, image processor 16 uses δ to calculate the number of pixels (n) by which each column $x_i$ between 0 and $X_a$ needs to be rotated so that the specimen is horizontal as:

$$n = x_i \cos(\delta).$$

All columns are then moved anticlockwise by n pixels.

It should be noted that, because image processor 16 deals with small values of AW (i.e. relative to the radius of the bone), viz. less than 3 mm, the angle δ is so small that a $\tan(\delta) \sim \delta$ and the number (n) of pixels by which each column x needs to be rotated clockwise and anticlockwise is approximated as:

$$n = x_i * (Y_a - Y_b)/AW$$

where $x_i$ is the ith column.

Referring to FIG. 7B (bottom register), if a clockwise rotation is to be performed, the beginning of the cortex at the first column (i.e. x=0) starts after the beginning of the cortex at the last column ($X_a$). Image processor 16 detects the beginning of the cortex at the first $(0, Y_a)$ and the beginning of the cortex at the last column $(X_a, Y_b)$ and determines that $Y_a < Y_b$. Next, image processor 16 determines angle δ between the sample and the horizontal as:

$$\delta = a\tan((Y_a - Y_b)/X_a).$$

Using δ image processor 16 then calculates the number of pixels (n) by which each column $x_i$ between 0 and $X_a$ needs to be rotated so that the specimen is horizontal as:

$$n = x_i \cos(\delta).$$

All columns are moved anticlockwise by n pixels

Figure 8A:
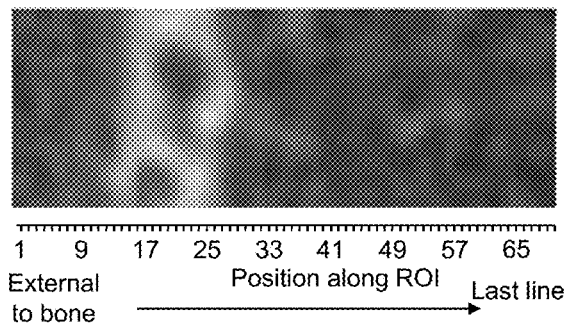
FIG. 8A is an exemplary image derived by the image processor of the system of FIG. 1 from a DICOM file of a region of interest (ROI)
Figure 8B:
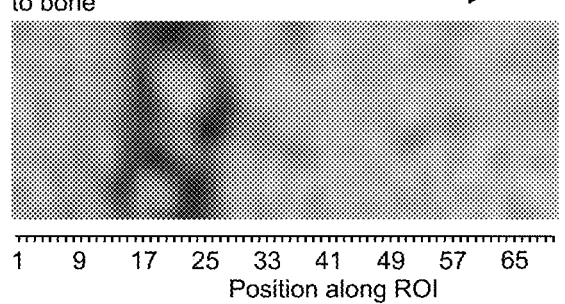
FIG. 8B is the image of FIG. 8A shown in negative for additional clarity.

Image processor 16 then analyses the density profile strip by strip. A strip is a rectangular section of the length of the ROI (i.e. AW, such as $AW_1$ or $AW_2$) and of the width of one voxel (or pixel). (Image processor 16 is also controllable to modify the characteristics of the strip). FIG. 8A is an exemplary image derived from a DICOM file from CT scanner 12 of a ROI, with the individual lines constituting the image labelled from 1 (in fact outside the bone sample) to 70 (within the bone). FIG. 8B is the same imagine in negative, for clarity.

After performing the adequate rotation to adjust the position of the ROI, image processor 16 then computes a density profile within the ROI. The type of density profile computed depends on the purpose of the analysis. Depending on the analysis, a profile of maximal, minimal or median values per strip may be computed. However, in most cases, image processor 16 computes a profile of mean values per strip. (For example, the profile of maximal values may be computed by image processor 16 when it is desired to separate two or more bones within an image. Furthermore, in alternative embodiments it may be desired to control image processor 16 to calculate, for example, the average square of all values in defining a profile.) An example of density profile determination and analyses is described below for the case of mean values. (The same analysis would be performed if density profile of maximal values, for example, was computed).

Figure 9:
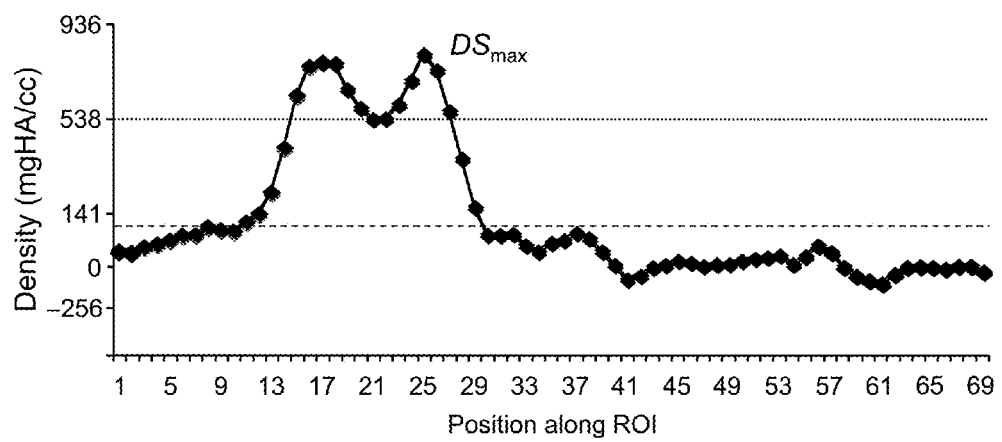
FIG. 9 is a plot of bone strip density (in mgHA/cc) against line number for the image of FIG. 8A as determined by the image processor of the system of FIG. 1.

Image processor 16 determines the mean density $DS_i$ of each strip i of bone as follows:

$$DS_i = \sum_{i=1}^{m} A_i/m \qquad (6)$$

where $A_i$ is the attenuation value of each voxel of the m voxels within strip i. A curve of the density profile is created using the mean density profile for each strip. Image processor 16 also identifies the strip with the maximum density ($DS_{max}$) within the entire curve. (At the voxel or pixel level, the words density and attenuation may be used interchangeably.) FIG. 9 is a plot of bone strip density (in milligrams of hydroxyapatite per cubic centimeter or mgHA/cc) against strip or line number, for the image of FIG. 8A, with the location of maximum strip density $DS_{max}$ indicated.

Then, a first order (or quasi-) derivative of the density profile curve is calculated by computing the differences in densities between consecutives strips as follows:

$$\Delta DS_{i,i+1} = (DS_i - DS_{i+1})/DS_i. \qquad (7)$$

(This definition of derivative, it will be noted, is the negative of the conventional definition.) From this first order derivative, image processor 16 analyses the bone sample by characterizing the sample as comprising a series on 'hills' and 'valleys'. Hills correspond to the decreasing parts of the density profile curve (i.e. where the first order derivative, as defined in equation 7, is positive) and valleys correspond to the increasing parts of the density profile curve (where this first derivative is negative). The derivative has the value 0 at the junctions of the hills and valleys.

Figure 10:
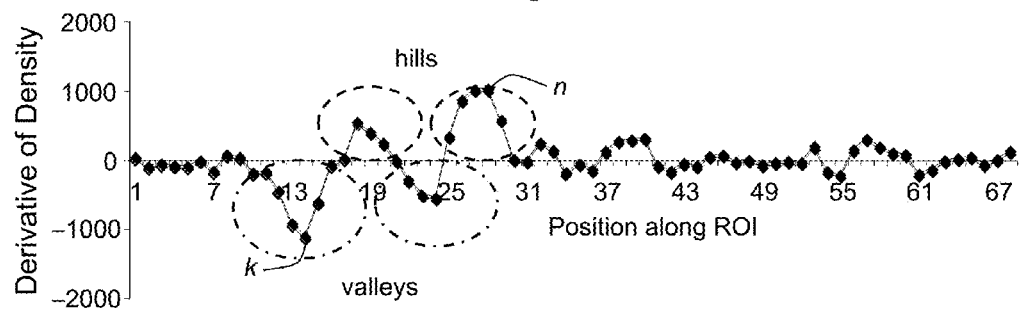
FIG. 10 is a plot of the first derivative of the density profile curve of FIG. 9, as determined by the image processor of the system of FIG. 1.

The derivative of the density profile curve of FIG. 9, as determined by image processor 16, is plotted in FIG. 10. Image processor 16 determines the 'heights' of the hills as the difference between the density of the top of the hill and the density at the bottom of the hill. Image processor 16 determines the 'heights' of the valleys as the difference between the density at the end of valley and the density at the beginning of the valley, the opposite of the calculation for hills. That is, hills are calculated as 1-0 (the density corresponding to 1 before the series of 0 values minus the density corresponding to the last 0 in the series), whereas the valleys are 0-1 (the density corresponding to 0 before the series of 1 values minus the density corresponding to the last 1 in the series). Using these hills and valleys, image processor 16 identifies key points in the attenuation profile using the following method, such as the highest peaks and troughs in the density profile curve within the cortical mass.

Image processor 16 then identifies the periosteal boundary j (i.e. where the bone begins). The density profile curve is retrieved from the matrix and provided with a new referential of centre $P_1$ (cf. FIG. 11). $P_1$ has a horizontal coordinate equal to that of $DS_{max}$ (determined from the derivative of the density shown in FIG. 10) and a vertical coordinate equal to minimum density external to $DS_{max}$. In this reference frame, a function $\lambda_1(N_i)$—being the distance function from $P_1$ to the density profile curve—is determined as follows:

$$\lambda_1(N_i(x_i,y_i)) = \sqrt{x_i^2 + y_i^2}.$$

where $N_i$ refers to strips between the first strip in the density profile and $DS_{max}$ (i.e. the strip with the maximum attenuation). The point j corresponds to the minimum value of $\lambda_1$.

Figure 11:
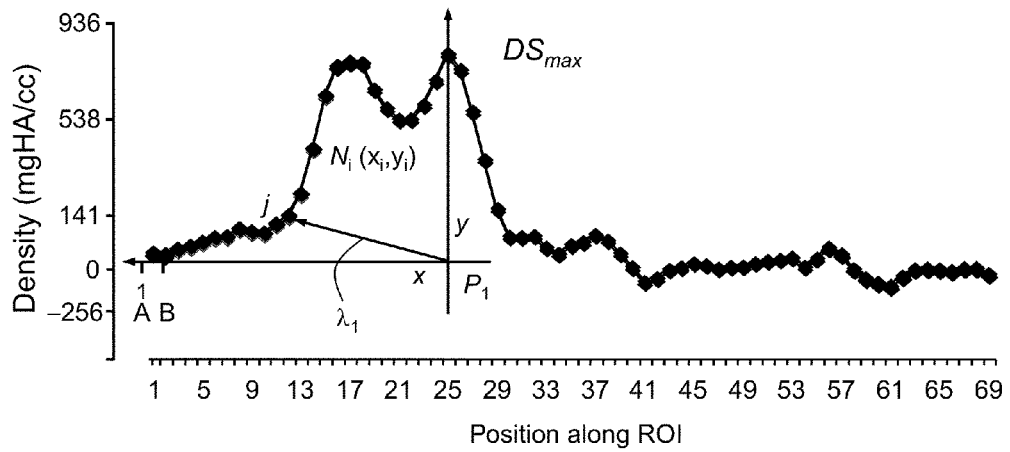
FIG. 11 is a plot comparable to that of FIG. 9, illustrating the determination of the periosteal boundary by the image processor of the system of FIG. 1.

FIG. 11 is a plot comparable to that of FIG. 9, but illustrating this step.

Image processor 16 then identifies the beginning of the cortex by examining the valleys in the first derivative of density (see FIG. 10) between j and $DS_{max}$; the beginning of the cortex k is the minimal value of the first order derivative in the highest (or deepest) valley between J and $DS_{max}$. This point is indicated at point k FIG. 10.

Next, image processor 16 identifies the beginning of the compact cortex (l), determined as the minimum of the function $\lambda_2$:

$$\lambda_2(N_i(x_i,y_i)) = \sqrt{x_i^2 + y_i^2}.$$

Figure 12:
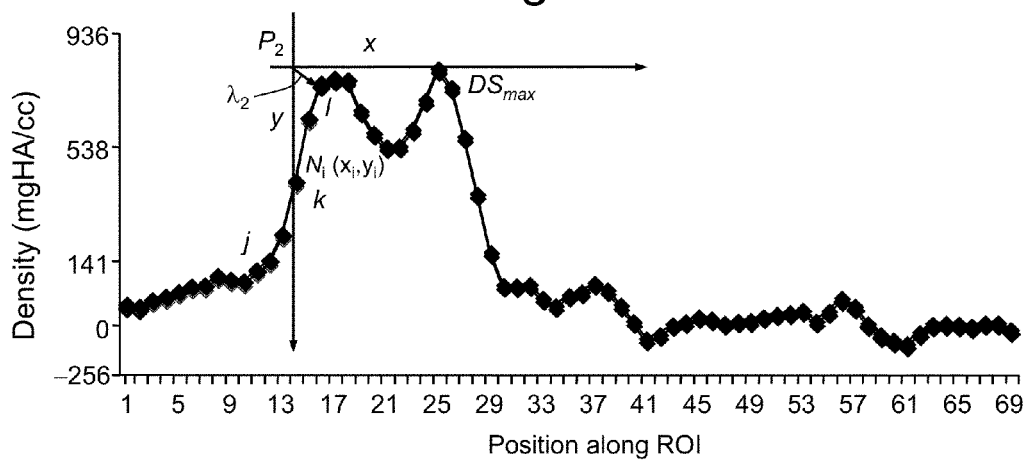
FIG. 12 is a plot comparable to that of FIG. 9, illustrating the determination of the beginning of the compact cortex by the image processor of the system of FIG. 1.

This step is illustrated in FIG. 12. Identifying l this way allows the elimination of artefacts such as an eventual local non-linearity of the periosteum or partial volume effects. In the identification of l, the density profile curve is reanalysed from a new referential of centre $P_2$, with $N_i$ limited to the strips between k (the beginning of the cortex) and $DS_{max}$.

It will be noted that $\lambda_2$ is identical in form with $\lambda_1$. They differ (as do $\lambda_3$ and $\lambda_4$ discussed below) by the referential point from which they operate and the portion of the density profile curve to which they are applied.

Figure 13:
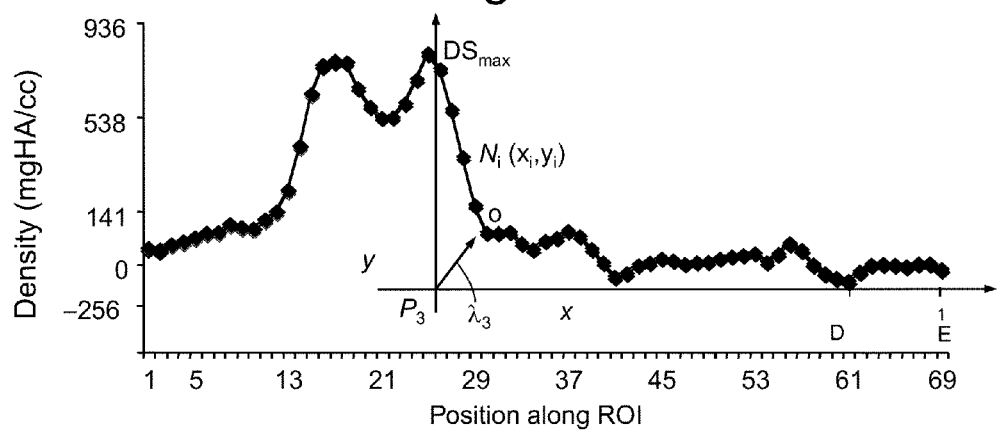
FIG. 13 is a plot comparable to that of FIG. 9, illustrating the determination of the end of the cortical mass by the image processor of the system of FIG. 1.

As illustrated in FIG. 13, image processor 16 identifies the end of the cortical mass (o) (and hence the beginning of trabecular bone), defined as the minimal value of the function $\lambda_3$:

$$\lambda_3(N_i(x_i,y_i)) = \sqrt{x_i^2 + y_i^2}.$$

To identify o, the density profile curve is reanalysed from a new referential of centre $P_3$, with $N_i$ limited to the strips between $DS_{max}$ and z (the end of the curve, corresponding to the end of the ROI). It will be appreciated by the skilled person that the order in which these points are determined is not according to their order in the density profile curve but rather according to the order in which they are needed for subsequent steps. This is why o, for example, is determined before points m and n (see below).

Next, image processor 16 identifies the end of the trabecularised cortex n, by identifying the maximal value of the first derivative in the highest hill between $DS_{max}$ and o. This point is indicated at point n in FIG. 10.

Figure 14:
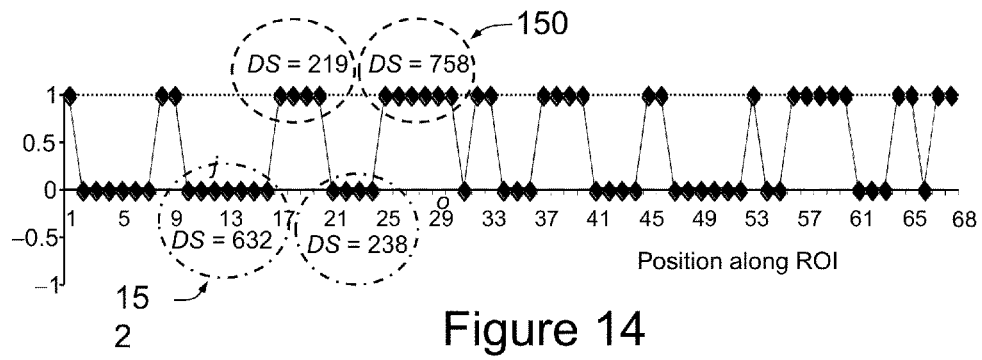
FIG. 14 is a plot of the first order derivative data of FIG. 10, binarized by the image processor of the system of FIG. 1, for determining the beginning and the end of the cortex.

To facilitate the identification of k and n, image processor 16 may 'binarizes' the first order derivative of the density (as shown, for example, in FIG. 10); the result of this binarization is plotted in FIG. 14. This facilitates the determination of the greatest of the hills and valleys within the cortical mass (i.e. between points j and o), which are indicated at 150 and 152 respectively. (The value of the density of each of the valleys and hills is shown in units of mgHA/cc.)

Figure 15:
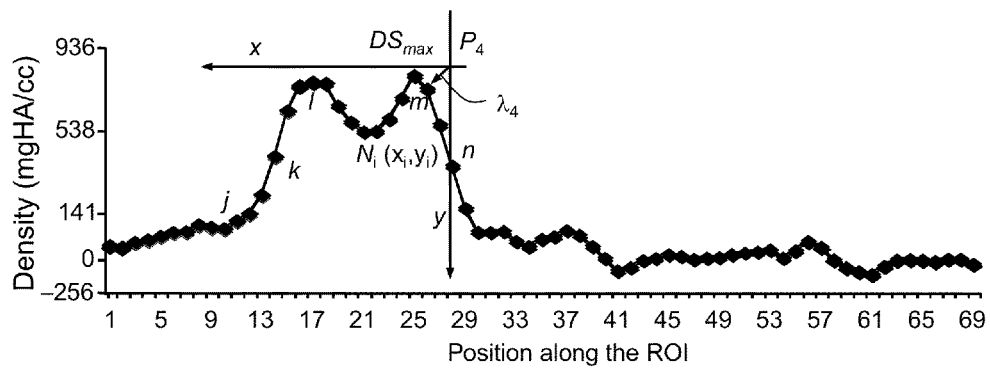
FIG. 15 is a plot comparable to that of FIG. 9, illustrating the determination of the end of the compact cortex by the image processor of the system of FIG. 1.

Image processor 16 identifies the end of the compact cortex (m), determined as the minimum of the function $\lambda_4$ (as illustrated in FIG. 15):

$$\lambda_4(N_i(x_i,y_i)) = \sqrt{x_i^2 + y_i^2}.$$

In identifying m, the density profile curve is reanalysed from a new referential of centre $P_4$, with $N_i$ limited to the strips between $DS_{max}$ and n (the end the trabecularized cortex).

Figure 16:
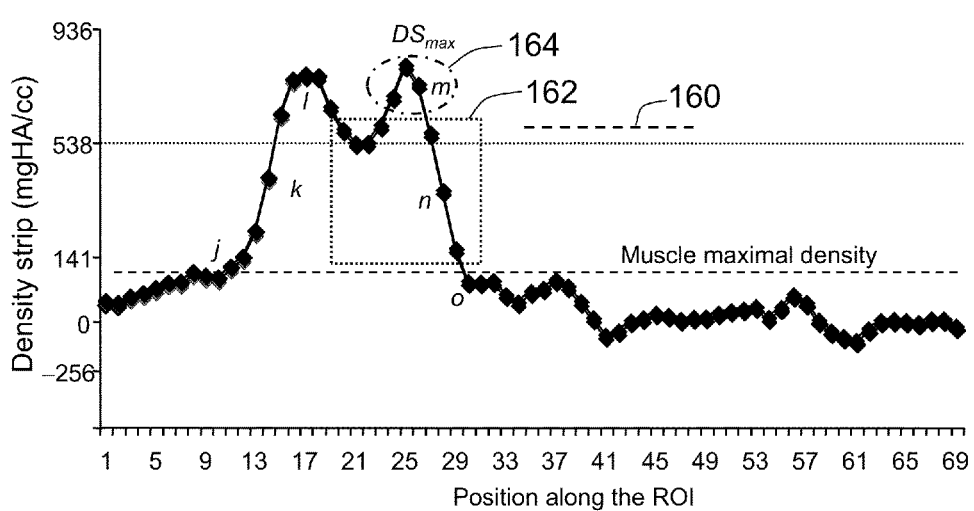
FIG. 16 is a plot comparable to FIG. 9, summarizing the results of the identification steps performed by the image processor of the system of FIG. 1.

FIG. 16 summarizes the results of these identification steps performed by image processor 16. Referring to FIG. 16, image processor 16 has by this point identified in the density profile (reading from left to right in the figure):

j: beginning of the bone (i.e. the periosteal boundary);

k: the beginning of the cortex;

l: the beginning of the compact cortex;

m: the end of the compact cortex;

n: the end of the trabecularised cortex; and o: the end of the cortical mass (and hence the beginning of trabecular bone.

Once these points are defined, image processor 16 resolves the bone into four compartments:

(i) The compact (or 'hard') cortex: between l and m;

(ii) The trabecularized cortex: between m and n;

(iii) The cortico-trabecular junction: between n and o; and (iv) Trabecular bone between o and the end of the sample (z).

Figure 17:
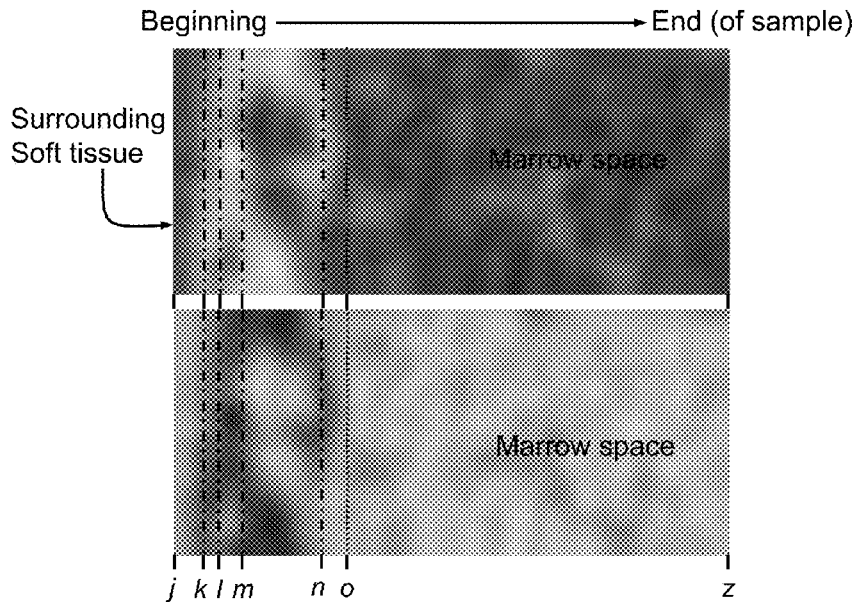
FIG. 17 is another exemplary image derived by the image processor of the system of FIG. 1 from a DICOM file of a region of interest (upper register) and a copy of this image shown in negative for additional clarity (lower register), with compartment boundaries identified by the image processor of the system of FIG. 1 labelled.
Figure 18:
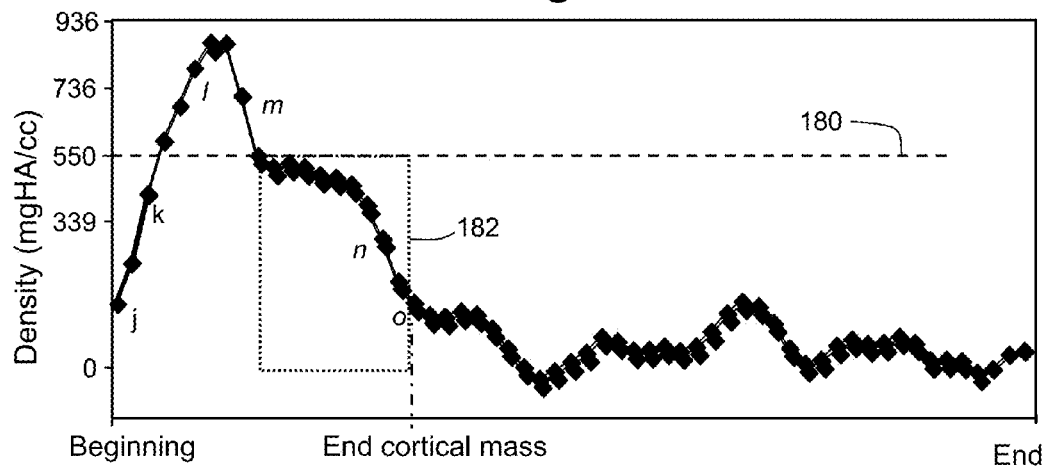
FIG. 18 is a plot of bone strip density (in mgHA/cc) against line number for the image of FIG. 17 as determined by the image processor of the system of FIG. 1.

FIGS. 17 and 18 present another example of an image and density curve determined by image processor 16. FIG. 17 includes the image (upper register) and—for clarity—negative of the image (lower register). FIG. 18 is a plot of the determined density curve, with the Current threshold of separation between cortical and trabecular bone indicated at 180. Compartment boundaries, as determined by image processor 16, are indicated for both the image and the density curve in these figures.

Figure 19:
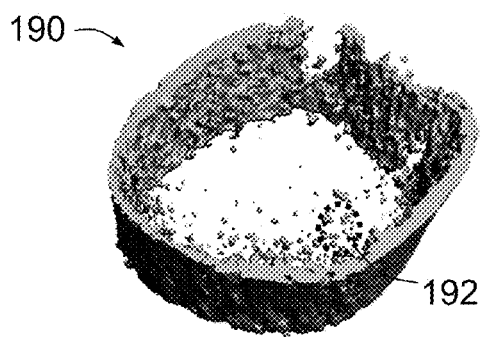
FIG. 19 is an exemplary image of a bone sample with 'floating cortical' bone identified with the system of FIG. 1.

The analytic segmentation (i.e. separation) of bone has the advantage of not relying on the use of thresholds. For example, in existing systems a threshold of 550 to 560 mgHA/cc is used to separate cortical from trabecular mass (Sharmilla). The approximate position of this threshold is indicated in FIG. 16 at 160; hence, after the initial rise in density, existing techniques will deem all bone internal to the point where the density subsequently drops below this threshold to constitute trabecular bone. In this example, the bone mass contained in box 162, though identified as cortical mass by image processor 16, would thus be identified incorrectly as trabecular mass by existing methods (even though in this example essentially no trabeculae are seen, as is apparent from the absence of data points in the trabecular compartment with density greater than that of muscle density). The portion of cortex (indicated at 164) with density above 550 mgHA would be seen by existing approaches as floating bone in the marrow space (see 'floating cortical' bone 192 in bone image 190 in FIG. 19) after a threshold has been used to segment the bone into cortical and trabecular bone; this is an artefact of existing approaches created by threshold based segmentation of bone into cortical and trabecular compartments. Furthermore, existing approaches would also fail to identify the large pore visible in the centre of the cortex of this example, hence producing an incorrectly low value for the sample's cortical porosity. Furthermore, existing approaches would underestimate the decay that has occurred in the trabecular compartment as they will incorrectly identify cortical bone as trabecular bone, when trabecular bone has indeed been lost, leading to an incorrect (and in fact an excessively low) estimate of trabecular bone loss. Image processor 16 avoids these pitfalls.

Box 182 in FIG. 18 illustrates another case where most of the cortex and its porosity is missed and erroneously labelled as trabecular bone.

Image processor 16 then rotates the image anti-clockwise and performs the same analysis in all the ROIs within the cross section (or slice). The number n of ROIs is a function of the rotation angle ($\theta$ in degrees) as:

$$n=360/\theta. \quad (8)$$

Figure 20A:
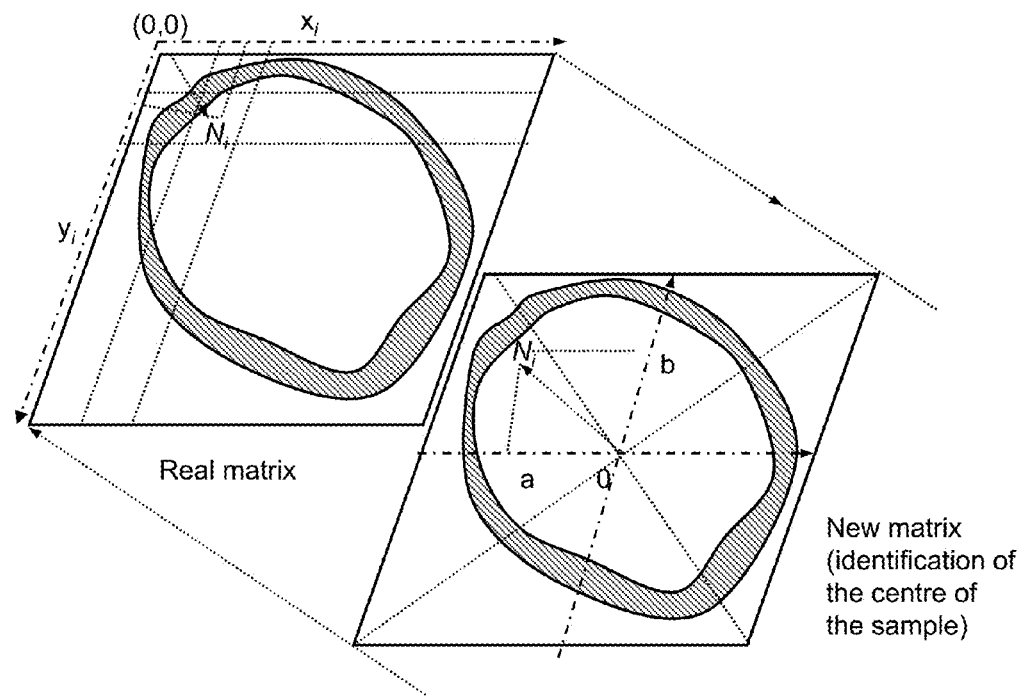
FIGS. 20A and 20B illustrate the preparatory steps performed by the image processor of the system of FIG. 1 for rotating a region of interest within an image.
Figure 20B:
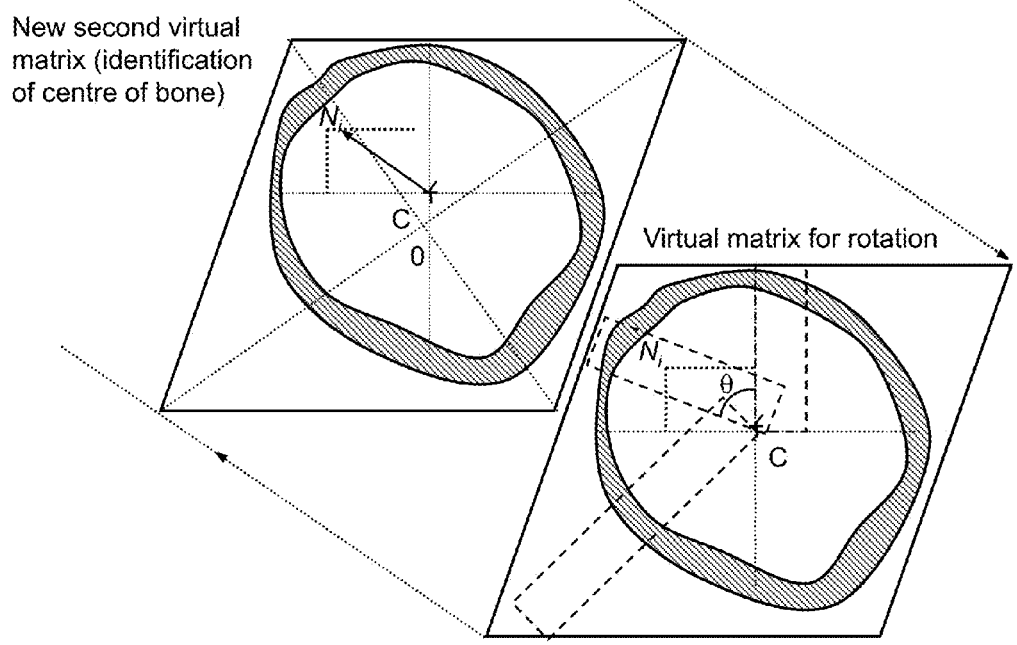

The method for rotating from $ROI_1$ to $ROI_n$ is performed by image processor 16 as follows (and as shown schematically in FIGS. 20A and 20B), for each slice At this point, image processor 16 creates a virtual mirror matrix (see FIG. 20B, lower register), which has the (x,y) coordinates of each pixel relative to the centre (G or C) but no attenuation value. This virtual matrix is the rotation matrix. An initial region of interest ($ROI_1$) is then selected from this rotation matrix. It should be noted that $ROI_1$ is selected so that its length is half that of the longest diagonal, so that no point with an attenuation value in the initial matrix is lost during the rotation process. Image processor 16 then retrieves the attenuation value of each point (or pixel) in the virtual matrix corresponding to $ROI_1$ from the initial matrix.

Image processor 16 then rotates each point A(x,y) in $ROI_1$ of this virtual matrix to A'(x',y') according to:

$$x' = x\cos\theta + y\cos\left(\theta + \frac{\pi}{2}\right)$$

and $$y' = x\sin\theta + y\sin\left(\theta + \frac{\pi}{2}\right).$$

Once rotated, the attenuation value of pixel A' is retrieved from the initial matrix. Image processor 16 rotates the whole initial ROI ($ROI_1$) at the same time. Image processor 16 rotates every points in the initial $ROI_1$ and repopulates a matrix similar in width and length to $ROI_1$ until a full 360° has been performed. For example, for an angle $\theta$ of 5°, each cross section is analysed as 72 matrices or 72 ROIs. For an angle $\theta$ of 1.5°, the entire cross section is analysed as 240 matrices (or ROIs); for an angle $\theta$ of 0.1°, the entire cross section is analysed as 3600 matrices (or ROIs).

Image processor 16 then ignores any strips with points with no corresponding attenuation values in the initial matrix owing to a particularly long $ROI_i$.

After selecting the appropriate AW and angle ($\theta$), image processor 16 analyses the image by performing a variable number of rotations around the entire cross section. For most indices (such as porosities, mineralization and trabecular parameters), a minimum of two rotations is employed in the analysis of the image.

Figure 20C:
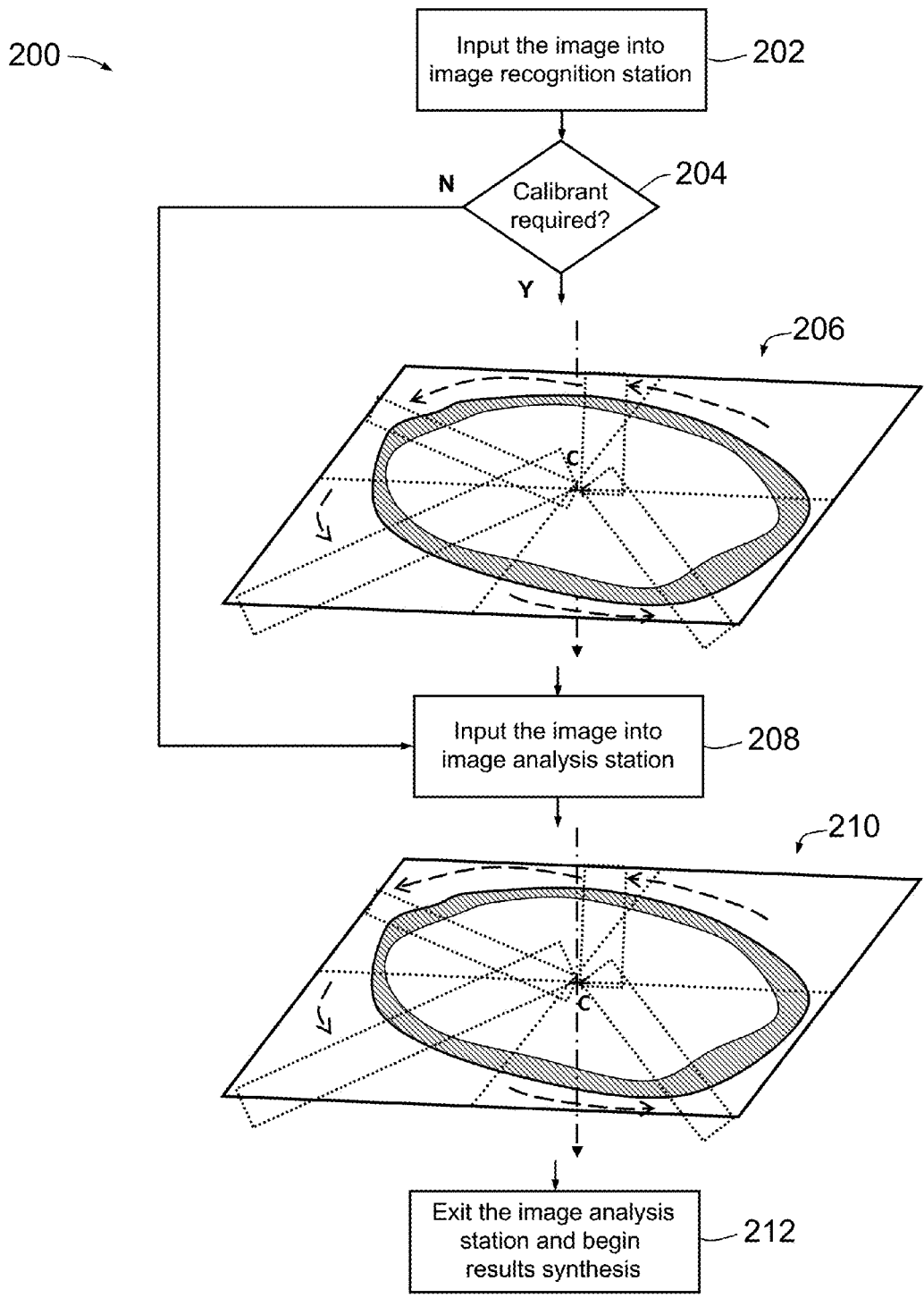
FIG. 20C is a flow diagram of the image recognition and image analysis rotations performed by the image processor of the system of FIG. 1.

FIG. 20C is a schematic flow diagram 200 of the operation of image recognition and image analysis stations of image processor 16. At step 202, the image is inputted by image processor 16 into the image recognition station.

At step 204, it is determined whether a calibrant is required. For the measurement of parameters (e.g. cortical thickness, external dimensions and internal dimensions) that do not require a calibrant such as the dimensions of the material, recognition rotations are not performed. Thus, if a calibrant is not required, processing by image processor 16 passes to step 208 (see below); otherwise, processing continues at step 206.

At step 206, one or more 'recognition' rotations—as many as required—are performed, to identify characteristics or features within the image that will be used in subsequent rotations for a detailed quantitative analysis. These features include one or more representative densities of surrounding soft tissue and one or more representative densities of the material of interest (in this example, bone) in the sample.

Thus, in the case of bone within an image, the objective of the recognition rotation(s) at step 206 is to (i) identify the surrounding background including the muscle tissue and retrieve a representative density of, say, the muscle tissue that will be used as calibrant in subsequent analysis rotations, and (ii) identify a representative density of material to be analysed, which will also be used subsequently in the quantitative analysis of the sample. Processing then passes to step 208.

At step 208, image processor 16 inputs the image into the image analysis station, to analyse and characterize the material of interest. At step 210, image processor 16 employs the image analysis station to perform one or more analysis rotations (as many as required) to analyze the sample. During the analysis rotation(s) at step 210, image processor 16 uses the characteristics retrieved during the image recognition rotations (see step 206), in this example bone, to quantify the parameters as described above.

At step 212, image processor 16 exits the image analysis station and begins results synthesis.

The analysis performed by image processor 16 exploits differences in density from one strip to the next within a compartment, so any compartment (viz. compact cortex, trabecularized cortex, cortico-trabecular junction and trabecular bone) limited to one strip is unsuitable for this analysis as, in this example, porosity, decay, etc., cannot be determined by image process 16. In addition, a compartment limited to one strip is unanalysable because the confounding effect of partial volume effects (PVE) on this strip cannot be assessed. Hence, image processor 16 does not analyse compartments limited to one strip.

Image processor 16 views a cortical mass of four strips (or indeed fewer) as unsuitable for analysis: the three intracortical compartments will have only one strip (which are hence each unanalysable) and the last or fourth strip may be tainted by PVE.

However, regardless of the number of strips within the cortical mass, image process 16 approximates the thickness of cortex (CThcm) as follows:

$$CTHcm = \frac{(n-1)*re + (DS_n * re)}{DS_{max}},$$

where n is the number of strips within the cortical mass, re is the resolution, $DS_n$ and $DS_{max}$ the densities of the last strip n and the density of the strip with the maximal density in the adjacent suitable $ROI_{i-1}$ or $ROI_{i+1}$. (If both ROIs $ROI_{i-1}$ and $ROI_{i+1}$ are suitable, the $DS_{max}$ is retrieved from the ROI with highest $DS_{max}$). It is assumed here, that last strip (n) is tainted by PVE.

In addition, internal and external radii are perimeters can be calculated as the beginning of the bone can be identified and the thickness of the cortex can be approximated.

Using this approach, image processor 16 selects and analyses n ROIs of the same width as $ROI_1$. Once all the ROIs within the slice have been analysed, image processor 16, then merges the n ROIs to reconstruct the analysed slice that has the characteristics required for the recognition or the diagnosis.

It should be noted that, during the rotation step, ROIs of interest overlap; that is, a pixel (i) may appear in more than one ROI. For example, at the distal tibia, for an angle θ of 0.1°, the cross section is reconstructed with 3600 ROIs and the same point may appear in as many as 90 ROIs. When this is so, image processor 16 takes into consideration (such as by tracing back a point in the ROIs to the same point in the original matrix) the contribution of overlapping points to each specific parameter, as it is important that the contribution of each pixel should counted only once. Image processor 16 counts and stores the number of times a point appears in a specific zone (viz. compact cortex, trabecularized cortex or trabecular bone) in different ROIs. During the merging process, image processor 16 first determines the frequency distribution of the appearance of the point in different zones, then attributes the point to the zone in which it appears most frequently (though other criteria may be used to determine the correct or most appropriate zone).

After reconstructing the first slice, image processor 16 advances to the next slice until all slices or all the preselected slices have been analysed. When all the slices have been analysed image processor 16 determines various parameters and outputs the relevant ones for the individual sample.

Image processor 16 allows a very broad investigation of bone and its surrounding tissues (typically comprising muscle and fat). The application of image processor 16 is not limited to indices relevant to the detection of osteoporosis. Indices produced relevant to many other metabolic diseases and infiltrative bone diseases such bone metastasis. Image processor 16 is controllable by the user to choose the indices the user desires, and to perform the chosen analysis promptly.

Cortical areas and thicknesses are determined by image processor 16 from the geometric centre C, with the arm width $AW_1$ and the rotatory angle $\theta_1$. These indices, when output, are displayed in units of millimeters or centimeters (for thicknesses) and mm² or cm² (for surfaces).

The average of the cortical thicknesses of the compact cortex ($CTh_{cc}$) is analogous to the mean CTh provided by existing QCT techniques, but is determined differently. According to this embodiment, image processor 16 determines a true average according to:

$$\sum_{i=1}^{n} CTh_i / n, \qquad (9)$$

where n is the number of ROIs analysed for the individual, that is, the mean of all CThs values (cf. current QCT techniques, which determines an estimate of the mean computed as Cortical area/Cross sectional perimeter).

The value determined by image processor 16 is the average of the 72 regions (or more) analysed in n slices. Image processor 16 allows the user to output the standard deviation (SD) and standard error of the mean (SEM) and the range for this value. Hence, the outputs are the average CTh, SD, SEM.

The median value of cortical thicknesses of the compact cortex is not determined in existing approaches, but the present inventors have ascertained that median CTh provides a better prediction of bone strength as estimated with finite element analysis than the average Cth, so image processor 16 determines and outputs median CTh. Image processor 16 determines the median CTh as the median of all 72 (or more) ROIs×n slices measured values of CTh. Image processor 16 can also determines the range (viz. minimal and maximal values) of such median values.

The minimum value of cortical thicknesses of the compact cortex is not provided by existing QCT techniques, but the present inventors have concluded that it is likely to be useful in clinical and research settings. There is evidence that the minimal value of CTh within the cross section shows the greatest decrease with age and therefore is likely to provide a better indication of the fracture risk that the mean CTh (which is understandable from a biomechanical perspective, just as a chain breaks at its weakness link). Image processor 16 can also determine a mean, SD, SEM and range of values of the minimum value of cortical thicknesses of the compact cortex, and identify the anatomical location of the compact cortex (e.g. anterior, posterior, etc) (see the results summarized below).

The lower the area of the compact cortex (or 'cortical area'), the greater the risk of fracture. Cortical area (or CoA)

is determined by image processor 16 as the number of pixels within the compact cortex multiplied by the area of the pixels, hence:

$$CoA = n \cdot (re^2), \quad (10)$$

where n is the number of pixels within the compact cortex and re is the resolution of CT scanner 12 (or other scanner used to image the bone, such as a MRI scanner). This can also be determined from:

$$CoA = \sum_{i=1}^{i=360/\theta} ((\theta/360) * ((\pi * r_i^2) - (\pi * (r - CTh_i)^2))), \quad (11)$$

where i is the ROI, n is the number of ROIs examined, $CTh_i$ is the cortical thickness at $ROI_i$ and rotation angle $\theta$ and $r_i$ is the radius of the bone at the $ROI_i$ (determined as described below). Image processor 16 effectively divides the cross section into small arcs of radii of curvature $r_i$, allowing it to accurately determine areas of irregular cross section (such as bones). The mean, SD, SEM and range of CoA can then be determined for all the cross sections examined.

Image processor 16 is also configured to determine $CTh_{tc}$, the average of the cortical thicknesses (CTh) of the trabecularized cortex. ($CTh_{tc}$ is not determined in existing techniques.) $CTh_{tc}$ is indicative of bone loss and fracture risk independently of the average thickness of the compact cortex. A thicker trabecularized cortex indicates that more decay has occurred and is more fragile (even if the residual compact cortex apparently remains as thick as that of peers). This value is determined by image processor 16 using equation 10 or 11, but applied within the compact cortex.

Image processor 16 is configured to determine the median value of the cortical thicknesses (CTh) of the trabecularized cortex, which provides additional information on the status of the cortex above and beyond the average value, and to determine the maximum of the cortical thicknesses (CTh) of the transitional (or equivalently the trabecularized) cortex, which shows where the cortex is weakest.

Image processor 16 is also configured to determine a novel parameter, the area of the trabecularized cortex, which is the area occupied by the pixels within the trabecularized cortex. It should be interpreted differently from the area of the compact cortex (of which it is, in a sense, the complement): the greater the area of trabecularized cortex, the more the magnitude of cortical decay that has occurred and hence the greater the fragility. This value is determined by image processor 16 again using equation 10 or 11, but applied within the trabecularized cortex.

Image processor 16 is also configured to determine the novel index $CTh_{cm}$: the average of the cortical thicknesses (CTh) of the cortical mass. Existing approaches identify the cortical mass but only in the compact cortex. The thicker the cortical mass, the better it is. This is determined using equation 9, but applied to the compact mass.

Image processor 16 is configured to determine two other novel indices: the median value of cortical thicknesses of the cortical mass, and the minimal value of cortical thicknesses of the cortical mass and their respective anatomical locations (see the results summarized below). Existing approaches do not identify the cortical mass, being limited to the compact cortex. The greater the median value of the cortical mass, the stronger the bone, and the smaller the minimal value of the cortical mass, the weaker the bone.

Image processor 16 is also configured to determine the area of the cortical mass, as the lower the cortical area, the greater the risk of fracture. Cortical area is determined by image processor 16 according using equation 10 or 11, but applied within the compact mass.

Image processor 16 is also configured to determine the average of the cortical thicknesses (CTh) of the cortico-trabecular junction (represented as $CTh_{ctj}$), the median value of cortical thicknesses of the cortico-trabecular junction, and the minimum value of cortical thicknesses of the cortico-trabecular junction. These indices are of value as, while in healthy bones there is a clear differentiation between the cortical and the trabecular compartment so the cortico-trabecular junction is very small, with aging and decay the cortico-trabecular junction increases so is blurred.

Image processor 16 is similarly configured to determine the area of the cortico-trabecular junction, using equation 10 or 11, but applied within the cortico-trabecular junction.

Image processor 16 can determine the respective radii $r_i$ for each of the 72 or more ROIs defined as the length between the start of the cortex and (C), as follows:

$$r_i = (z - 1) \cdot re, \quad (12)$$

where $r_i$ is the radius at $ROI_i$ and re is the resolution of CT scanner 12.

Image processor 16 can also determine porosity and other related indices, such as the percentage compact cortex (PCC), which is the proportion of the cortex that has a compact or solid appearance, determined from the ratio of the thicknesses of the compact cortex to that of the cortical mass calculated as follows:

$$PCC = 100 \cdot CTh_{cc} / CTh_{cm}. \quad (13)$$

A small value of PCC indicates that the cortex has diminished owing, for example, to ageing. (Certain disease processes such as hyperparathyroidism may also be indicated).

Similarly, image processor 16 is configured to determine percentage trabecularized cortex (PTC), the proportion of the cortex that has a trabecular-like appearance and is calculated as follows:

$$PTC = 100 \cdot CTh_{tc} / CTh_{cm}. \quad (14)$$

A high PTC means that the cortex has diminished during ageing or disease, such that a greater proportion of the cortex resembles trabecular bone.

Image processor 16 is configured to determine percentage cortico-trabecular junction (PCTJ), the proportion of the cortex that is a transitional zone, as follows:

$$PCTJ = 100 \cdot CTh_{ctj} / CTh_{cm}. \quad (15)$$

Generally, the higher the porosity, the weaker the bone, so image processor 16 is configured to determine several porosity indices.

For example, image processor 16 is configured to determine the apparent porosity (which is sometimes referred to simply as the 'porosity', but which—as the skilled person will appreciate—should be distinguished from the absolute porosity) of the compact cortex (aPoCC). If there has been no increase in porosity, all the strips would have a similar density. Apparent porosity is therefore calculated as the ratio of (i) the area of a rectangle defined by $DS_{max}$ and the thickness of the cortex and (ii) the area under the density curve within the specific compartment of the cortex (cf. FIG. 16 for the boundaries l, m, n and o of the respective compartments). The apparent porosity of the compact cortex is thus determined according to:

$$aPoCC(\%) = 100 \frac{\left(\sum_{i=1}^{n}((DS_i + DS_{i+1})/2)\right)/(n-1)}{DS_{max}}, \quad (16)$$

where n is the number of strips within the cortex in the ROI. This is an approximation of the more general formulation:

$$aPoCC(\%) = \frac{\int_{X=1}^{N} DS(x) \cdot dx}{DS_{max} * (n-1)},$$

which reflects the fact that the analysis is based on the ratio of two areas and is not necessarily a point by point analysis. The more general formulation may be more suitable in other embodiments.

Image processor 16 is also configured to determine the porosity (again, actually apparent porosity) of the trabecularized cortex (aPoTC) (according to equation 16 but limited to the trabecularized cortex), of the cortical mass (aPoCM) (according to equation 16 but for the entire cortex), and of the trabecular compartment (aPoTB) (according to equation 16 but for the trabecular compartment).

Porosities (that is, 'absolute' rather than apparent porosities) are also determined by image processor 16. To quantify porosities, image processor 16 identifies the representative densities of the surrounding muscle tissue ($Max_{md}$) and a representative density A(x) of the material of the material of interest (i.e., bone in this instance)

To identify $Max_{md}$, a minimum of rotation is needed. From the first rotation, using $AW_3$, image processor 16 identifies the surrounding muscle tissue and retrieves the maximal density of the muscle tissue ($Max_{md}$). To do so image processor 16 determines the frequency distribution of the attenuation values of all the voxels corresponding to the surrounding muscle tissue. $Max_{md}$ correspond to the attenuation corresponding to the 95th percentile in the frequent distribution curve. The maximal values may be tainted by noise from, for example, Compton scattering. The value at the 95th percentile is large enough to be representative of the $Max_{md}$ but essentially untainted by noise.

Figure 21:
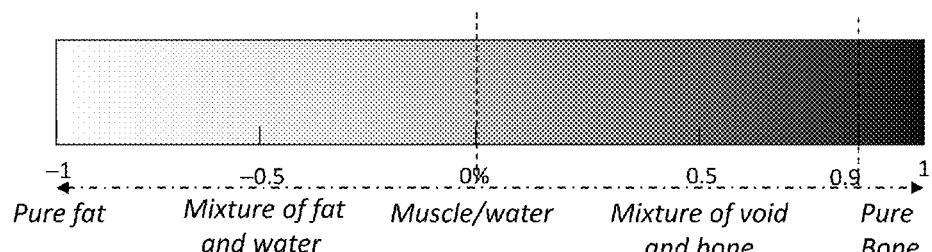
FIG. 21 is a BVE scale used by image processor of the system of FIG. 1 to analyse and characterize the bone during the analysis rotation.

The same process is used by image processor 16 to identify (B) the value representative of pure bone. There is experimental evidence to suggest that the maximal density of each ROI fulfils these criteria. The inter-haversian distance exceeds 200 μm, so four haversian canals define a square area exceeding 4,0000 μm² where no pores are present. Hence, at a spatial resolution of 82 μm, up to six pixels that are not tainted by partial volume effects will be placed between haversian canals within the cortex. It can therefore be assumed that the pixel with the highest density within a given ROI in is indeed of these pixels and has the density of purely mineralised bone. Hence, for every imaging modality of 200 μm resolution or below, the attenuation of (B) is considered as made of purely mineralized bone, untainted by PVE. Image processor 16, then used the attenuation of (B) is then used in conjunction with $Max_{md}$ to convert the attenuation values of all the voxels or pixels with an image into an scale ranging from −1 to +1. This transformation is a new concept that allows the attenuation of each voxel to convert into the estimated amount of bone within each voxel. The transformed unit of each voxel is referred to as bone volume equivalent (BVE). FIG. 21 is a BVE scale used by image processor 16 to analyse and characterize the bone during the analysis rotation. Fat has a BVE of −1, water (corresponding, in bone, to cells, blood vessels and interstitial tissue, hence similar to the surrounding muscle tissue or water) has a BVE of 0, and pure bone as a BVE greater than or equal to 0.9. Any voxel with a BVE lower than 0.9 is partly (if BVE>0 but <0.9) or fully (if BVE≤0) made of void.

Image processor 16 calculates the BVE of a voxel (X) of coordinates (i,j) within the ROI as:

$$BVE(X) = \frac{(A(X) - A(Max_{md}))}{(A(B) - A(Max_{md}))},$$

where A(X), A(B) and A ($Max_{md}$) are respectively, the attenuation values of the voxels X, B and $Max_{md}$.

The concept of BVE allows image processor 16 to provide a particularly detailed characterization of the bone, including estimating porosity within the image due to pores of size below the nominal in plane resolution of the imaging modality.

When the image is captured by an imaging modality with an in-plane resolution of 200 μm or below, voxels with a BVE equal to or greater than 0.9 are voxels with purely mineralized bone (as differences in density or attenuation due differences in tissue mineralization do not exceed 10%). Hence, any voxel with a BVE between 0 and 0.9 contains a proportion of void. If the voxel is located within the cortical mass, this voxel contains a pore of size smaller than the resolution of modality (cf. FIG. 21).

Voxels with a BVE of 0 are voids of size similar to or greater than the resolution of the imaging modality.

Image processor 16 calculates the pore volume equivalent (PoVE) of each voxel from the BVEs as follows:
  if BVE(X)≤0, then PoVE(X)=1, and
  if BVE(X)>0, then PoVE(X)=1−BVE(X).

The void content of each voxel within the image is then estimated from the PoVE.

(iii) Image processor 16 then calculates the total PoVE (TPoVE) within the ROI as:

$$TPoVE = \sum_{x=1}^{n} PoVE(x).$$

(iv) Finally, image processor 16 calculates the porosity (Po) within the ROI as:

$$Po = 100 * \frac{TPoVE}{n},$$

where n is the number of voxels within the ROI.

By this procedure, the contribution of each voxel to porosity is accounted for by image processor 16 proportionally to estimated proportion of purely mineralised bone within the voxel using the voxel's density.

It should be noted the range of pores to be assessed can be selected by the user with user interface 18 of image processor 16. For example, pores with PoVE=0 (i.e. voxels that appear to be empty to within the resolution of system 10), or pores with PoVE=0.5 (i.e. pores of half the size of the resolution of system 10).

The user can choose the quantify the porosity due to pores of any size within any of the three compartments of bone (i.e. compact cortex, trabecularized cortex and trabecular bone).

A method of quantification of pores of the size of the resolution of machine is as follows. Image processor 16 converts each pixel (or voxel) in each compartment into a binary value: bone '1' and non-bone '0', with bone defined as pixel i, such that:

$$A_i > \text{Max}_{md}, \tag{18}$$

and non-bone defined as pixel j, such that:

$$A_j \leq \text{Max}_{md}. \tag{19}$$

Figure 22A:
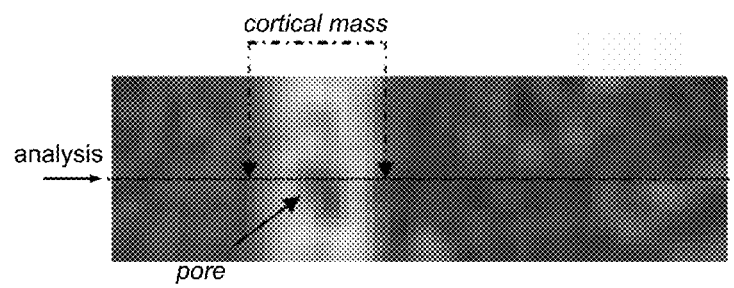
FIGS. 22A, 22B and 22C depict the process of image binarization performed by the image processor of the system of FIG. 1, where
Figure 22B:
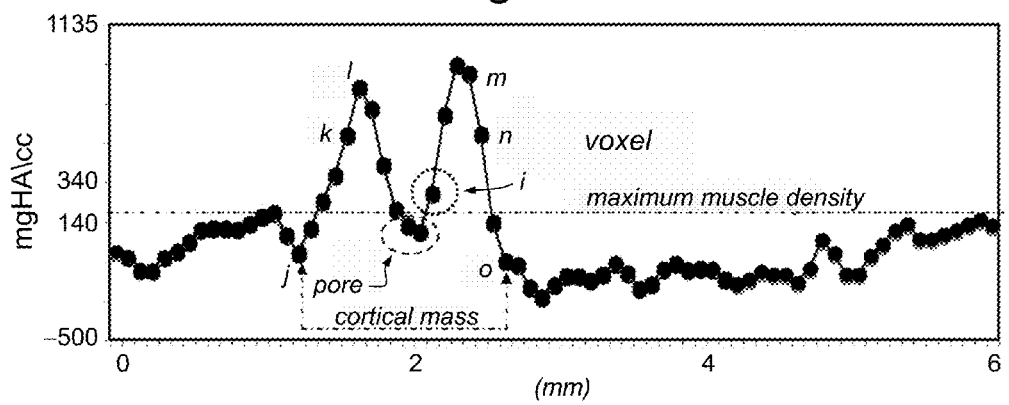
Figure 22C:
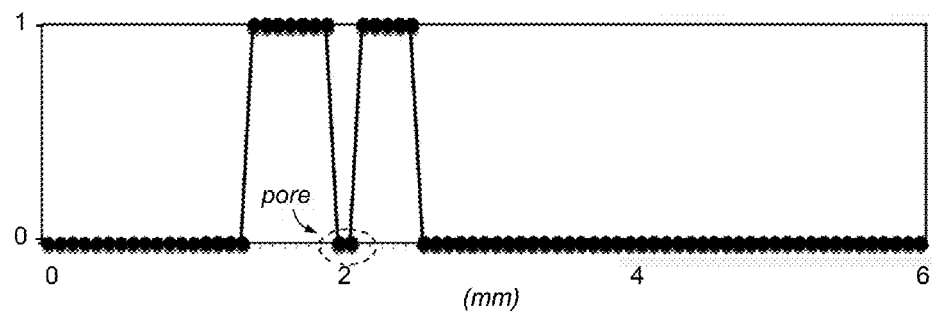

The result of this process is shown schematically in FIGS. 22A, 22B and 22C. FIG. 22A is an example of a ROI with a pore visible within the cortex. After identification of compartments, pores are defined as voxels with density inferior to $\text{Max}_{md}$. An example of the identification of pores within the cortical mass in one column is shown in FIG. 22B. FIG. 22C is a binarized plot of bone versus non-bone pixels along the line of analysis. Binarization and identification of pores occurs after the cortical mass has been identified in the analysis of the entire ROI.

Existing techniques for determining porosity use a dichotomous approach to distinguish pore from bone tissue, based on a fixed arbitrary threshold. Porosity so determined is highly resolution dependent and influenced by partial volume effects (PVE), so image processor 16 regards it merely as 'apparent porosity'. Voxels with variable proportion of bone and soft tissues at the edge of the pore—bone (i.e. tainted by PVE), such as point i (which is tainted by PVE) shown in FIG. 22B are erroneously excluded from the calculation of porosity. The same errors applies when current algorithms computes porosity after using a threshold to separate bone from soft tissues. This is why image processor 16 advantageously computes porosity as described (cf. equations 16 and 17) where the density of every voxel is accounted for.

Figure 23:
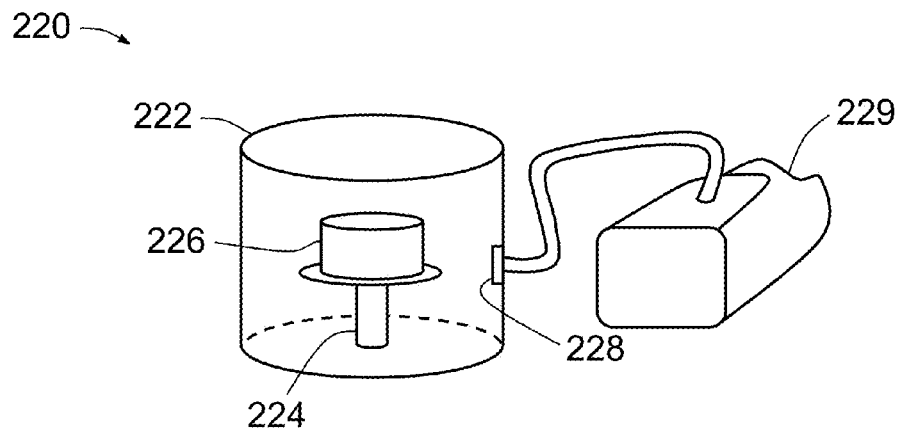
FIG. 23 is a flow diagram illustrating the use of the system of FIG. 1 to identify an object of known dimensions within an image, isolate and determine its dimensions.

It should be noted that the general principle embodied by image processor 16 is the determination of porosity by employing the surrounding environment and a representative density of material of interest in its pure form as referents. This enables image processor 16 readily to provide a non-destructive measurement of porosity of any material, not only bone. The porosity of materials (for example, rocks, metals and plastics) may be determined using a vacancy or 'emptiness' as a referent. This is illustrated, by way of example, in FIG. 23. FIG. 23 is a schematic view of a porosity measurement apparatus 220 for the non-destructive in vitro measurement of the porosity of materials, according to an embodiment of the present invention, for use in conjunction with system 10 of FIG. 1.

Apparatus 220 includes a sealable tube 222 with an internal station 224 (for supporting a material or sample to be analysed 226). Tube 222 has a valve 228, and apparatus 220 includes a vacuum pump 229 attached to valve 228. Vacuum pump 229 is provided for evacuating tube 222 once material or sample 226 is on station 224 and tube 222 has be sealed.

Thus, after mounting material or sample 226 on station 224 and sealing tube 222, vacuum pump 229 is switched on and any floating material around material or sample 226 is evacuated from tube 222 by vacuum pump 229. Thus, an at least partial vacuum is created around material or sample 226, which serves as the vacancy or 'emptiness' (of low or zero density) exploited according to the present embodiment. Tube 222 can then be detached from vacuum pump 229 and located within central scanning volume 24 of CT scanner 12, scanned, and the resulting data forwarded to image processor 16 for processing as described above.

Establishing this 'emptiness' (essentially a region of low density) around material or sample 226 allows image processor 16 to use the surrounding environment (in this case the so-called 'emptiness') to determine porosity within material or sample 226. A material floating or otherwise around material or sample 226 would otherwise be identified by image processor 16, which would use it as a referent, leading to inaccurate results. (Emptiness' is used in quotes to acknowledge that a truly zero pressure cannot be achieved, and in any event is not necessary; the removal of this 'floating debris' is sufficient.)

After impurities (e.g. this floating material) have been removed, the material of interest is imaged (CT) as described above. Images are automatically retrieved and analysed by image processor 16 to determine the absolute porosity using the surrounding environment (in this case 'emptiness') as referent as described above. The use of a referent (emptiness in the case of porosity) avoids the reliance on absolute CT-values.

In one embodiment, the invention provides an integrated porosity measurement system comprising system 10, sealable tube 222 and vacuum pump 229.

It should be noted that in the case of porosity quantification in a living person, pores are non-bone spaces within the bone envelope, rather this so-called 'emptiness'. These non-bone spaces are occupied by tissues of density equal or inferior to that of the muscle. This why assessment of porosity in bones, in living individuals (in in vivo settings), uses muscle as referent.

Non-destructive measurement of porosity has many potential applications including material characterization, detection of internal flaws and cracks within the material.

It should be noted that image processor 16 can output this porosity, such as for comparative purposes. In this case, the pore area (PoA) in each compartment is:

$$PoA = \sum_{i=0}^{n} PoVE. \tag{20}$$

Image processor 16 then determines porosity in each compartment. For example the porosity of the compact cortex (PoCC) is:

$$PoCC = 100 * \frac{PoACC}{AreaCC}, \tag{21}$$

where PoCC is the porosity of the compact cortex, PoACC is the pore area of the compact cortex and AreaCC is the area of the compact cortex.

Image processor 16 is configured to determine the decay of the compact cortex (CD1). This index reflects a gradual increase in porosity from the inner to the outer cortex as observed during ageing. Pores are uniformly distributed within the cortex of young healthy individuals, so—for them—that the line of best fit within the cortex is substantially horizontal. With ageing, porosity erodes the inner more than the outer aspect of the cortex, so the line of best fit lines makes an increasingly greater angle with the horizontal. A normal CD1 is less than 3.5%.

Image processor 16 determines CD1 by determining the line of best fit within the compact cortex using conventional least mean squares formulae, then determining the angle ($\omega_1$, in radians) between the line of best fit and the horizontal line passing through $DS_{max}$, and then determining CD1 as:

$$CD1(\%) = 100(\omega_1/1.5707). \quad (22)$$

Image processor 16 determines the decay of the trabecularized cortex (CD2), which is analogous to CD1. CD2 is calculated by determining the line of best fit within the end of the compact cortex (m) and the beginning of the trabecular bone using conventional least mean squares formulae, then determining the angle ($\omega_2$, in radians) between the line of best fit and the vertical line passing through m. CD2 is then determined as:

$$CD2(\%) = 100(\omega_2/1.5707). \quad$$

Image processor 16 can also determine cortical fragility (CF), which is indicative of—and hence allows the assessment of—the contribution of porosity due to high remodelling to cortical fragility. CF is determined as follows:

$$CF(\%) = (AbsPo_{cc} * CD_1 + AbsPo_{tc} * CD2)/10000. \quad (23)$$

Image processor 16 can also determine relative density, that is, the attenuation of a respective compartment (compact cortex, trabecularized cortex, etc) relative to that of the surrounding muscle. Relative density thus reflects both the mineralization and the porosity and is expressed as a percentage. Relative densities are independent of $DS_{max}$.

The average density (or attenuation) $DS_m$ of muscle strips is:

$$DS_m = \left(\sum_{i=1}^{k-1} DS_i/n\right). \quad (24)$$

The relative density of each compartment is then determined in a similar manner. For example, the relative density of the compact cortex is:

$$RD_{cc} = 100 \cdot DS_{cc}/DS_m, \quad (25)$$

where $DS_{cc}$ is the density of the compact cortex. A relative density thus indicates on average how dense the bone is compared to the surrounding tissues. The less mineralised is the bone, the less porous, and the lower is its relative density.

Likewise, the relative density of trabecularized cortex ($RD_{tc}$), that is, the ratio of the density of strips of the trabecularized cortex ($DS_{tb}$) to $DS_m$, is:

$$RD_{tc} = 100 \cdot DS_{tc}/DS_m.$$

The relative density of the cortical mass ($RD_{cm}$), that is, the ratio of the density of strips of the cortical mass ($DS_{cm}$) to $DS_m$, is:

$$RD_{cm} = 100 \cdot DS_{cm}/DS_m.$$

The relative density of the trabecular mass ($RD_{tb}$), that is, the ratio of the density of strips of the cortical mass ($DS_{tb}$) to $DS_m$, is:

$$RD_{tb} = 100 \cdot DS_{tb}/DS_m.$$

The cortico-trabecular differentiation index (CDTI) is the ratio of the area under the density profile curve in the trabecular bone compartments to the area under the density profile curve in the cortical mass compartments, as is determined by image processor 16 from:

$$CTDI = 100 \frac{\sum_{i=o+1}^{z}((DS_i + DS_{i+1})/2)}{\sum_{i=k}^{o}((DS_i + DS_{i+1})/2)}, \quad (26)$$

where k, o and z are respectively the strips corresponding to the beginning of the compact cortex, the end of the cortical mass and the end of the entire sample. It should be noted that, in largely cortical sites (such the midshaft of the femur or the subtrochanteric region) in young adults, the cortex is clearly distinct from the trabecular bone. In these sites, bone loss transforms the cortex into a inner trabecular-like structure and an therefore the differentiation between the cortex and the trabecular bone diminishes, thus decreases CTDI.

Image processor 16 is also configured to determine various fat indices. These indices reflect the extent of fat transformation of the bone marrow. The more the bone has been replaced by fat, the more bone has been lost and the greater the fragility of the bone. The attenuation in a compartment within the bone that is lower than the surrounding muscle (of representative density $Max_{md}$) reflects a loss of bone within that compartment and its replacement by fat. Fat voxels therefore constitute strips within the trabecular bone that have density less than the muscle density $Max_{md}$.

Image processor 16 is configured to determine fat proportion (FatP) (the number of fat voxels divided by the total number of examined voxels) and the fat burden (FatB) (the average density of fat voxels (FS) compared to the representative density of muscle, $Max_{md}$). The average density ($DS_f$) of fat strips is:

$$DS_f = \sum_{i=1}^{n}(D_i)/n, \quad (27)$$

where $D_i$ is the density of voxel i and $D_i \leq Max_{md}$. The fat burden (FatB) is therefore:

$$FB(\%) = 100(DS_f/Max_{md}). \quad (28)$$

Image processor 16 is also configured to determine various mineralization indices. These indices reflect the degree of mineralization and the heterogeneity in the distribution of the mineralization. It is assumed that the difference in the attenuation between the bone pixel with the maximal density and the muscle ($Max_{md}$), which is the contrast between these two tissues, reflects the level of mineralization of the bone. This index is not calculated using strips but bands. Image processor 16 identifies pixels or voxels that are almost certainly entirely made of purely mineralised bone and hence, minimally tainted by partial volume effects and porosity. These are voxels with a BVE equal to or greater than 0.9, as discussed above. The mineralization (ML) level is determined after examining all the cross sections within the image, not at ROI.

Image processor 16 determines ML as:

$$ML(\%) = 100 * \frac{\frac{1}{n}\sum_{i=1}^{n}((A(i) - (A(Max_{md}))}{A(B)}, \quad (29)$$

where A(i) is the attenuation of the pixel or voxel (i) such that BVE(i)>0.9.

When desired, image processor 16 can determine and output the absolute densities of the compact cortex, trabecularized cortex, cortico-trabecular junction and trabecular bone in mgHA/cc (HA=hydroxyapatite) or mg/cc of mineralised bone, as required by the user.

Image processor 16 converts the attenuation of each voxel within a given compartment of the bone to mgHA/cc with the equation:

$$D \text{ (mgHA/cc)} = (695.808 * (A_i / \text{Max}_{md})) - 455.27, \quad (30)$$

where $A_i$ is the attenuation of voxel i. This equation was established experimentally by scanning phantoms.

Image processor 16 converts the attenuation A of each voxel within a given compartment into its equivalent of mineralised bone in g/cc, firstly by identifying the voxels associated with muscle and then using the muscle density as a referent to determine the density of bone. The need for daily calibration is avoided owing to the use of the subject's own muscle as a referent. The density (D) of other voxels in g/cc is then determined by image processor 16 from:

$$D \text{ (g/cc)} = 0.495 * (A / \text{Max}_{md}). \quad (31)$$

Purely mineralised bone has a density of 2.14 g/cc.

Image processor 16 outputs the absolute densities (in g/cc and mgHA/cc) of cortical and trabecular bone. This is for comparison only, as absolute densities are more commonly required.

Image processor 16 determines strength indices by using the centroid G, the rotatory arm width $AW_2$ and the rotation angle $\theta_2$. Non-bone tissue within the subperiosteal envelope is removed using $\text{Max}_{md}+1$ as discussed above. Image processor 16 then determines strength indices as follows.

Image processor 16 determines buckling ratios (BR) as follows for each ROI:

$$BR_i = CThcc_i / r_i. \quad (32)$$

where $CThcc_i$ and $r_i$ are respectively the thickness of the compact cortex and the radius at the $ROI_i$.

Image processor 16 determines the second moment area (or moment of inertia I) for all angles $\theta$ within the slice as follows:

$$I_x = \int_{i=1}^{n} y_i^2 (re^2), \quad (33a)$$

where $I_x$ is the second moment of area about the axis x, re is the resolution of the pixel, and $y_i$ is the perpendicular distance from the axis x to the element pixel.

Image processor 16 calculates the second moment area in all directions around the cross section. However, before calculating the moment of inertia, image processor 16 excludes any non-bone pixels from the image. Again, no threshold is used to identify non-bone pixels. Non-bone pixels are pixels of attenuation below that of the beginning of the bone (i.e. muscle or below). This exclusion of non-bone pixels (i.e. pores) allows image processor 16 to calculate I as free as possible from the effects of porosity.

The mass adjusted second moment area is calculated in a similar fashion to the moment of inertia, but with the density or attenuation of each pixel taken into account. The mass adjusted second moment area is thus determined as follows for each ROI:

$$I_{xma} = \int_{i=1}^{n} ((A_i)/A_{max}) * y_i^2 * (re^2), \quad (33b)$$

where $I_{xma}$ is the mass adjusted second moment area about the axis x, $A_i$ is the density (or attenuation) of each bone pixel and $A_{max}$ is the maximal attenuation of all pixels within the slice (i.e. the pixel almost certainly made of purely mineralised bone).

Image processor 16 determines the section modulus similarly to the determination of I in all directions, again excluding non-bone pixels, as follows:

$$Z_x = \frac{\int_{i=1}^{n} y_i^2 \cdot re^2}{\left(\int_{i=1}^{n} y_i\right)/n}. \quad (34)$$

Image processor 16 determines the mass adjusted section modulus similarly to the determination of I in all directions, again excluding non-bone pixels, as follows:

$$Z_{ma} = \frac{\int_{i=1}^{n} ((A_i)/A_{max}) * y_i^2 * re^2}{\left(\int_{i=1}^{n} y_i\right)/n}.$$

Image processor 16 determines the product moment of area, excluding non-bone tissue and not taking the angle into account (which is irrelevant in this case), as follows:

$$Ixy = \int_{i=1}^{n} x_i * y_i * re, \quad (35)$$

where x and y are the coordinates in a frame of reference with centre G as defined by bone pixels. The product moment of area is a determinant of bending stress in an asymmetric cross section. This is the case for most bone, which are asymmetric. Unlike the second moments of area, the product moment may give both negative and positive values. From this image processor 16 determines the maximum and minimum mass adjusted second moments area, as well as their orientation within the cross section.

Image processor 16 determines the mass adjusted product moment area after separating bone from non-bone pixels, and without taking the angle into account as it is again not needed. Image processor 16 determines the mass adjusted product moment area as follows:

$$S_{I_x} = \int_{i=1}^{n} (A_i)/A_{max}) * x_i * y_i * re, \quad (36)$$

where $A_{max}$ and $A_i$ are respectively the maximal attenuation and the attenuation of pixel i. x and y are the coordinates of each pixel i in a frame of reference with centre G. Image processor 16 then determines the maximum and minimum mass adjusted second moment area, as well as their orientation within the cross section.

Image processor 16 is configured to determine the polar moment of inertia J, which predicts the ability of the cross section to resist torsion, as follows:

$$J = \int_{i=1}^{i=n} (x^2 + y^2) * re^2. \tag{37}$$

Image processor 16 determines the polar moment of inertia for every angle, and also determines its maximum and minimum values.

Image processor 16 is configured to determine the mass adjusted polar moment of inertia $J_{max}$, as follows:

$$J_{max} = \int_{i=1}^{n} (A_i)/A_{max} * (x^2 + y^2) * re^2. \tag{38}$$

Image processor 16 is also configured to determine the total cross sectional area (TCSA) and perimeter. For these indices, image processor 16 uses the centroid G, the rotatory arm width $AW_2$ and the rotation angle $\theta_2$. Non-bone tissue within the subperiosteal envelope is removed using $Max_{md}$ as referent as described above.

For each $ROI_1$, image processor 16 computes the $L_{ROIi}$ (length of ROI) according to:

$$L_{ROIi} = \theta_2 * (2ri*\pi)/360. \tag{39}$$

After rotation by 360°, image processor 16 determines the total perimeter P of the cross section from:

$$P = \sum_{i=1}^{360/\theta_2} (\theta * (2r_i * \pi)/360). \tag{40}$$

Image processor 16 then determines the total cross section area (or periosteal area) TCSA as:

$$TCSA = \sum_{i=1}^{360/\theta_2} (\pi * r_i^2) * \theta_2/360. \tag{41}$$

Image processor 16 then determines the endocortical perimeter ECP as:

$$ECP = \sum_{i=1}^{360/\theta_2} (\theta_2 * (2(r_i - CThcc_i) * \pi)/360), \tag{42}$$

where $CThcc_i$ is the thickness of the compact cortex in $ROI_i$

Image processor 16 then determines the endocortical area ECA as:

$$ECA = \sum_{i=1}^{360/\theta_2} (\pi * ((r_i - CThcc_i)^2)) * \theta_2/360. \tag{43}$$

Image processor 16 then computes the ratio ECA/TCSA, which is an indicator of fragility.

Image processor 16 treats each ROI as an infinitesimal portion of a circle of radius $r_i$, allowing the determination of the areas and perimeter of structure of complex shape such as a bone cross section. This is why $AW_2$ is very small.

All non-bone tissue is removed from the trabecular compartment using $Max_{md}$ as referent so that, for any ROI, from strip o to z, only trabeculae are included. As discussed above, image processor 16 employs a rotatory arm width $AW_1$ and a rotatory angle $\theta_1$. (In fact the choice of AW here is of no great importance; any rotatory AW will suffice. As discussed above, image processor 16 has three AWs; $AW_1$ and $AW_2$ are rotatory in the sense that they can move from one ROI to another one, while $AW_3$ is static and only serves to assess muscle density at specific locations.)

After removal of non-bone tissue as explained above, all non-bone tissue pixels are given the value 0 and bone tissue pixels the value of 1. The width ($w_i$) for the n non-bone voids for each column i is determined as:

$$w_i = n*re, \tag{44}$$

where re is by the resolution of the scanner. Trabecular size ($Tr \cdot S_i$) for column i is calculated as:

$$Tr.S_i = \frac{((z-o)*re) - w_i}{m_i}, \tag{45}$$

where $m_i$ is the number of trabeculae. A trabecular bone is regarded as a series of consecutive pixels coded as 1. The presence of a '0' indicates the end of the trabecular.

Image processor 16 repeats this process for each line j, where the trabecular size for each line j is:

$$Tr.S_j = \frac{AW - w_j}{m_j}, \tag{46}$$

and where $m_j$ is the number of trabeculae in the j line. It should be noted that a column is a series of pixels in the direction of the density profile and a line is perpendicular to the column.

Finally, image processor 16 determines the Tr·S for the ROI from:

$$Tr.S = \left(\sum_{i=n}^{1} Tr.S_i + \sum_{j=1}^{n} Tr.S_j\right) / (m_i + m_j). \tag{47}$$

Image processor 16 determines and outputs this trabecular size, as this reflects both the shortening and the thinning of trabeculae. Existing approaches employ a definition of trabecular thickness that does not account for trabecular decay due to shortening.

Image processor 16 determines trabecular separation in each line (i) and each column (j) from:

$$Tr.Sep = (w_i/n_i) + (w_j/n_j), \tag{48}$$

where $n_i$ and $n_j$ are respectively the numbers of voids in i columns and j lines. A void is a series of uninterrupted 0 s. The presence of a 1 signals the end of the void.

Image processor 16 can output various results graphically to display 20, including:

The cortical thickness distribution around the cross section; and

The cortical thickness along the bone at any given angle (e.g. anteriorly).

Summary of Results

Image processor 16 is operable in various modes:

(i) Default Mode: The results are summarized for each slice, then for all the slices as average, minimal, median, standard deviation for indices other partial perimeters and partial surfaces. Partial perimeters and surfaces are summed for to obtain the perimeter or the surface for each slice and average to obtain the average perimeter or surface for the sample. In this default mode, all the parameters are available.

(ii) Flexible Analysis Mode: This mode of analysis allows the user to control image processor 16 to determine some parameters at specific anatomical locations (anterior, anterolateral, medial, etc). Image processor 16 provides this flexibility in the analysis because a given parameter may affect bone strength and fracture risk differently depending on the anatomical region. For example at the femoral neck, an increase in porosity on the superior aspect may be related to fracture more than a similar increase in porosity on the inferior aspect.

Image processor 16 numbers or indexes regions of interest within a slice, so each ROI corresponds to a specific anatomical location. For example, at the distal radius, ROI1 correspond to the lateral aspect of the radius as image processor 16 rotates anticlockwise, for angle of 5 degrees for example, $ROI_{36}$ corresponds to the anterior aspect, and $ROI_{54}$ to the medial aspect.

ROIs at specific anatomical locations can then be combined to provide specific indices at that location within the slice or (cross section). The number of ROIs (N) to be combined in each anatomical region is estimated to be:

$$N=(360/(m*\theta)),$$

where $\theta$ is the rotation angle, and m is the number of anatomical regions the slice is to be divided into. For example, the user can control image processor 16 to divide the slice into 2 halves (e.g. medial and lateral) by selecting a value for m of 2 starting at $ROI_1$, or m=2 starting at $ROI_i$ such as i=360/(4*θ). It should be noted that the minimal value for m is 2 (as a value for m of 1 would mean that the entire cross section is analysed, which switches image processor 16 to Default Mode), whereas the maximal value of m is 360/θ.

It should that, in Default Mode, only parameters for which local or regional values are meaningful are output. These parameters includes thicknesses, porosities, mineralization, trabecular indices are indices of strength moment of inertias. Parameters that are meaningful for the entire cross section, such perimeters and areas, are not output in Flexible Mode.

In Default Mode, the average value for the parameter at a specified anatomical location is determined for all the slices within the file.

Interpretation of Results

System 10 is able to assess the structure of bone and its changes during various interventions (such as exercise, nutrition variation or treatment) on bone. This has many applications. For example, it is suggested that treatment by drugs such as strontium ranelate, parathyroid hormone (PTH) treatment or odanacatib (in clinical trial phase 3) increase the diameter of the bone and, therefore, its bending strength. This can be examined by accurately quantifying bone dimensions without using threshold as done using system 10. A threshold based assessment of bone structure performed according to existing methods may not be optimal for this purpose as, for example, identification of bone using thresholds may result in erroneous removal new and poorly mineralised on the periosteal surface leading to the erroneous conclusion the bone has not been formed, hence periosteal apposition has not occurred when indeed it has occurred. This is likely to occur when the effect of PTH treatment on bone are being assessed. PTH is anabolic and stimulates the formation new and poorly mineralised bone. This can also occur when assessing the effects of exercise on bone as exercise especially during growth stimulates the formation of new and poorly mineralised bone.

Furthermore, strontium ranelate is absorbed by the bone tissue and has a higher atomic number that calcium. Hence, strontium treatment increases the density or attenuation of bone voxels. An increase in the density of voxels adjacent to edge of the bone (periosteum or marrow space) may affect edge detection, giving the erroneous impression that this drug has changed the dimensions of the bone. This occurs when a density based fixed threshold used (according to existing approaches) to examine bone structure before and after treatment with this agent gives an ambiguous result regarding its effects on bone structure. The conversion of all attenuations into a single BVE scale ranging from −1 to 1 and independent of the absolute attenuation of values of the bone, and the fact that thresholds are not used by image processor 16, minimizes the risk that the different effects of the drugs on attenuation or density of voxels will be confused with differential effects on bone structure (i.e. dimensions such as cortical thickness) and porosity. (With existing processing methods, conclusions about differing effects of two treatments on bone structure and porosity may be made merely because one treatment has changed the material attenuation more than another (Rizzoli R, Laroche M, Krieg M A, Frieling I, Thomas T, Delmas P, Felsenberg D., *Strontium ranelate and alendronate have differing effects on distal tibia bone microstructure in women with osteoporosis*, Rheumatol. Int. 30(10) (2010) pp. 1341-8).) Furthermore, this avoids the changes in the density of attenuation values of voxels resulting in erroneous assessment of bone architectural parameters such as porosity. For example, pores are defined as voxels with attenuation below a given value; a drug like strontium ranelate significantly increase the attenuation value of bone tissue, so a change in bone tissue attenuation may be confused with a decrease in porosity. Such erroneous assessment is minimized or eliminated in image processing performed by image processor 16.

System 10 is also able to determine the level of decay of bone and to detect fracture-vulnerable bone with a fair degree of confidence, based on the following considerations.

(i) A Normal Cortex

The absolute values of CTh and cortical area within entire cortical mass in any of its sub-compartments are not sufficient for determining whether the cortex is normal. That is, values higher than average (for the relevant subject group) does not mean that decay has not occurred. Similarly, the absolutely values of porosity and cortical area are not sufficient to determine whether a cortex is normal, as a cortex may be small owing to low growth and not owing to bone loss. Similarly a high-porosity is not necessarily the result of increased intracortical remodelling; it may also be growth-related. Hence, absolute values are merely indicative. This is a fundamental shift from current approaches which view a smaller cortex or area compared to peers as abnormal.

Instead, image processor 16 determines the architecture of the cortex and uses the result to determine whether the cortex is normal or not. A normal cortex has:
  a low PTC (<20% based on current evidence), suggesting little or no trabecularization, and
  a high PCC (>60% based on current evidence).

The normality of the cortex is further supported by one or more of the indices output by image processor 16 that is:
  Little if any decay (CD1 normal)
  Normal RDcc
  Normal RDcm
  A normal cortical thickness or cortical area
  PoCC and PoCM are low
  A low index of fragility
  (ii) A Decayed Cortex A cortex that is of similar or greater thickness than that of its peers may still be decayed (notwithstanding the classification used in existing approaches, which regard cortex of similar or greater thickness than that of its peers as normal). Some individuals are born with thicker than average cortices so, even after loosing bone, they may still have a cortex of normal thickness. Such individuals are thus misdiagnosed by existing approaches as having normal bones. However, image processor 16 does not necessarily characterize a thick cortex as normal. Rather, image processor 16 characterizes cortex (as normal or abnormal) according to its architecture. An abnormal cortex has a high PTC. In addition this cortex can be thin with a low PCC with a high porosity and low relative density, and hence high values of CD1 and/or CD2 and a high fragility.

(iii) A normal trabecular bone has a normal relative density, low porosity, a low fat proportion and fat burden.

(iv) An abnormal trabecular bone will have a low relative density, high porosity and high fat proportion and fat burden all these suggesting that trabecular bone has been lost and replaced by fat.

(v) An abnormal bone will have an abnormal cortex, an abnormal trabecular compartment, or both an abnormal cortex and an abnormal trabecular compartment.

Image processor 16 also employs porosity indices of each sub-compartment to make such determinations.

(i) Image processor 16 determines porosity from the area under the density profile curve, permitting such determinations in vivo and ensuring that the contribution of each pixel in each sub-compartment is accounted for. This may be compared to existing approaches in which porosity is determined from the number of pores within a specific bone area, which is limited by the resolution of the image (bearing in mind that most pores are not visible in such images) and by the threshold approach (also bearing in mind that most pixels classified as bone and rejected in the assessment of porosity may be tainted by PVE, that is, partially on the bone and partially on a pore). The difference between the area under the curve and the area defined by $DS_{max}$ is strongly correlated with the porosity measured by direct histomorphometry. It has been found that the increase in porosity with ageing does not occur uniformly within a specimen, so—according to this embodiment—the strip with the lowest porosity is used by image processor 16 as a marker for use in assessing the increase in porosity.

(ii) Image processor 16 can determine porosity in the trabecularized cortex and the cortico-trabecular junction. Existing approaches measure porosity only in the compact cortex, but cannot accurately assess porosity in the trabecularized cortex and the junctional zone.

Image processor 16 can determine an index of the degree of cortical porosity attributable to age-related bone (cortical decay) within the compact cortex and compact+trabecularized cortex. When the trabecularized cortex is made of cortical ruins, decay is present. Young healthy bones have cortices of varying degree of porosity but no decay. Old bones with evidence of bone loss also have bones with varying degree of porosity but high amount of decay.

Cortical fragility is the product of cortical porosity and cortical decay. It is expected that greater porosity and greater decay will result in greater fragility.

The proportion of the cortex that is compact (PCC), that is, the ratio of the thicknesses of the compact/(cortical mass) expressed as a percentage.

Thicknesses and Areas of Each Sub-Compartment:

The cortical-trabecular differentiation index (CTDI) permits differentiation between the cortex and the trabecularization. With ageing and bone loss, the de-differentiation of between the trabecular compartment and the cortical complex (i.e. cortex plus transition zone) occurs. This is a marker of decay and fragility.

It should also be noted that image processor 16 outputs most indices in the form of percentages, which are readily interpreted by the user. For example, it should be immediately apparent that a high percentage porosity or a low percentage density is deleterious. (Existing methods output absolute numbers, which are generally interpretable only by expert users; for example, densities are expressed in mgHA/cc so the user must know what constitutes a low, acceptable and high range in order to interpret such results.)

Figure 24:
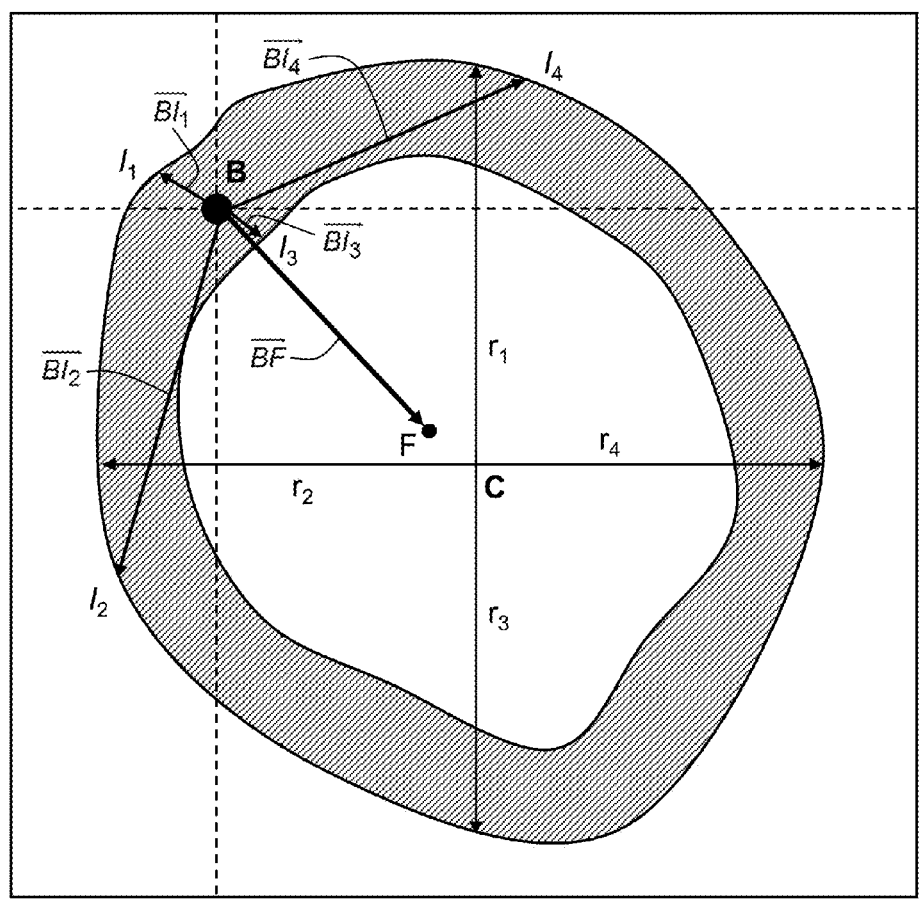
FIG. 24 is a schematic depiction of the determination of the geometric centre of a bone sample by the image processor of the system of FIG. 1 for the case where the pixel of representative density is not generally central to the sample.

In the above, it was assumed that point B is generally in the centre of the material under analysis. If not, image processor 16 can be controlled to identify a more central point F (see FIG. 24) within the material, such that:

$$\vec{BF} = \vec{BI_1} + \vec{BI_2} + \vec{BI_3} + \vec{BI_4}$$

where $I_1$, $I_2$, $I_3$ and $I_4$ are points further away from B in the top left, top right, lower left and lower right quadrants with respect to B, at the edges or beginnings of the bone (determined as described above). Image processor 16 then determines C, the centre of mass of the sample, from F in the same way that it determines C from point B described above.

Examples

Figure 25:
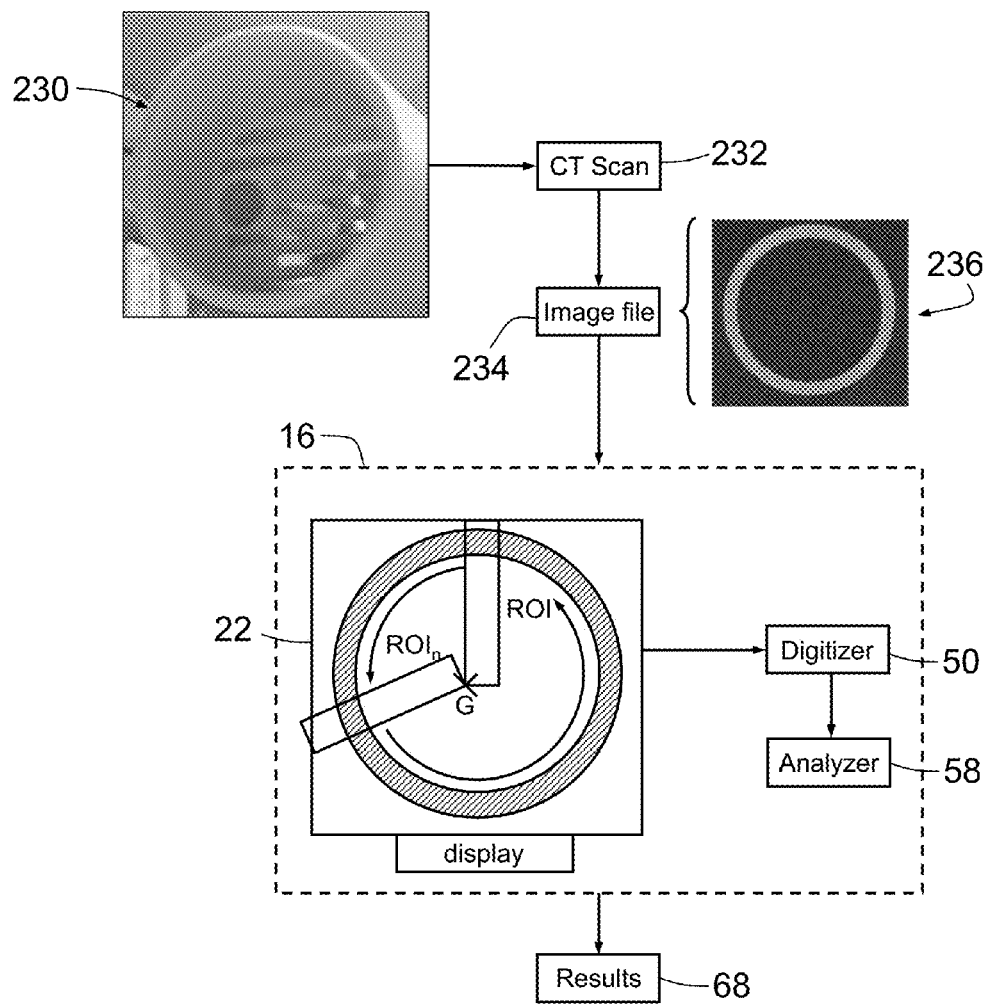
FIG. 25 is a flow diagram illustrating the use of the system of FIG. 1 to identify an object of known dimensions within an image, isolate the object and determine its dimensions.
Figure 27A:
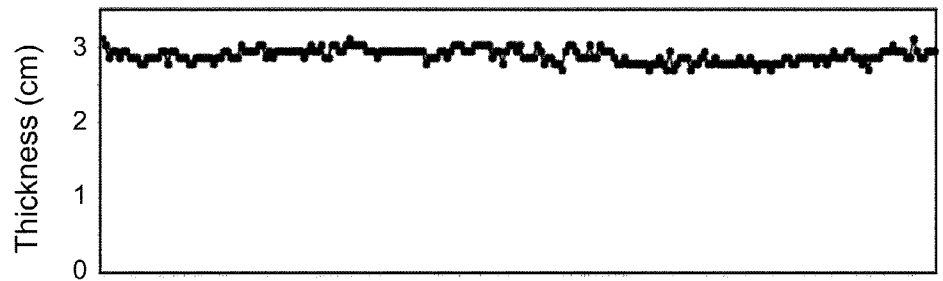
FIGS. 27A, 27B, 27C, 27D, 27E and 27F are plots, resulting from the exemplary use of FIG. 25, of thickness, radius, external perimeter, cross section, internal perimeter and internal surface area as a function of the ROIs respectively.
Figure 27B:
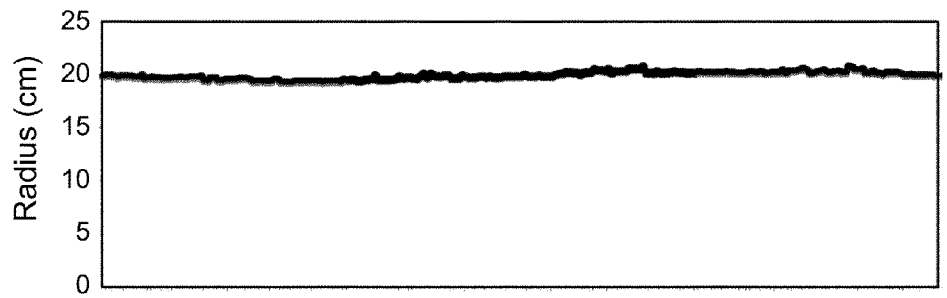
Figure 27C:
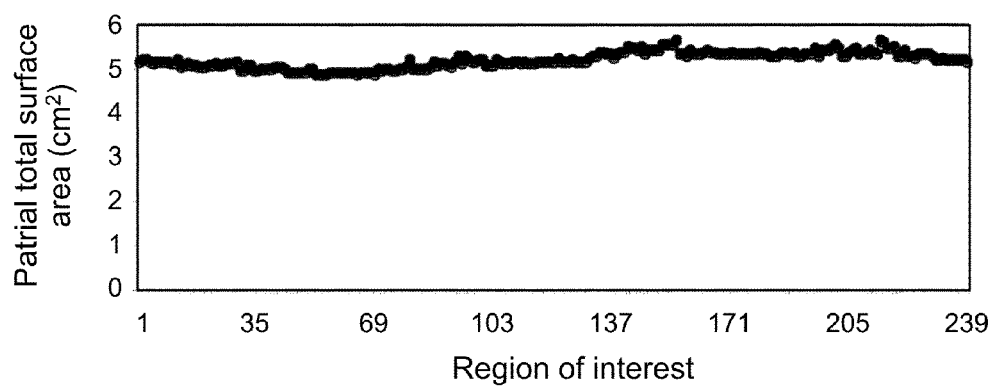
Figure 27D:
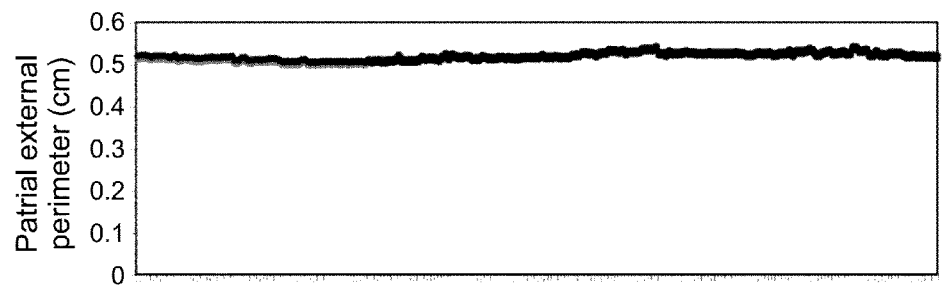
Figure 27E:
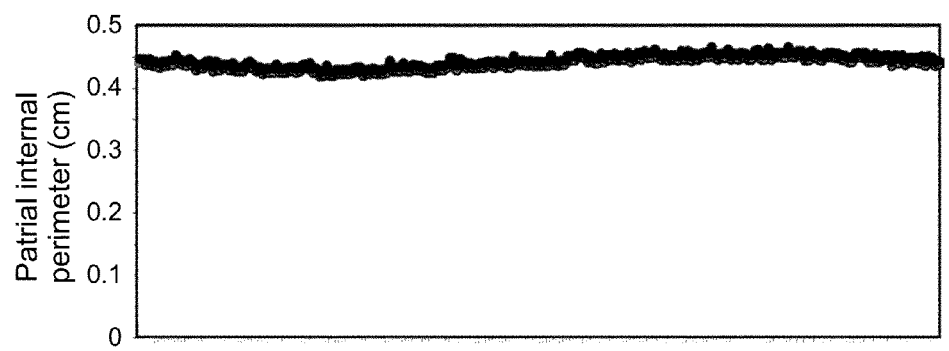
Figure 27F:
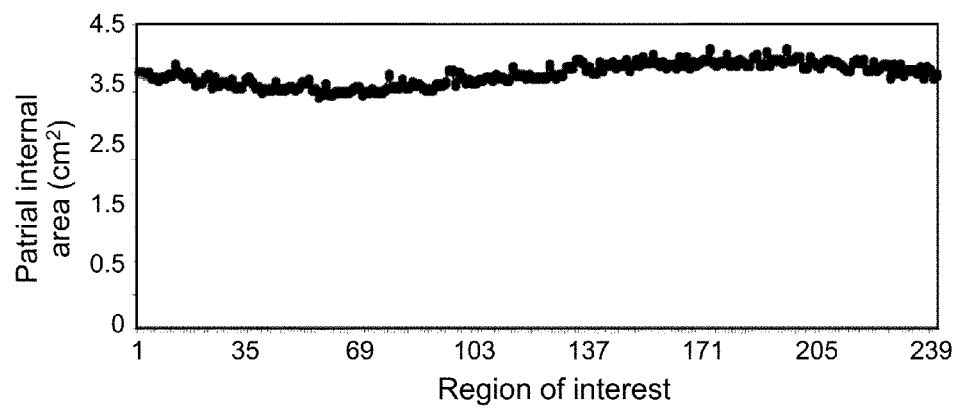

FIG. 25 illustrates the use of system 10 to identify an object of known dimensions within an image, isolate and determine its dimensions with high precision and accuracy. This experiment was used to test the accuracy and the precision of image processor 16 in identifying and determining the dimensions of a structure within an image.

Figure 26:
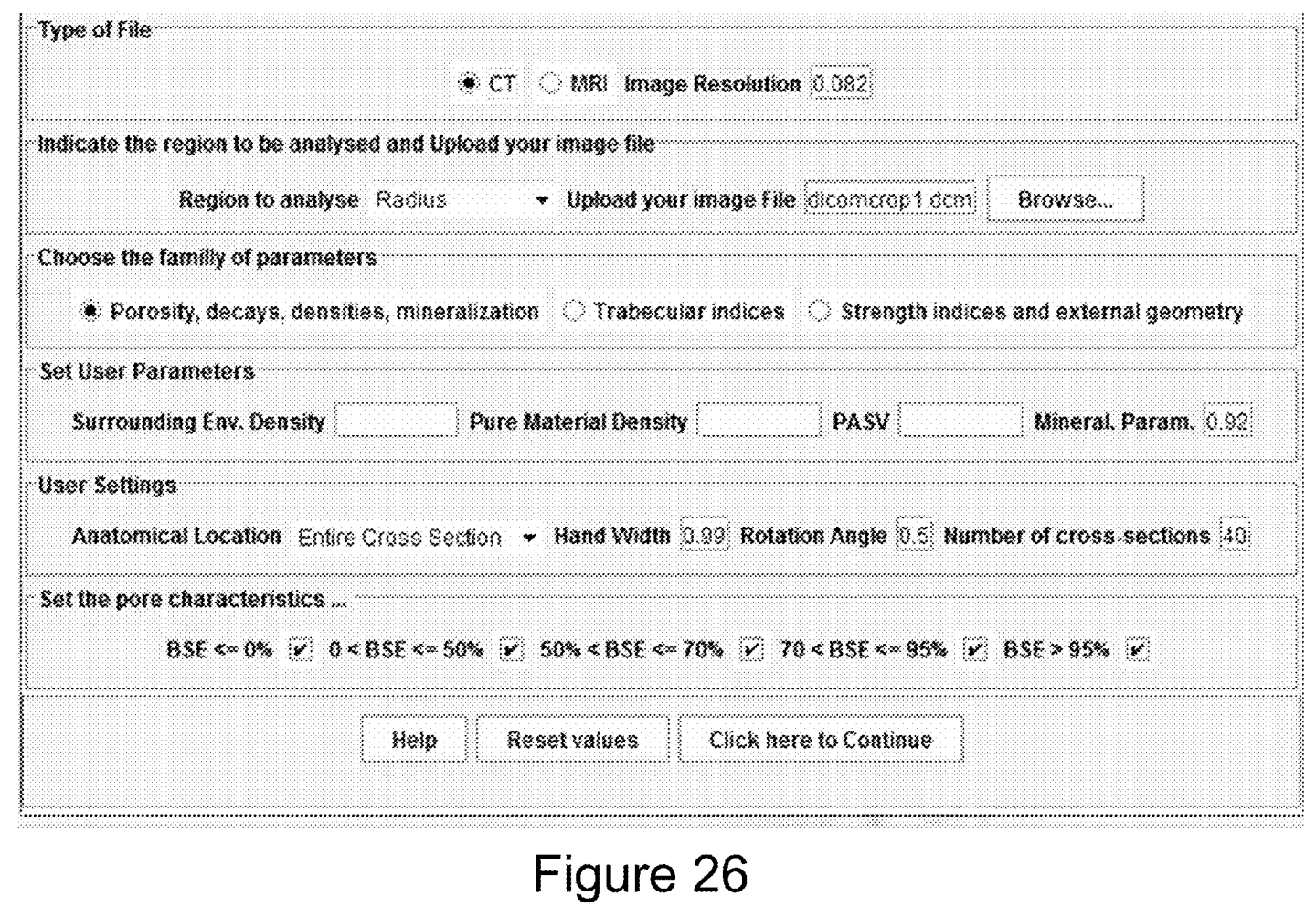

FIG. 26 is a view of a control screen of image processor 16. Various settings can be selected, as can the region (e.g. bone) to be analyzed (see the second row).

Referring to FIG. 25, a plastic tube 230 of known uniform dimensions was scanned 232 with scanner 12 of system 10. The DICOM file was retrieved from scanner 12; the resulting image file 234 (indicative of an image 236 of the tube) was generated and transmitted to image processor 16 for analysis.

The image 236 was analyzed by image processor 16 using $\theta_2$, generating 240 ROIs, and $AW_2$. Image processor 16 identified G and generated the thickness, radius, external perimeter, cross section (i.e. total area), internal perimeter, and internal surface area as a function of the ROIs (from $ROI_1$ to $ROI_{240}$), which are presented in FIGS. 27A, 27B, 27C, 27D, 27E and 27F respectively.

This test serves several purposes. Firstly, the precision of the analysis by image processor 16 can be tested. As the object 230 was known to have a uniform structure, any difference in structural parameters from ROI to ROI is largely attributable to noise in image processing. It can be seen that the dimensions (thickness, radius, etc) of the object were constant (hence almost perfectly flat lines as plotted) from ROI to ROI. This confirms that the analytical procedures used by image processor 16 to rotate and retrieve elements of a structure from ROI to ROI are sound, with little noise. (If elements of the structure differed from ROI to ROI, this would indicate that the analysis of a structure from ROI to ROI by image processor 16 were noisy and poorly reproducible). The precision of the analysis by image processor 16 was then calculated as expressed as coefficient (CV) of variation, that is, the mean of the 240 ROIs divided by the standard deviation of the 240 values. The CV for thickness, radius, external perimeter, internal perimeter, external surface and internal surface measurements were respectively 3%, 1.7%, 1.7%, 2.1%, 3.4% and 4.2%, confirming the high reproducibility of the analysis.

Secondly, as the dimensions the plastic tube were well known, the accuracy of image processor 16 in determining the dimensions of a structure could be evaluated. The size of the plastic tube was measured directly, and the corresponding parameters were determined with system 10. The results are tabulated and compared below:

| Parameter | Measured directly | Determined by system 10 | Agreement |
| --- | --- | --- | --- |
| thickness of plastic | 3 cm | 2.9 cm | 96.7% |
| radius | 19.75 cm | 19.99 cm | 98.7% |
| external perimeter | 124.09 cm | 125.6 cm | 98.8% |
| internal perimeter | 105.2 cm | 106.8 cm | 98.5% |
| external surface area | 881.4 cm$^2$ | 908.6 cm$^2$ | 97% |
| internal surface area | 1225.4 cm$^2$ | 1256.1 cm$^2$ | 97.5% |

Altogether, this shows that image processor 16 can automatically detect an object within an image and determine its dimensions with good precision and accuracy.

In addition, image processor 16 was able to automatically identify the plastic tube and robustly determine its dimensions without using thresholds (as employed in existing techniques). Unlikely image processor 16, existing techniques require an external input to perform such analysis; that is, an operator must reset the density threshold for detection so that the object can be identified within the image. This requires knowing a priori the density of the object and/or manually adjusting the image until the image of the object appears separated from the surrounding environment. Image processor 16 is adapted to identify a structure within an image and separate it essentially regardless of its density.

Figure 28:
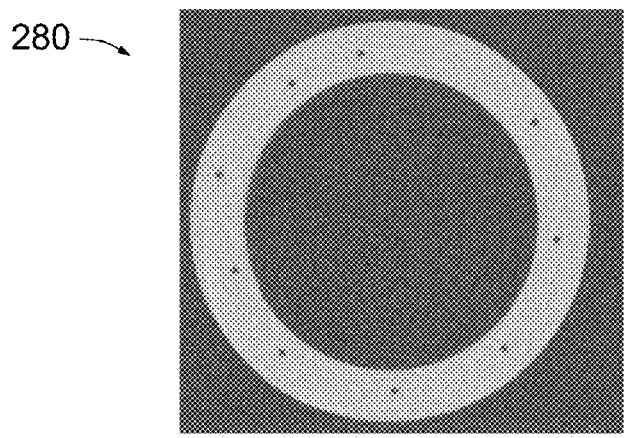
FIG. 28 is a cross-sectional grayscale image of an exemplary phantom sample for use with the system of FIG. 1, comprising a plastic tube with drilled holes.
Figure 29:
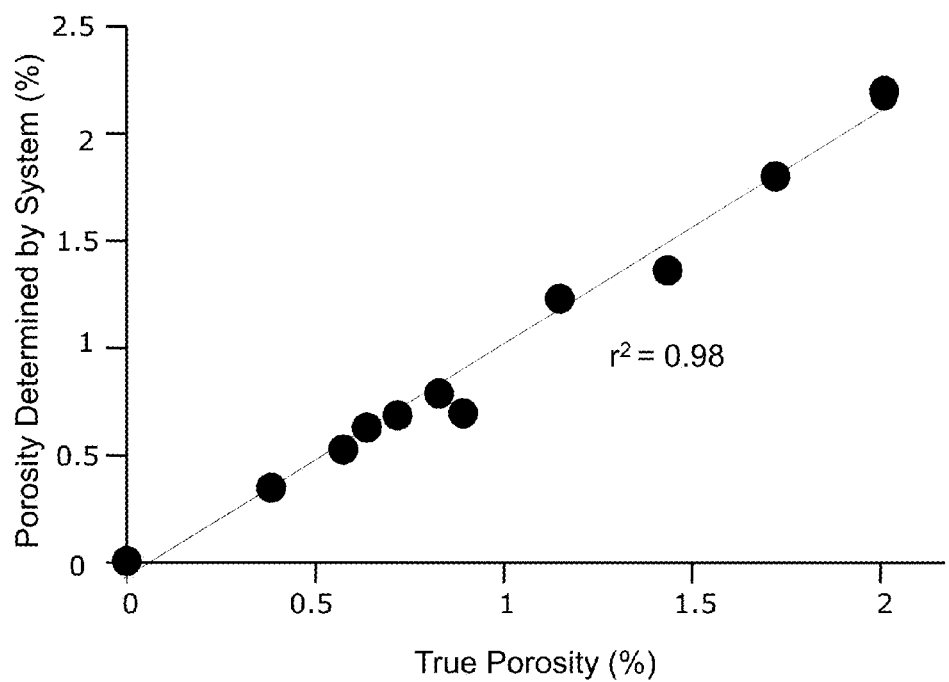
FIG. 29 is a plot of porosity of several plastic tubes comparable to that shown in FIG. 28 obtained using the system of FIG. 1 against known porosity.

In another example, a variety of numbers of holes were drilled in a series of plastic tubes (such as that shown in cross section in grayscale image 280 of FIG. 28) to produce different levels of porosity. These tubes were then imaged using system 10, images were collected and porosity was quantified using image processor 16. FIG. 29 is a plot of the porosities determined by system 10 against the true porosities (i.e. those determined experimentally from the known characteristics and numbers of holes in each tube). A high correlation was found, with an r$^2$ value of 0.98.

Figure 30:
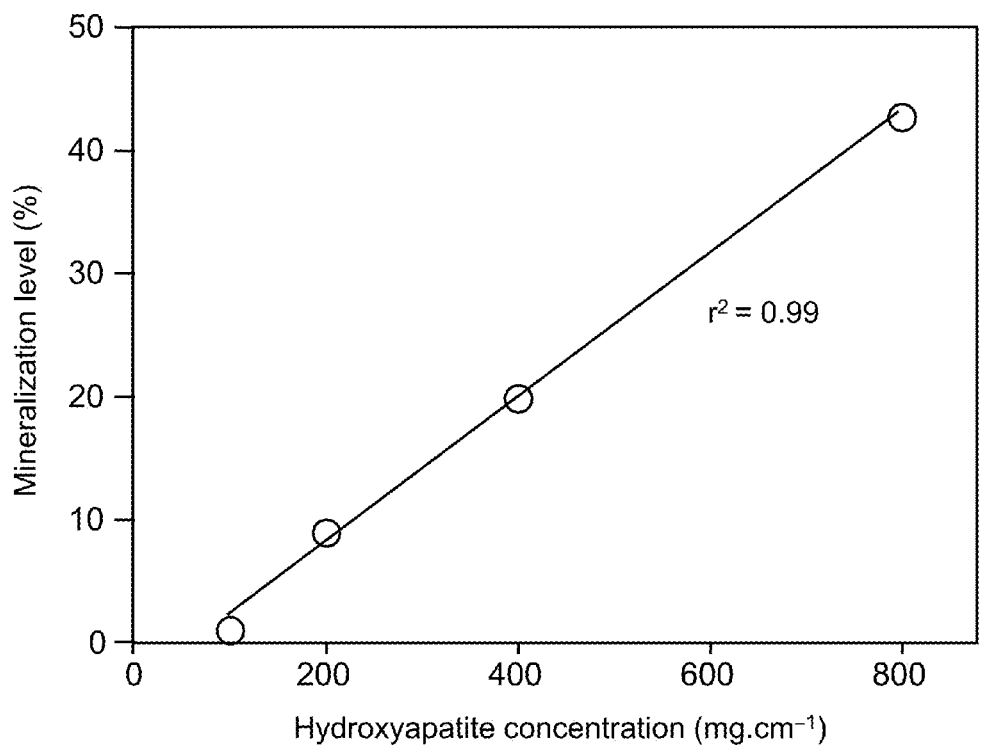
FIG. 30 is a plot of porosity of four phantom samples of different but known concentrations of hydroxapatite obtained using the system of FIG. 1 against known porosity.

In a further example, four cylindrical phantoms of different but known concentrations of hydroxapatite were imaged using CT scanner. The images were collected with system 10 and analyzed using image processor 16 to determine the level of mineralization. FIG. 30 is a plot of the mineralization level (%) from image processor 16 against the known hydroxyapatite concentration (mg·cm$^{-1}$): high correlation between the two is again evident.

Twenty-four bone specimens from cadavers were studied using scanning electron microscopy (SEM) and QCT, and their bone density was measured in in vivo like conditions (after submersion in saline and an adequate internal rotation of 15°). Porosity and other indices were determined directly from micrographs and estimates after DICOM file from CT scanner 12 using image processor 16. Porosity profile curves (analogous of density profile) were generated after porosity was measured directly from SEM images. Points identified by image processor 16 from the density profile curves were compared with the image scans and SEM micrographs.

Examples of these results are shown in FIGS. 31A, 31B, 32A, 32B, 33, 34A, 34B, 35 and 36.

Micrographs from the subtrochanteric region, bone mineral density (BMD) in these specimens were measured at the trochanteric region and converted into T-scores using the Geelong reference range which is the reference recommended by the Australian and New Zealand Bone and Mineral Society.

Figure 31A:
FIGS. 31A and 31B are micrographs of bone samples analyzed with the system of FIG. 1.
Figure 31B:
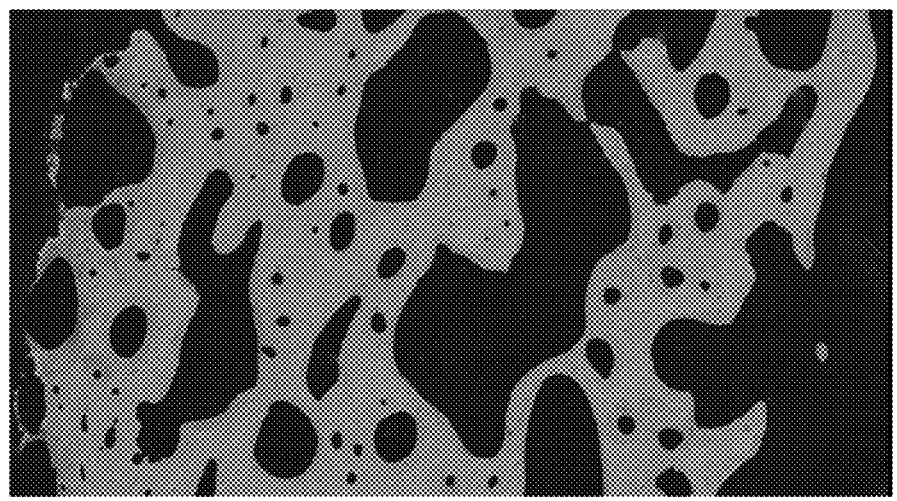

FIG. 31A is a micrograph from image processor 16 of bone from a 72 year old woman with a modestly elevated intracortical porosity as can be seeing on the micrograph. The small increase in porosity is recognized by image processor 16, which quantifies the porosity as 4.4%. FIG. 31B is a micrograph from image processor 16 of bone from a 90 year old woman with a markedly elevated intracortical porosity. This markedly increased in intracortical porosity is also captured by image processor 16 which quantifies the porosity as 35.1%. The difference in decay between the two samples is clearly visible, FIG. 31A showing more decay that FIG. 31B. This was confirmed by porosity results determined with image processor 16 (whereas according to a conventional bone density tests, these two bones have similar decay, as bone density tests do not discern the difference in fragility between these two bones).

Figure 32A:
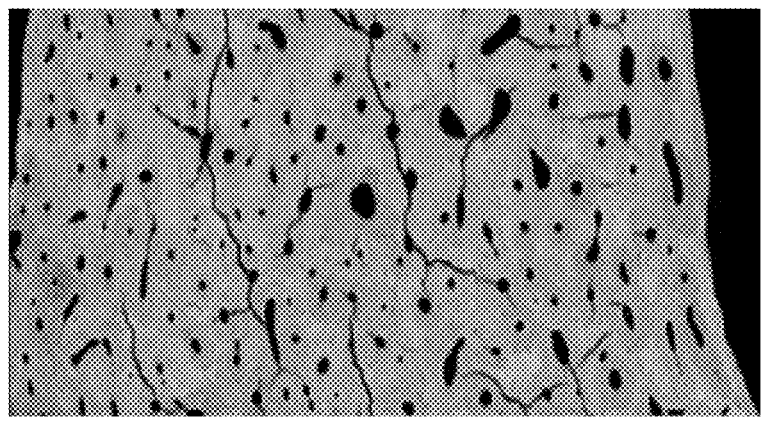
FIGS. 32A and 32B are micrographs of further bone samples analyzed with the system of FIG. 1.
Figure 32B:
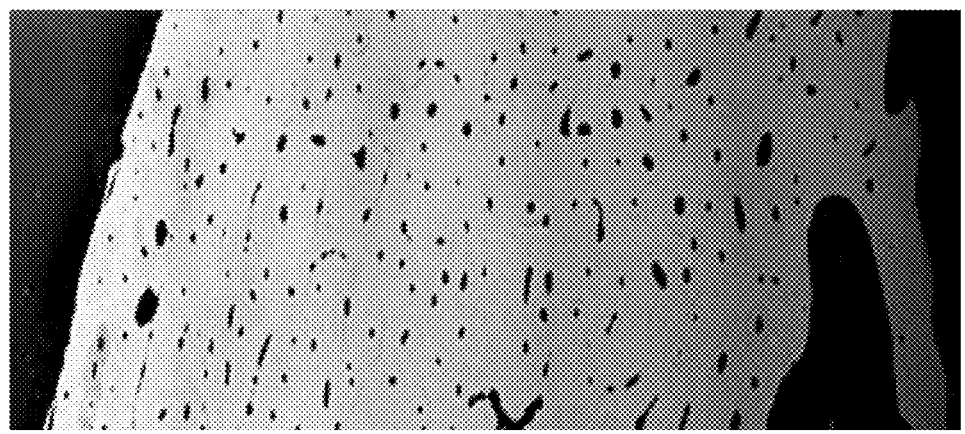

FIG. 32A is a micrograph from image processor 16 of bone from a 29 years old woman with minimal porosity; image processor 16 quantified the porosity of this sample as 0.9%. FIG. 32B is a micrograph from image processor 16 of bone from a 72 year old woman with normal cortex and low porosity; this low porosity is well captured by image processor 16, which quantified the porosity of the sample of FIG. 32B as 0.1%. However, according to the BMD test (the currently used method of diagnosis), the 29 year old woman is normal (with a T-score of 1.92) whereas the 72 year old woman is osteopenic (with a T-score of −1.14), suggesting bone fragility in the older woman when there is none. Image processor 16 thus has the potential to avoid such cases of misdiagnosis by adequately detecting decay when it is present.

Figure 33:
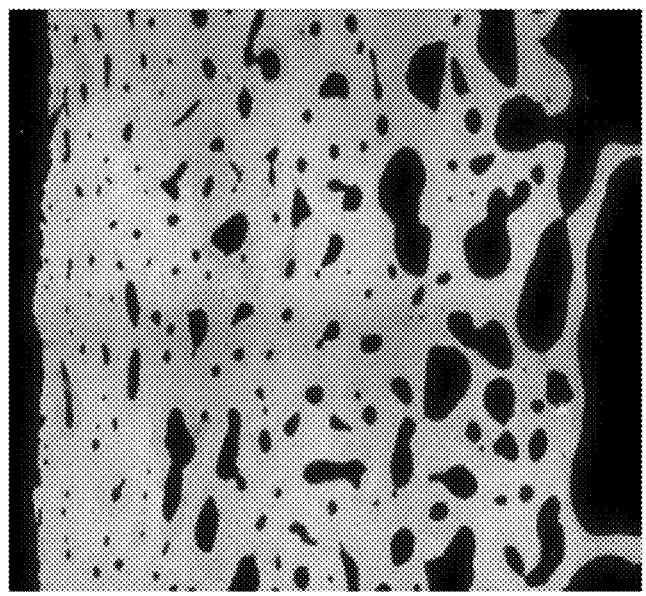
FIG. 33 is a micrograph of another bone sample analyzed with the system of FIG. 1.

FIG. 33 is a micrograph from image processor 16 of bone from a 67 year old women with a significantly decayed cortex (as can be seen in the micrograph). Image processor 16 captured this decay and quantified porosity as 14.7%. However, the woman was classified according to the BMD test as normal (with a T-score of −0.2). Many people with a normal bone density test sustain a fracture at some point; it is likely that this woman would be one of them. It is expected that image processor 16 analysis would identify these people who fracture despite having a normal BMD test.

Figure 34A:
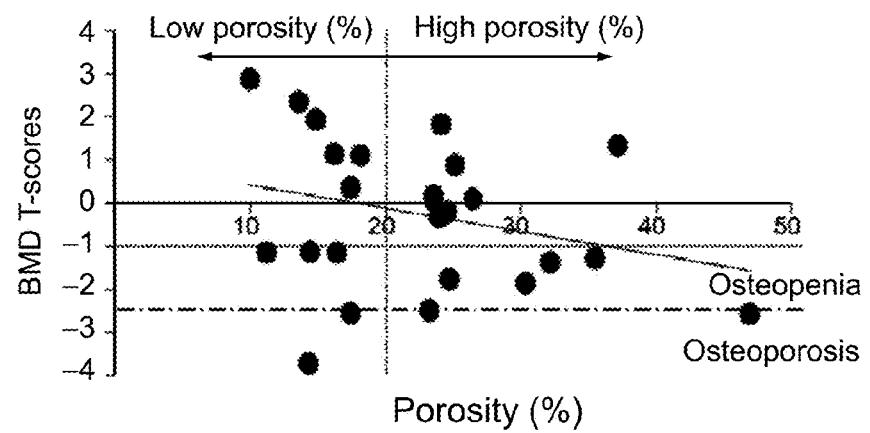
FIG. 34A is a plot of BMD T-scores against porosity for 24 specimens, illustrating the poor correlation between the levels of porosity measured directly from SEM images and BMD diagnosis thresholds in the 24 specimens analyzed.

FIG. 34A is a plot of BMD T-scores against porosity (expressed as percentage of bone area), and illustrates the poor correlation between the levels of porosity measured directly from SEM images and BMD diagnosis thresholds in the 24 specimens analyzed. This shows that BMD test poorly captured cortical decay. About 50% (7/13) of the specimens with high porosity (>20% of bone area) consistent with having lost bone, had normal BMD (T-score>−1). Only 50% (2/4) of specimens with low aBMD (T-score<−2.5 SD) have high porosity (>20%); the remaining had low aBMD despite having normal porosity. Of the 10 specimens with T-scores less than −1 (i.e. osteopenic or osteoporotic), only 5/10 (50%) had low porosity and the remaining 50% had high porosity.

Figure 34B:
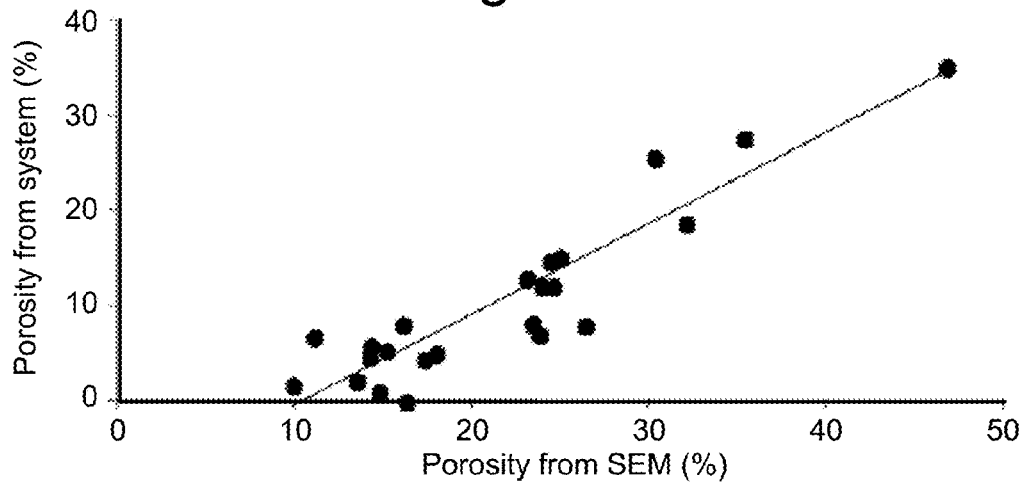
FIG. 34B is a plot of percentage porosity determined by the system of FIG. 1 against percentage porosity measured directly from SEM images.

FIG. 34B is a plot of percentage porosity determined by system 10 against percentage porosity measured directly from SEM images. As is apparent from this plot, porosity as quantified by image processor 16 correlated well with directly measured porosity.

Figure 35:
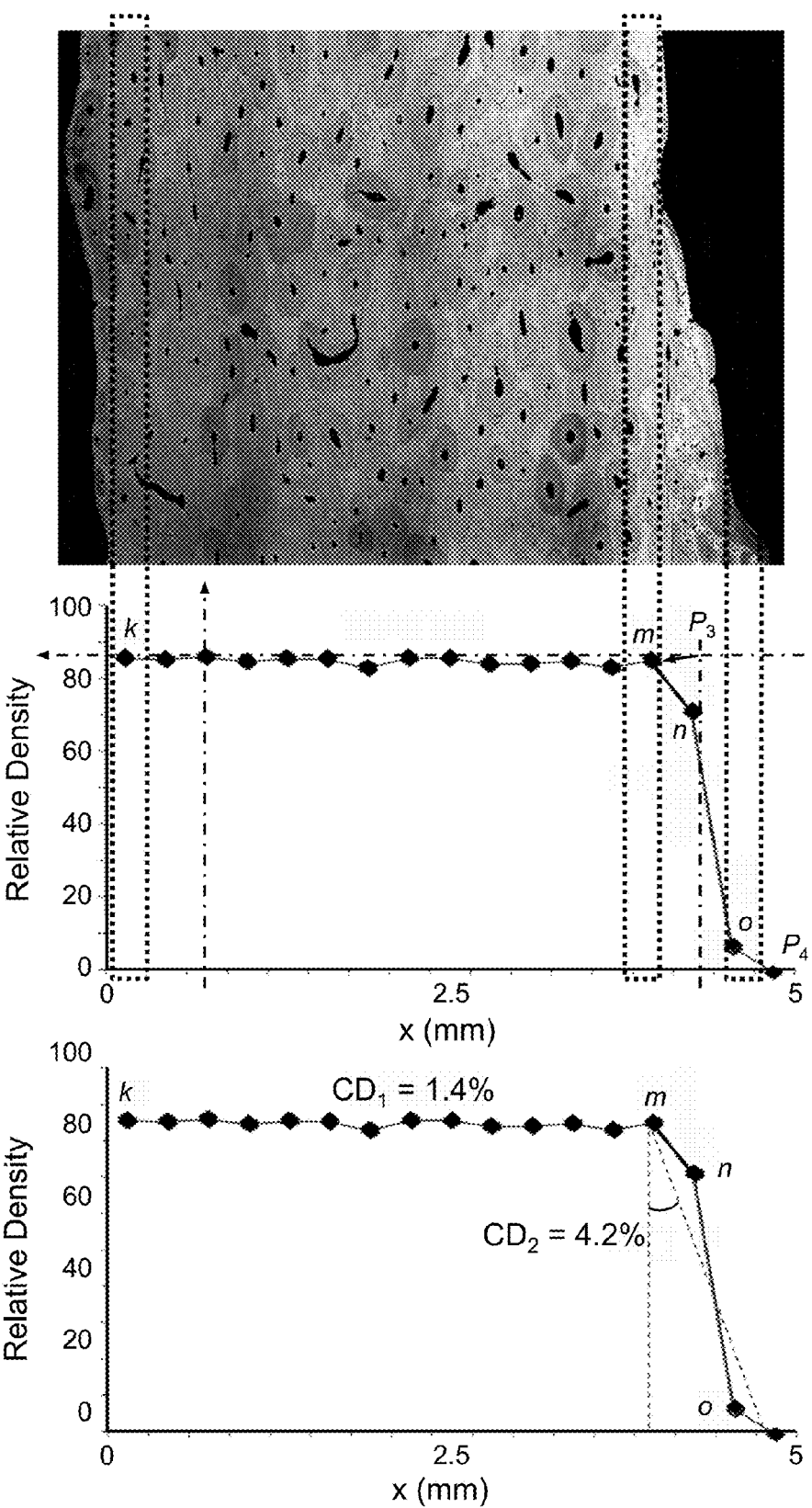
FIG. 35 illustrates the positions of points m, n and o within a density profile curve determined by the system of FIG. 1 when compared with direct observation of the corresponding SEM image, for a bone sample.
Figure 36:
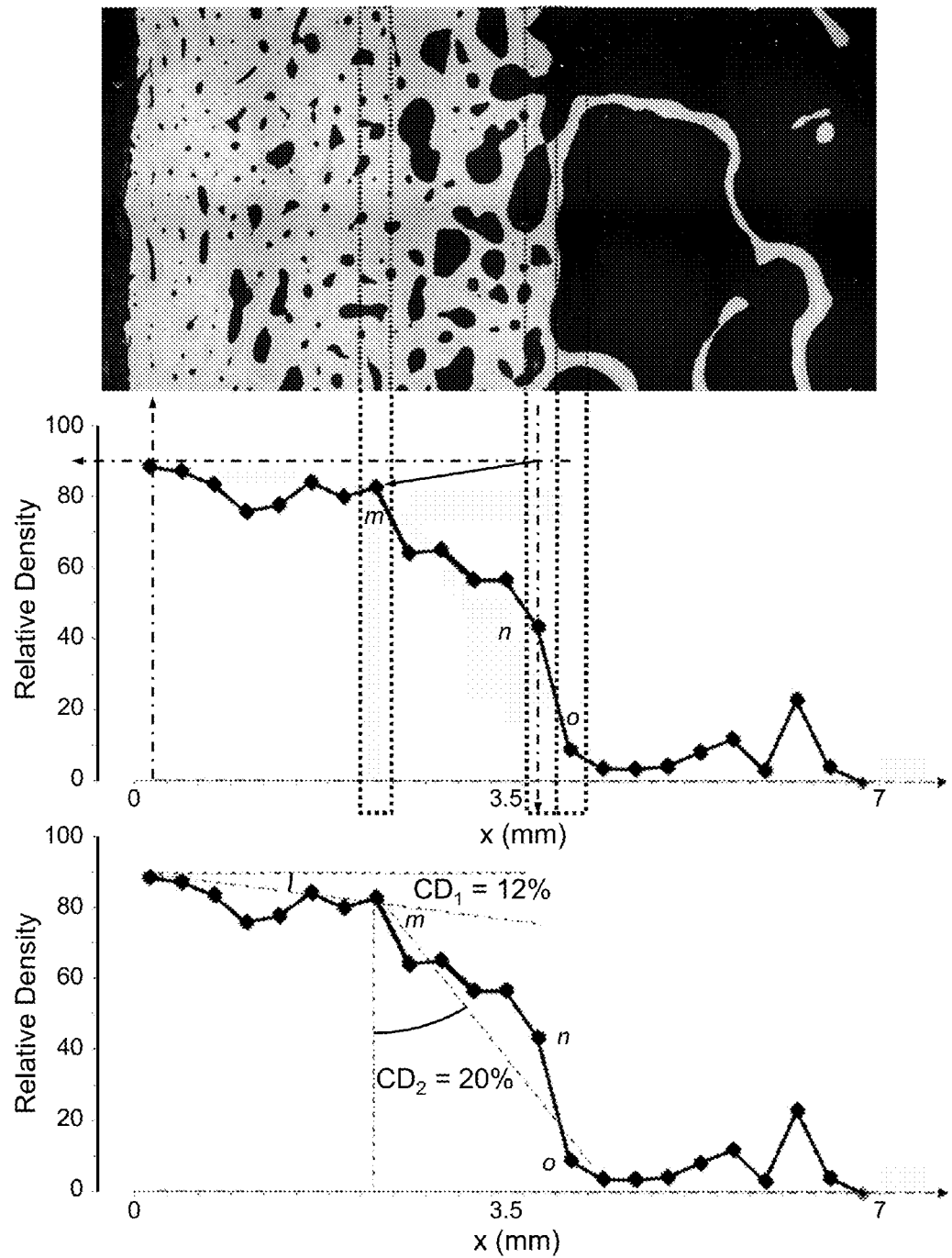
FIG. 36 illustrates the positions of points m, n and o within a density profile curve determined by the system of FIG. 1 when compared with direct observation of the corresponding SEM image, for another bone sample.

FIGS. 35 and 36 illustrate the positions of points m, n and o within a density profile curve when compared with direct observation of SEM images for two respective samples. The ability of image processor 16 to identified points within the density profile curve as compared to images generated in vivo from DICOM files and analysed by image processor 16 was presented above (detailed description of the invention).

In these two in vitro samples, it can be seen that the points and hence the dimensions (in particular thicknesses) within the samples are clearly identified. The decay of the compact cortex (CD1) and trabecularised cortex (CD2) are also indicated. Referring to FIG. 35, sample 1 is from a 29 year old woman with a histologically normal cortex. This was confirmed by image processor 16, which found a CD1 of 1.4% and a CD2 of 4.2%; this corresponds to a homogeneous cortex followed by a clear transition from the cortex to marrow space. The cortex is almost entirely compact (PPCC=87.5%), the PTC and PCTJ are limited to one strip each, and therefore inexistent as discussed in the section on unsuitability of the analysis. The normality of the sample is further confirmed that by a cortical fragility index of 1.26%.

Referring to FIG. 36, sample 2 is from a 65 year old woman. The decay of the cortex is visible on the micrograph (top register) and confirmed by image processor 16, which quantified CD1 and CD2 as 12% and 20% respectively. The more decayed state of the sample is further confirmed by the percentage of compact cortex (determined by image processor 16 to be 57.1%), the percentage of trabecularized cortex (PTC) (determined by image processor 16 to be 37.1%), and the index of cortical fragility (determined by image processor 16 to be 6.8%).

In addition, DICOM files with scan data obtained from living individuals (five from fracture cases and three from non-fracture individuals) were obtained, to test system 10 with QCT data files relating to living individuals. The relevant points in the density profiles were identified and the relevant indices determined with image processor 16. It was found that:

1) Image processor 16 was able to identify relevant points (i.e. j, k, l, m, n, o) and to compare image and direct SEM measurements as discussed above.

Correlation between porosity measured directly and porosity estimated by image processor 16 was excellent.

2) The porosity (assessed by image processor 16) correlates poorly with bone density, the currently used method to identify individuals at risk for fracture. This suggests that the two techniques overlap but do not capture the same things.

In the appendix (end of the text), are presented examples of specimens studied. Micrographs and porosity scores as determined by image processor 16 are shown as well as the BMD T-scores values in these individuals. A BMD T-score of less than −1 is considered osteopenic while T-score of −2.5 or less is osteoporosis.

Comparative values of porosity in individuals with fracture of distal radius and those without fracture are shown in the appendix also. The indices and parameters determined by image processor 16 allow discrimination between individuals with and without fracture-vulnerable bones.

Figure 37A:
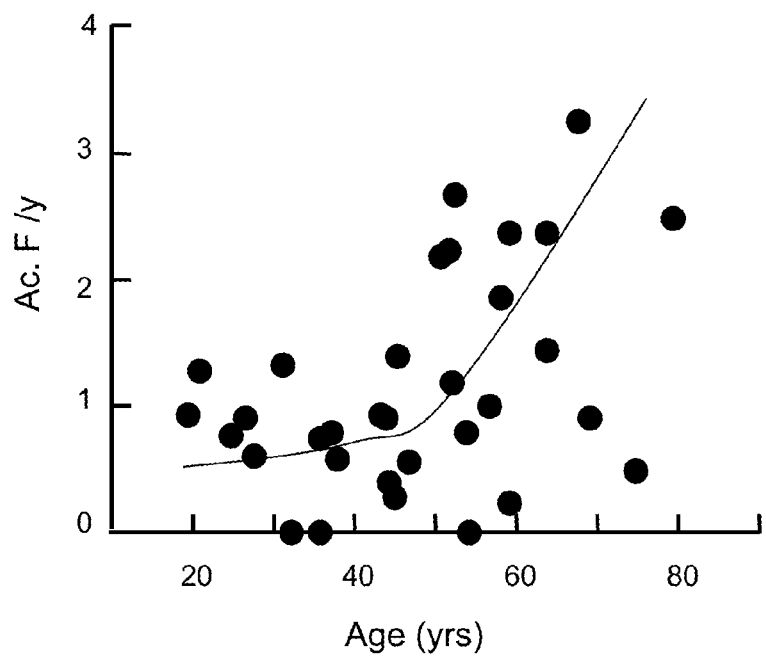
FIG. 37A is a plot of age-related increase in activation frequency (Ac.F) per year measured directly by histomorphometry as a function of age.
Figure 37B:
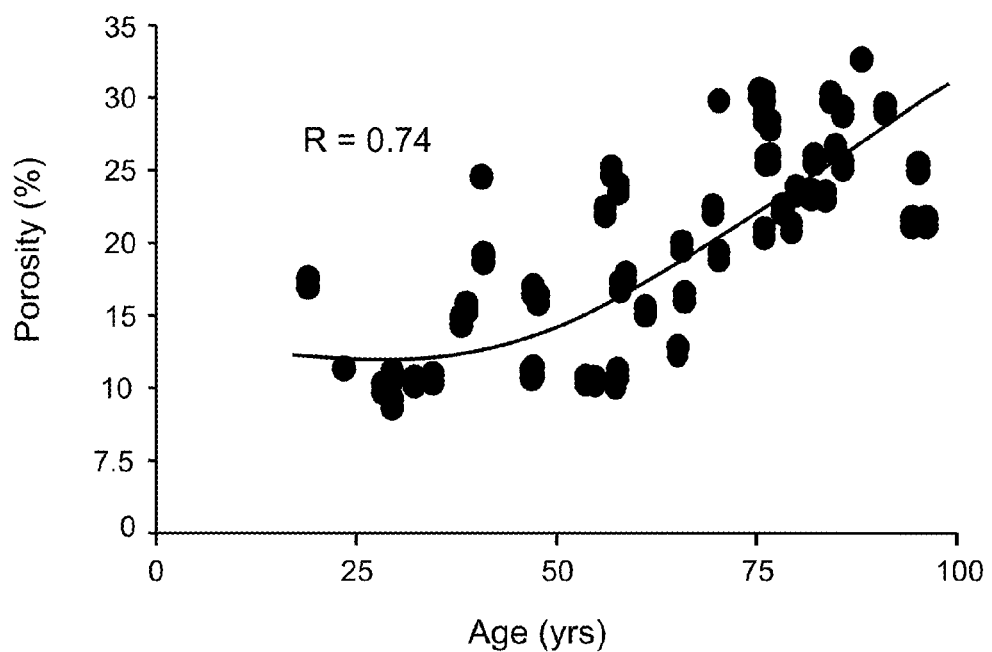
FIG. 37B is a plot of age-related increase in porosity measured using the system of FIG. 1, for comparison with the data of FIG. 37A.

In a further example, it was shown that the age-related increase in porosity as measured using image processor 16 is similar to that of activation frequency measured directly using histomorphometry. FIG. 37A is a plot of age-related increase in activation frequency (Ac.F) per year measured directly by histomorphometry as a function of age (Compston, *Porosity increase from the rise in Ac.F within intracortical pores (haversian and Volkmann canals*, private communication). FIG. 37B is a plot of age-related increase in porosity measured using image processor 16, in 73 women. The data in these two figures demonstrates similar trends.

FIGS. 38A, 38B and 38C are cross sectional views of a radius. FIG. 38A is a greyscale image of the distal radius reconstructed from high-resolution peripheral quantitative computed tomography (HRpQCT) data. FIG. 38B is an image of the same sample, reconstructed by image processor 16 after extraction of the periosteal surface, demonstrating the ability of image processor 16 to segment an image from the background. The image was reconstructed from BVE values; black (generally inner region) to red (generally outer region) represent increasing BVE values. It will be noted that, because a threshold is not used by image processor 16, image processor 16 extracts the external contour of a material (periosteal surface of the bone in this case) while preserving the original attenuation of all the voxels within the material. This allows image processor 16 to fully characterize the material after it has been segmented from the background, including assessing porosity and tissue mineralization level.

Figure 38D:
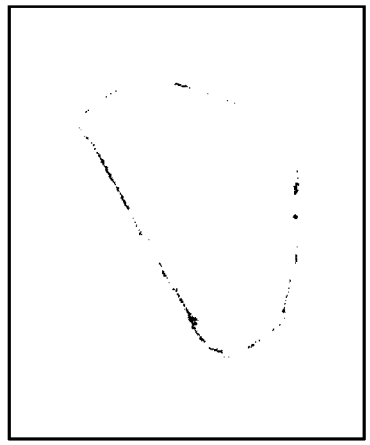
FIG. 38D is a plot extracted from FIG. 38C of the outer transition zone only.
Figure 38E:
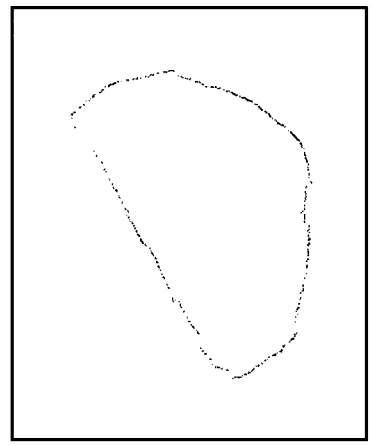
FIG. 38E is a plot extracted from FIG. 38C of the inner transition zone only.
Figure 38F:
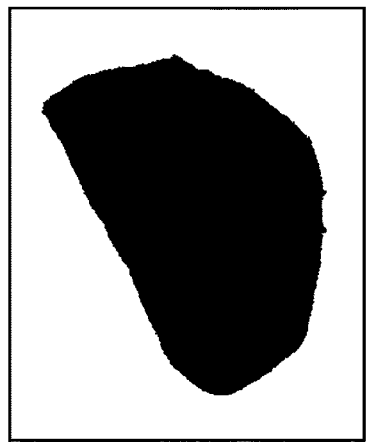
FIGS. 38F and 38G are greyscale versions of, respectively, FIGS. 38B and 38C.
Figure 38G:
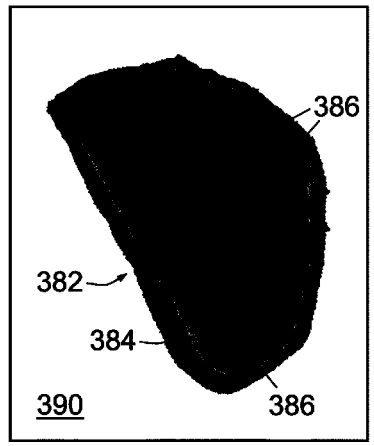

FIG. 38C is another view of the sample, showing the segmentation of the same image into the four compartments of bone described above. Red is the compact cortex 382, light green is the outer transition zone 384, cyan is the inner transition zone 386, and blue is the marrow space occupied by trabecular bone 388. (Inner transition zone 386, where visible, lies between outer transition zone 384 and trabecular bone 388. FIGS. 38D and 38E, respectively, plot outer transition zone 384 and inner transition zone 386 only in greyscale.) White is the background or surrounding muscle tissue 390. FIGS. 38F and 38G are greyscale versions of, respectively, FIGS. 38B and 38C.

In addition, an example of automated identification and analysis of a foreign body within the bone is shown in FIGS. 39A, 39B and 40. A discussed above, image processor 16 can automatically identify and analyze a structure within an image. While the main application of system 10 is the identification and analysis of bone, the use of image processor 16 is by no means limited to this application.

FIG. 39A is an image as displayed by display 22 of image processor 16. A bright object is evident within the image and, although the bright object resembles a cross section of a bone, it is actually the head of a metallic safety pin. This experiment was designed to simulate the presence of a metallic foreign body within a subject or other object, such as a bullet or a coin (perhaps inadvertently swallowed).

The head of the safety pin was buried insight muscle tissue and imaged with system 10; the bright object in the image of FIG. 39A is thus the cross section of the head of the safety pin. Image processor 16 readily identified this structure, separated it from the surrounding muscle tissue, and analyzed its structure, permitting a diagnosis of a metallic body within the muscle tissue.

$ROI_1$—which is marked in FIG. 39A—is shown enlarged in FIG. 39B. FIG. 40 (upper register) is the density profile curve associated with $ROI_1$. FIG. 40 (lower register) is the function $\lambda_1$ associated with the density profile curve shown in the upper register of FIG. 40. As described above, $\lambda_1$ is the function that enables the bone to be distinguished from the surrounding soft tissue. In this case $\lambda_1$ enables the separation of the object that was analyzed (viz. the head of the safety pin) and the surrounding muscle tissue. The function $\lambda_1$ determines that a clear separation between the object and the surrounding muscle is at point 99 (see the lower register of FIG. 40). Point 99 is indicated in the density profile curve (see the upper register of FIG. 40), and in the image of ROI$_1$ (see FIG. 39B). It should be noted that j, in this case point 99, is selected by $\lambda_1$ in such a way that most of the haziness (white blurry area adjacent to the object, open square) adjacent to the structure is not included in the surrounding soft tissue. This hazy area is due to partial volume effects, and image processor 16—using $\lambda_1$—can separate the object from the surrounding muscle tissue with minimal artifacts due to partial volume effect on muscle tissue. Furthermore, partial volume effects do not affect the ability of image processor 16 to identify the beginning of the object (point m, in this case at point 110) free of artifacts. Image processor 16 readily identifies point n (at point 115), enabling it to isolate the mass of the object free of artifacts (PVE) and free decay (referred to as trabecularization in the case of a bone).

Image processor 16 therefore identifies, and isolates the object, and the surrounding muscle while minimizing the interference from artifacts. The nature of the object can thus be identified by comparing its density to that of the surrounding muscle, whether by calculating its relative density or its absolute density (such as in mgHA/cc or g/cc).

Image processor 16 determined the relative density of the object viewed in FIG. 39A to be 93.5%. Hence, the object (in fact the head of a safety pin) is much denser than muscle and is therefore not bone (the relative density of which is typically ~66% and no greater than 75%, and ~3 times greater than muscle). In absolute terms, image processor determined the density of the object to be 6036 mgHA/cc or 4.6 g/cc equivalents, confirming that the object is of a density corresponding to a metal. (In absolute terms, the density of purely mineralized bone does not exceed ~1200 mgHA/cc equivalent or ~2 g/cc.) The presence of an object of a much greater density than the bone within a muscle tissue indicates the presence of a foreign body.

The examples presented are not a complete list of the potential used of image processor 16. It is envisaged that its potential ability to automatically identify, separate and analyze objects (or elements) of an unspecified image (i.e. where the constituents are unknown), often without human intervention, will have applications in other areas of medicine (such as in the diagnosis of vessel calcifications, acute myocardial infraction, fracture and stroke) but also outside the field of medicine. For example, one such application is for the automated image analysis of image processor 16 for the creation of artificial vision. In these circumstances, image processor 16 would be integrated in a camera to perform a contemporaneous analysis of images. After analyzing the image, image processor 16 instantly transfers the results to a "command centre" for decisions making. Such a "command centre" could be a person or a software with specific instructions. Artificial vision would have many applications within and outside of medicine. Outside medicine, image processor 16 could be used, for example, for controlling a robot.

The examples presented above suggest that image processor 16 is a useful tool for an automated identification, separation and analyses of the structure of an object within an image, and in particular the automated segmentation and analysis of bone. The indices determined by image processor 16 allow the assessment of cortical bone structure that is not the mere measurement of cortical thickness, cortical area and cortical density.

Figure 41B:
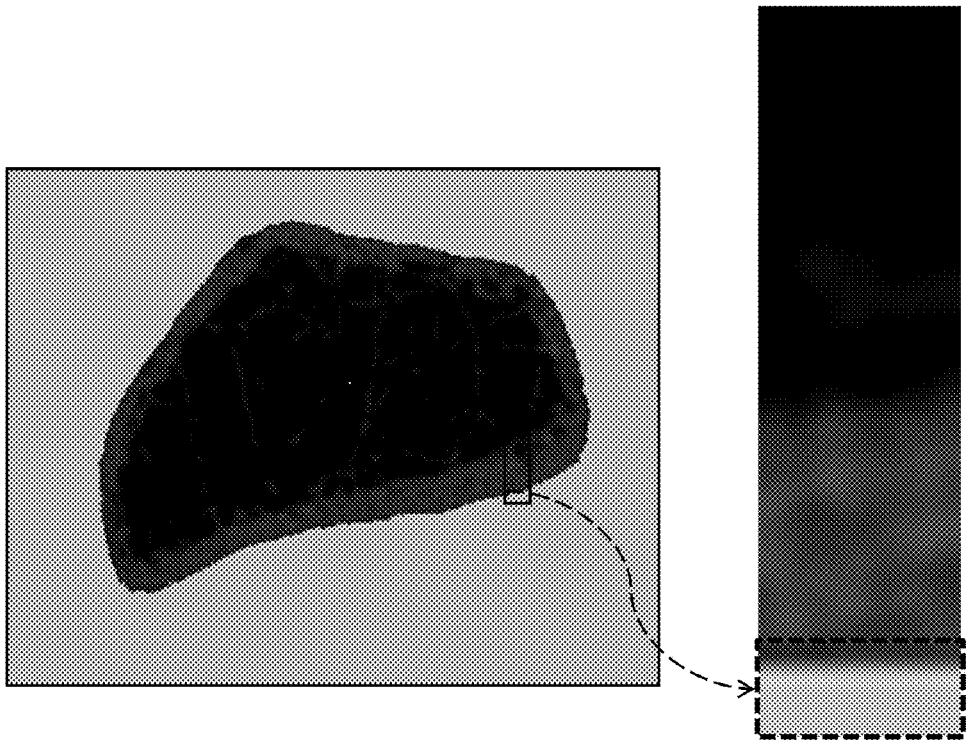
FIG. 41B is a cross sectional view of the same distal radius generated by the system of FIG. 1.
Figure 41A:
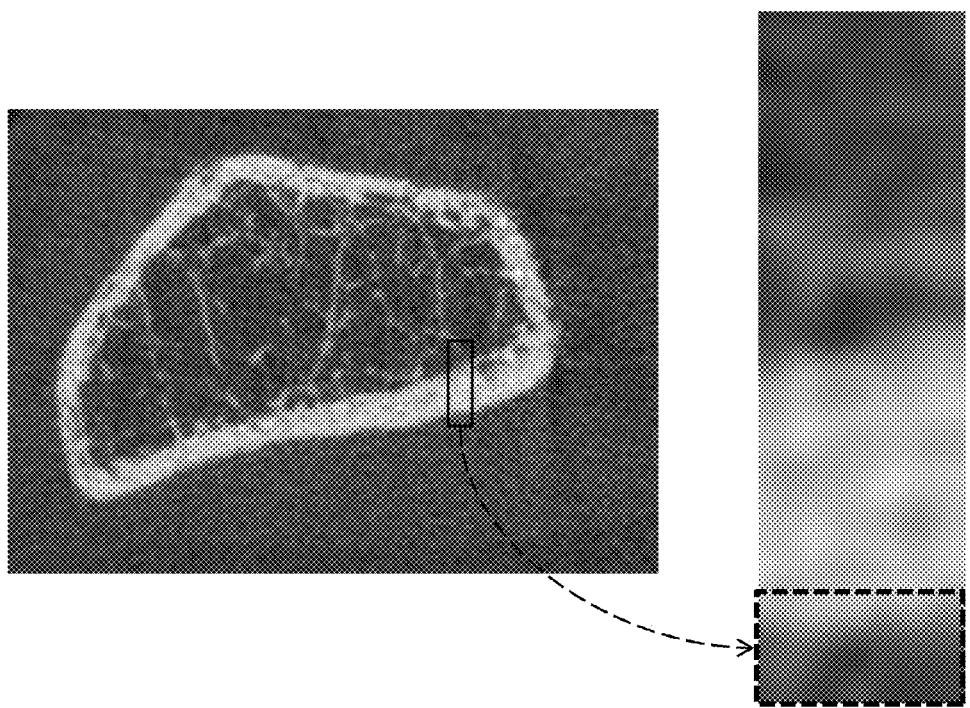
FIG. 41A is a cross sectional view of a distal radius generated by a system of the background art.

Image processor 16 can retrieve an image from surrounding background, while minimizing the confounding effects of PVE. For example, the upper register of FIG. 41A is a cross sectional view of a distal radius; the upper register of FIG. 41B is the same cross section reconstructed by image processor 16 after separating the bone (radius in this case) from the surrounding background. The lower register of FIG. 41A is an enlarged view of an interface (or junction) between the background and the bone, which is blurry owing to partial volume effects (i.e., voxels that are partly bone, partly background). The lower register of FIG. 41B, however, is the same junction after processing of the image by image processor 16. The delineation is much sharper: blurry voxels (i.e. those tainted by partial volume effects) have been separated and left in the background, and hence the margin of bone is more clearly apparent.

This process of separation of a material within an image from the background while minimizing the blurring due to partial volume effects has many applications in medicine and outside the medical field.

Image processor 16 can separate bone from background better than existing software that is based on a threshold approach. FIG. 42A, upper register, is a cross sectional view of a tibia. The external boundary is drawn with conventional threshold-based software. It can be seen that a significant amount of bone has been left out of this boundary and erroneously included in the background. FIG. 42A, lower register, is a magnified view showing a particular portion of bone outside the boundary and hence erroneously included in the background.

Figure 42B:
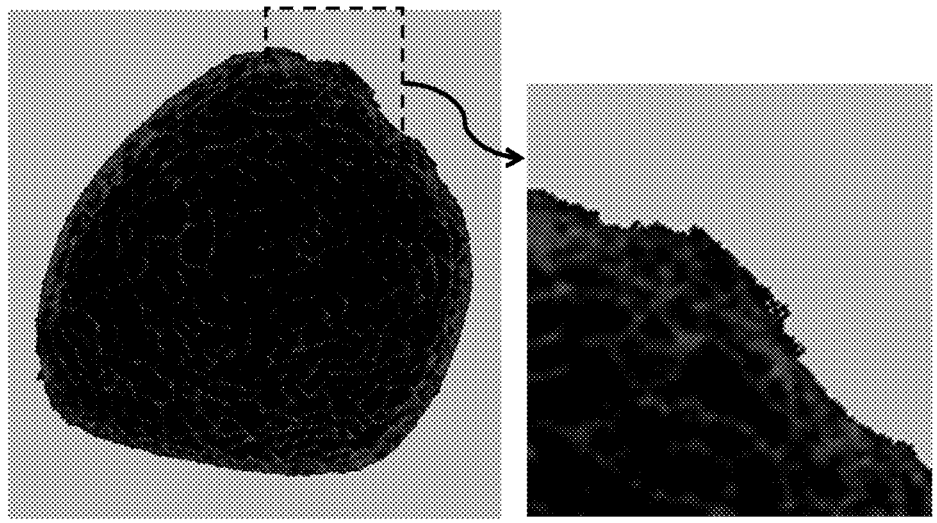
FIG. 42B is a cross sectional view of the same tibia, with bone and background delineated by the system of FIG. 1.
Figure 42A:
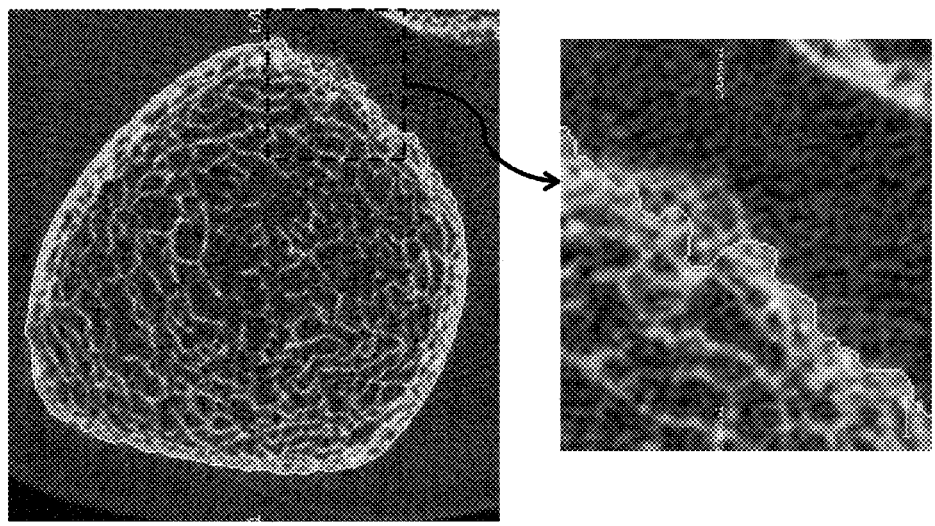
FIG. 42A is a cross sectional view of a tibia, with bone and background delineated by a system of the background art.

FIG. 42B, upper register, is the same cross section of the same bone separated from the background by image processor 16. It can be seen that image processor 16 has clearly separated bone from the surrounding soft tissue. The region erroneously segmented by conventional threshold-based software is shown in the lower register of this figure, in which it is apparent that image processor 16 has correctly separated this region from the background.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The invention claimed is:

1. A computer-implemented method for analysing a sample comprising a first material and a second material of generally different densities and having a junction therebetween, the method comprising:
    defining automatically at least one region of interest within an image of the sample, said region of interest having a width of one or more voxels or pixels;
    determining a density, intensity or attenuation profile within the region of interest;

determining a location of said junction within the image including defining a first reference point in the density, intensity or attenuation profile corresponding to said first material and employing the first reference point as a current reference point, and
- (i) determining a closest point to said current reference point that is in said density, intensity or attenuation profile and corresponding to the other of said first and second materials to that of the current reference point;
- (ii) determining for each peak in a segment of the density, intensity or attenuation profile between the current reference point and the closest point a difference between the value of the peak and a trough adjacent to the peak;
- (iii) determining a greatest of said differences; and
- (iv) locating a point of inflexion in the density, intensity or attenuation profile between the peak and the trough between which is said greatest of said differences.

2. A method as claimed in claim 1, comprising identifying a necrotic mass from surrounding healthy soft tissue from a difference in attenuation between the necrotic mass and the surrounding healthy soft tissue.

3. A method as claimed in claim 1, comprising identifying a tissue mass with high attenuation from surrounding healthy soft tissue with lower attenuation from a difference in attenuation between the high attenuation mass and the surrounding healthy soft tissue.

4. A method as claimed in claim 3, wherein the tissue mass comprises a tumour or calcified tissue.

5. A method as claimed in claim 1, wherein the first material is bone, and the method comprises:
analyzing the sample including rotating, translating or both rotating and translating one or more of said regions of interest;
defining a plurality of compartments within the sample, the compartments comprising any one or more of:
- i) a compartment bounded by a periosteal boundary and a beginning of the cortex;
- ii) a compartment bounded by a beginning of the cortex and a beginning of the compact cortex;
- iii) a compact (or hard) cortex compartment;
- iv) a trabecularized cortex compartment;
- v) a cortico-trabecular junction compartment; and
- vi) a trabecular compartment; and determining the local thickness, areas, density or porosity in each of the areas in one or more of said regions of interest.

6. A method as claimed in claim 1, comprising determining an amount of material in the first material relative to the second material using a first referent and a second referent, the first referent comprising a representative attenuation or density of the first material, the second referent comprising a representative attenuation or density of the second material.

7. A method as claimed in claim 6, wherein:
- i) the first referent is either a maximum or a 95th percentile value of the representative attenuation or density of the first material, and/or
- ii) the second referent is either a maximum or a 95th percentile value of the representative attenuation or density of the second material.

8. A method as claimed in claim 6, where the first material is bone and the second material is muscle tissue at least partially surrounding said bone, and the method includes estimating an amount of mineralized bone matrix in the one or more voxels or pixels.

9. A method as claimed in claim 8, comprising determining one or more mineralization indices by analysing voxels or pixels which only contain mineralized bone matrix.

10. A method as claimed in claim 6, comprising determining a porosity of the first material relative to a porosity of the second material.

11. A method as claimed in claim 10, where the first material is bone and the second material is muscle tissue at least partially surrounding said bone.

12. A method as claimed in claim 10, where the first material is rock or a plastics material.

13. A method as claimed in claim 10, where the second material is gas, air or a partial vacuum.

14. A method as claimed in claim 10, including selecting a range of porosity to be quantified based on a difference between the representative attenuation or density of the first material and the representative attenuation or density of the second material.

15. A method as claimed in claim 1, where the first material is bone and the second material is muscle tissue at least partially surrounding said bone, and the method further comprises determining one or more fat indices within said bone by comparing attenuation of voxels inside the bone to a representative attenuation of the muscle tissue.

16. A system for analysing a sample comprising a first material and a second material of generally different densities and having a junction therebetween, the system comprising:
at least one processor; and
memory, operatively connected to the at least one processor and containing instructions that, when executed by the at least one processor, cause the at least one processor to perform a method, the method comprising:
selecting at least one region of interest in an image of at least a portion of the sample that includes a portion of the first material and a portion of the second material;
determining a density, intensity or attenuation profile of the sample within the region of interest;
determining a location of said junction within the image, including:
defining a first reference point in the density, intensity or attenuation profile corresponding to said first material;
employing the first reference point as a current reference point;
determining a closest point to said current reference point that is in said density, intensity or attenuation profile and corresponding to the other of said first and second materials to that of the current reference point;
determining for each peak in a segment of the density, intensity or attenuation profile between the current reference point and the closest point a difference between the value of the peak and a trough adjacent to the peak;
determining a greatest of said differences; and
locating a point of inflexion in the density, intensity or attenuation profile between the peak and the trough between which is said greatest of said differences; and
outputting a result of said analysis.

17. A system as claimed in claim 16, wherein the method further comprises:
identifying a necrotic mass from surrounding healthy soft tissue from a difference in attenuation between the necrotic mass and the surrounding healthy soft tissue, and/or
identifying a tissue mass with high attenuation from surrounding healthy soft tissue with lower attenuation from a difference in attenuation between the high attenuation mass and the surrounding healthy soft tissue.

18. A system as claimed in claim 16, wherein the first material is bone, and the method further comprises:
analyzing the sample including rotating, translating or both rotating and translating one or more of said regions of interest;
defining a plurality of compartments within the sample, the compartments comprising any one or more of:
  i) a compartment bounded by a periosteal boundary and a beginning of the cortex;
  ii) a compartment bounded by a beginning of the cortex and a beginning of the compact cortex;
  iii) a compact (or hard) cortex compartment;
  iv) a trabecularized cortex compartment;
  v) a cortico-trabecular junction compartment; and
  vi) a trabecular compartment; and
determine the local thickness, areas, density or porosity in each of the areas in one or more of said regions of interest.

19. A system as claimed in claim 16, wherein the method further comprises determining an amount of material in the first material relative to the second material using a first referent and a second referent, the first referent comprising a representative attenuation or density of the first material, the second referent comprising a representative attenuation or density of the second material.

20. A system as claimed in 19, wherein the method further comprises determining a porosity of the first material relative to a porosity of the second material.

* * * * *